US005679774A

United States Patent [19]
Wolf

[11] Patent Number: 5,679,774
[45] Date of Patent: Oct. 21, 1997

[54] DNA SEQUENCES OF THE EBV GENOME, RECOMBINANT DNA MOLECULES, PROCESSES FOR PREPARING EBV-RELATED ANTIGENS, DIAGNOSTIC COMPOSITIONS AND PHARMACEUTICAL COMPOSITIONS CONTAINING SAID ANTIGENS

[76] Inventor: Hans J. Wolf, Josef Jägerhuber Str. 9, D-8130 Starnberg, Germany

[21] Appl. No.: 380,258

[22] Filed: Jan. 30, 1995

Related U.S. Application Data

[63] Continuation of Ser. No. 152,096, Nov. 15, 1993, abandoned, which is a continuation of Ser. No. 802,701, Dec. 9, 1991, abandoned, which is a continuation of Ser. No. 613,969, Nov. 15, 1990, abandoned, which is a continuation of Ser. No. 331,016, Mar. 29, 1989, abandoned, which is a continuation of Ser. No. 768,334, Aug. 22, 1985, abandoned.

[30] Foreign Application Priority Data

Aug. 23, 1984 [EP] European Pat. Off. ............. 84110089
Aug. 23, 1984 [EP] European Pat. Off. ............. 84110090

[51] Int. Cl.$^6$ ..................... A61K 39/245; C07K 14/05
[52] U.S. Cl. ............... 530/350; 424/185.1; 424/196.11; 424/230.1; 530/300; 530/395; 536/23.72
[58] Field of Search ............................ 530/300, 350, 530/395, 403; 424/185.1, 196.11, 230.1; 536/23.72

[56] References Cited

U.S. PATENT DOCUMENTS

| 4,654,419 | 3/1987 | Vaughan et al. | 530/326 |
|---|---|---|---|
| 4,707,358 | 11/1987 | Kieff et al. | 530/350 |

FOREIGN PATENT DOCUMENTS

| 035 384 | 9/1981 | European Pat. Off. . |
| 0 151 079 | 7/1985 | European Pat. Off. . |

OTHER PUBLICATIONS

BRL Catalogue & Reference Guide pp. 88–89, (1983).
Motz et al. Gene, 42: 303–312 (1986).
Grogan et al., Proc. Natl. Acad. Sci., 80, 7650–7653, (1983).
Luka et al., J. Immunol. Methods., 67: 145–156, (1984).
Li et al., J. Virology, 61: 2947–2949, (1987).
Wolf et al., J. Invest. Derm., 83:88s–95s, (1984).
Dölken et al., J. Immunol. Methods, 67:225–233 (1984).
Sternås et al., J. Immunol. Methods, 63:171–185 (1983).
Amann, E. et al., "Vectors bearing a hybrid trp–lac promoter useful for regulated expression of cloned genes in Escherichia coli", Gene 25: 167–178 (1983).
Amann, E. et al., "ATG vectors' for regulated high–level expression of cloned genes in Escherichia coli", Gene 40:183–190 (1985).
Rüther, U. and Müller–Hill, B., "Easy identification of cDNA clones", The EMBO Journal 2(10):1791–1794 (1983).

Goeddel et al., Proc. Natl. Acad. Sci. (USA) 76:106–110 (1979).
Shine, J. et al., Nature 285:456–461 (1980).
Sassenfeld and Brewer, Bio/Technology 76–81 (1984).
Seibl and Wolf, Virology 141:1–13 (1985).
Wolf, H. et al., CABIOS 4:187–191 (1988).
Garnier, J. et al., J. Mol. Biol. 120:97–120 (1978).
Hopp, T. P. et al., Proc. Natl. Acad. Sci. (USA) 78:3824–3828 (1981).
Chou, P. Y. et al., Biochemistry 13:222–245 (1974).
Geysen, H. M. et al., Proc. Natl. Acad. Sci. (USA) 81: 3998–4002 (1984).
Smith, J. C. et al., Gene 32:321–327 (1984).
Sassenfeld, H. M. et al., Bio/Technology 76–81 (1984).
Jan Klein, Immunology The Science of Self–Nonself Discrimination, John Wiley & Sons, New York, pp. 355–356 (1982).
Ebeling, A. et al., J. Virol., 47:421–433 (1983).
Reddehase, M. J. et al., Eur. J. Immunol., 14:56–61 (1984).
Reddehase, M. J. et al., J. Virol. 57:408–412 (1986).
Reddehase, M. J. et al., Nature, 312:369–371 (1984).
Talmadge et al., 13th International Congress of Chemotherapy, Spitzy et al (Ed.), Proceedings, Vienna, pp. 203/18–203/35 (1983).
Rudinger, Peptide Hormones, Parsons (Ed.), U. Park Press, Baltimore, pp. 1–7 (1976).
Baer et al., Nature, vol. 310, pp. 207–211 (1984).
Köhler et al., Nature, vol. 256, pp. 495–497 (1975).
Lampson, Monoclonal Antibodies, Hybridomas: A New Dimension in Biological Analyses, Kennett et al., (Eds.), pp. 395–397, Plenum Press, New York (1981).
Hummel et al., Proc. Natl. Acad. Sci. USA, vol. 79, pp. 5698–5702 (1982).
Devereux et al., Nucl. Acids Res, vol. 12, pp. 387–395 (1984).
Wolf, Immune Defic. and Cancer, Purtilo, ed., p. 233 (1984).
Henle et al., Int. J. Cancer, 8:272 (1971).
North et al., Int. J. Cancer, 26:231 (1980).
Thorley–Lawson et al., Proc. Natl. Acad. Sci., 77:5307 (1980).
Wells et al., J. Virol., 41:286 (1982).
Morgan et al., J. Med. Virol. 13:281 (1984).

(List continued on next page.)

Primary Examiner—Thomas M. Cunningham
Attorney, Agent, or Firm—Jayme A. Huleatt

[57] ABSTRACT

DNA sequences of the EBV genome coding for EBV-related antigens as well as the EBV-related antigens, fusion proteins containing the EBV-related antigens, recombinant DNA molecules containing the DNA sequences, cells containing the recombinant DNA molecules, processes for producing EBV-related antigens, and diagnostic and pharmaceutical compositions are disclosed.

9 Claims, 74 Drawing Sheets

OTHER PUBLICATIONS

Qualtiere and Pearson, *Int. J. Cancer*, 23:808 (1979).
Skare and Strominger, *Proc. Natl. Acad. Sci.*, 77:3860 (1980).
Cohen et al., *J. Virol.*, 49:102 (1984).
Bayliss and Wolf, *J. Gen. Virol.*, 56:105 (1981).
zur Hausen et al., *Nature*, 272:373 (1978).
Bayliss et al., *J. Virol. Meth.*, 7:229 (1983).
Baer et al., *Nature*, 310:207 (1984).
Vieira and Messing, *Gene*, 19:259 (1982).
Messing and Vieira, *Gene*, 19:269 (1982).
Hummel et al., *J. Virol.*, 49:413 (1984).
North et al., *Proc. Natl. Acad. Sci.*, 79:7504 (1982).
Thorley-Lawson and Poodry, *J. Virol.*, 43: 30 (1982).
Yanisch-Perron et al., *Gene*, 33:103 (1985).
Jilg and Wolf, *J. Infect. Dis.*, 152:222 (1985).
Buell et al., *J. Virol.*, 40:977 (1981).

47* from translation in vitro correlates with p54 from in vivo labeling

HgiA1
```
ATGCAGGGTGCACAGACTAGCGAGGATAATCTGGGCAGCCAGAGCCAGCCGGGTCCGTGC
├──┼──┼──┼──┼──┼──┼──┼──┼──┼──┼──┼──┤ 60
TACGTCCCACGTGTCTGATCGCTCCTATTAGACCCGTCGGTCTCGGTCGGCCCAGGCACG
Met Gln Gly Ala Gln Thr Ser Glu Asp Asn Leu Gly Ser Gln Ser Gln Pro Gly Pro Cys
```

```
GGCTACATCTACTTTTACCCCCTGGCCACCTACCCTCTTAGGGAGGTGGCCACACTGGGG
├──┼──┼──┼──┼──┼──┼──┼──┼──┼──┼──┼──┤ 120
CCGATGTAGATGAAAATGGGGGACCGGTGGATGGGAGAATCCCTCCACCGGTGTGACCCC
Gly Tyr Ile Tyr Phe Tyr Pro Leu Ala Thr Tyr Pro Leu Arg Glu Val Ala Thr Leu Gly
```

```
ACCGGCTACGCGGGCCACAGGTGCCTGACGGTGCCGCTCCTTTGCGGCATCACCGTGGAG
├──┼──┼──┼──┼──┼──┼──┼──┼──┼──┼──┼──┤ 180
TGGCCGATGCGCCCGGTGTCCACGGACTGCCACGGCGAGGAAACGCCGTAGTGGCACCTC
Thr Gly Tyr Ala Gly His Arg Cys Leu Thr Val Pro Leu Leu Cys Gly Ile Thr Val Glu
```

```
CCGGGCTTCAGCATCAATGTCAAGGCTCTGCACAGGAGGCCCGACCCCAACTGCGGGCTC
├──┼──┼──┼──┼──┼──┼──┼──┼──┼──┼──┼──┤ 240
GGCCCGAAGTCGTAGTTACAGTTCCGAGACGTGTCCTCCGGGCTGGGGTTGACGCCCGAG
Pro Gly Phe Ser Ile Asn Val Lys Ala Leu His Arg Arg Pro Asp Pro Asn Cys Gly Leu
```

```
CTACGCGCTACCTCCTATCACAGGGACATCTACGTGTTCCACAATGCCCATATGGTTCCC
├──┼──┼──┼──┼──┼──┼──┼──┼──┼──┼──┼──┤ 300
GATGCGCGATGGAGGATAGTGTCCCTGTAGATGCACAAGGTGTTACGGGTATACCAAGGG
Leu Arg Ala Thr Ser Tyr His Arg Asp Ile Tyr Val Phe His Asn Ala His Met Val Pro
```

Xho I
```
CCCATCTTTGAGGGGCCGGGTCTCGAGGCCCTCTGTGGCGAGACCAGGGAGGTGTTTGGG
├──┼──┼──┼──┼──┼──┼──┼──┼──┼──┼──┼──┤ 360
GGGTAGAAACTCCCCGGCCCAGAGCTCCGGGAGACACCGCTCTGGTCCCTCCACAAACCC
Pro Ile Phe Glu Gly Pro Gly Leu Glu Ala Leu Cys Gly Glu Thr Arg Glu Val Phe Gly
```

FIG. 3A

```
TACGACGCCTACAGCGCCCTACCGAGGGAAAGCTCCAAGCCGGGGGACTTCTTCCCCGAA
————————————————————————————————————————————————————————————+ 420
ATGCTGCGGATGTCGCGGGATGGCTCCCTTTCGAGGTTCGGCCCCCTGAAGAAGGGGCTT

Tyr Asp Ala Tyr Ser Ala Leu Pro Arg Glu Ser Ser Lys Pro Gly Asp Phe Phe Pro Glu

GGGCTAGATCCCTCTGCCTACCTGGGGGCGGTGGCAATAACCGAGGCCTTCAAGGAGCGA
————————————————————————————————————————————————————————————+ 480
CCCGATCTAGGGAGACGGATGGACCCCCGCCACCGTTATTGGCTCCGGAAGTTCCTCGCT

Gly Leu Asp Pro Ser Ala Tyr Leu Gly Ala Val Ala Ile Thr Glu Ala Phe Lys Glu Arg

CTCTACAGCGGAAACCTGGTGGCCATTCCATCGTTAAAACAGGAGGTAGCGGTGGGGCAG
————————————————————————————————————————————————————————————+ 540
GAGATGTCGCCTTTGGACCACCGGTAAGGTAGCAATTTTGTCCTCCATCGCCACCCCGTC

Leu Tyr Ser Gly Asn Leu Val Ala Ile Pro Ser Leu Lys Gln Glu Val Ala Val Gly Gln

TCTGCGAGCGTTAGGGTCCCGCTCTACGACAAGGAGGTGTTCCCAGAGGGCGTGCCCCAG
————————————————————————————————————————————————————————————+ 600
AGACGCTCGCAATCCCAGGGCGAGATGCTGTTCCTCCACAAGGGTCTCCCGCACGGGGTC

Ser Ala Ser Val Arg Val Pro Leu Tyr Asp Lys Glu Val Phe Pro Glu Gly Val Pro Gln

CTCCGCCAGTTTTACAACTCGGACCTCAGCCGCTGCATGCACGAGGCGCTGTACACCGGG
————————————————————————————————————————————————————————————+ 660
GAGGCGGTCAAAATGTTGAGCCTGGAGTCGGCGACGTACGTGCTCCGCGACATGTGGCCC

Leu Arg Gln Phe Tyr Asn Ser Asp Leu Ser Arg Cys Met His Glu Ala Leu Tyr Thr Gly

CTGGCGCAGGCGCTGCGCGTCCGACGGGTGGGCAAGCTGGTGGAGCTGCTGGAGAAGCAG
————————————————————————————————————————————————————————————+ 720
GACCGCGTCCGCGACGCGCAGGCTGCCCACCCGTTCGACCACCTCGACGACCTCTTCGTC

Leu Ala Gln Ala Leu Arg Val Arg Arg Val Gly Lys Leu Val Glu Leu Leu Glu Lys Gln
```

FIG. 3B

Pst I

```
AGCCTGCAGGACCAGGCCAAGGTGGCCAAGGTGGCCCCCCTCAAGGAGTTCCCAGCCTCA
————+————+————+————+————+————+————+————+————+————+————+————+ 780
TCGGACGTCCTGGTCCGGTTCCACCGGTTCCACCGGGGGGAGTTCCTCAAGGGTCGGAGT
```
Ser Leu Gln Asp Gln Ala Lys Val Ala Lys Val Ala Pro Leu Lys Glu Phe Pro Ala Ser

```
ACCATCAGTCACCCGGACTCGGGAGCCTTAATGATTGTGGACAGCGCGGCATGCGAGCTG
————+————+————+————+————+————+————+————+————+————+————+————+ 840
TGGTAGTCAGTGGGCCTGAGCCCTCGGAATTACTAACACCTGTCGCGCCGTACGCTCGAC
```
Thr Ile Ser His Pro Asp Ser Gly Ala Leu Met Ile Val Asp Ser Ala Ala Cys Glu Leu

```
GCGGTGAGCTACGCACCCGCCATGCTGGAGGCCTCGCACGAGACCCCGGCCAGCCTCAAC
————+————+————+————+————+————+————+————+————+————+————+————+ 900
CGCCACTCGATGCGTGGGCGGTACGACCTCCGGAGCGTGCTCTGGGGCCGGTCGGAGTTG
```
Ala Val Ser Tyr Ala Pro Ala Met Leu Glu Ala Ser His Glu Thr Pro Ala Ser Leu Asn

```
TACGACTCGTGGCCCCTGTTTGCCGACTGTGAGGGTCCAGAGGCCCGTGTGGCTGCGTTA
————+————+————+————+————+————+————+————+————+————+————+————+ 960
ATGCTGAGCACCGGGGACAAACGGCTGACACTCCCAGGTCTCCGGGCACACCGACGCAAT
```
Tyr Asp Ser Trp Pro Leu Phe Ala Asp Cys Glu Gly Pro Glu Ala Arg Val Ala Ala Leu

Bgl II

```
CACCGATATAATGCCAGCCTGGCCCCCCACGTGTCCACGCAGATCTTTGCCACCAATTCC
————+————+————+————+————+————+————+————+————+————+————+————+ 1020
GTGGCTATATTACGGTCGGACCGGGGGGTGCACAGGTGCGTCTAGAAACGGTGGTTAAGG
```
His Arg Tyr Asn Ala Ser Leu Ala Pro His Val Ser Thr Gln Ile Phe Ala Thr Asn Ser

```
GTCCTCTACGTCTCGGGGGTCTCGAAGTCAACCGGTCAGGGCAAGGAGAGTCTCTTTAAC
————+————+————+————+————+————+————+————+————+————+————+————+ 1080
CAGGAGATGCAGAGCCCCCAGAGCTTCAGTTGGCCAGTCCCGTTCCTCTCAGAGAAATTG
```
Val Leu Tyr Val Ser Gly Val Ser Lys Ser Thr Gly Gln Gly Lys Glu Ser Leu Phe Asn

FIG. 3C

```
                                    Pst I
                                    |
AGTTTCTACATGACCCACGGCCTGGGGACCCTGCAGGAGGGGACCTGGGACCCCTGCCGC
---+----+----+----+----+----+----+----+----+----+----+----+ 1140
TCAAAGATGTACTGGGTGCCGGACCCCTGGGACGTCCTCCCCTGGACCCTGGGGACGGCG
Ser Phe Tyr Met Thr His Gly Leu Gly Thr Leu Gln Glu Gly Thr Trp Asp Pro Cys Arg

CGACCCTGCTTCTCGGGCTGGGGTGGGCCAGACGTGACCGGAACCAACGGTCCGGGAAAC
---+----+----+----+----+----+----+----+----+----+----+----+ 1200
GCTGGGACGAAGAGCCCGACCCCACCCGGTCTGCACTGGCCTTGGTTGCCAGGCCCTTTG
Arg Pro Cys Phe Ser Gly Trp Gly Gly Pro Asp Val Thr Gly Thr Asn Gly Pro Gly Asn

TACGCTGTGGAGCACCTGGTCTATGCGGCCTCCTTCTCGCCCAACCTTCTTGCCCGCTAT
---+----+----+----+----+----+----+----+----+----+----+----+ 1260
ATGCGACACCTCGTGGACCAGATACGCCGGAGGAAGAGCGGGTTGGAAGAACGGGCGATA
Tyr Ala Val Glu His Leu Val Tyr Ala Ala Ser Phe Ser Pro Asn Leu Leu Ala Arg Tyr

Pst I                Sst1
           |                    |
GCCTACTACCTGCAGTTTTGCCAGGGACAGAAGAGCTCTCTGACCCCGGTGCCGGAGACG
---+----+----+----+----+----+----+----+----+----+----+----+ 1320
CGGATGATGGACGTCAAAACGGTCCCTGTCTTCTCGAGAGACTGGGGCCACGGCCTCTGC
Ala Tyr Tyr Leu Gln Phe Cys Gln Gly Gln Lys Ser Ser Leu Thr Pro Val Pro Glu Thr

GGCAGCTACGTGGCGGGGGCGGCCGCCAGTCCCATGTGCTCGCTCTGCGAGGGCCGGGCC
---+----+----+----+----+----+----+----+----+----+----+----+ 1380
CCGTCGATGCACCGCCCCCGCCGGCGGTCAGGGTACACGAGCGAGACGCTCCCGGCCCGG
Gly Ser Tyr Val Ala Gly Ala Ala Ala Ser Pro Met Cys Ser Leu Cys Glu Gly Arg Ala

CCGGCCGTGTGCCTGAACACGCTCTTCTTTAGGCTGAGGGACCGCTTCCCCCCCGTCATG
---+----+----+----+----+----+----+----+----+----+----+----+ 1440
GGCCGGCACACGGACTTGTGCGAGAAGAAATCCGACTCCCTGGCGAAGGGGGGCAGTAC
Pro Ala Val Cys Leu Asn Thr Leu Phe Phe Arg Leu Arg Asp Arg Phe Pro Pro Val Met
```

FIG. 3D

```
TCCACGCAGCGGAGGGACCCCTATGTGATCTCGGGGGCCTCGGGCTCCTACAACGAGACG
------+----+----+----+----+----+----+----+----+----+----+----+ 1500
AGGTGCGTCGCCTCCCTGGGGATACACTAGAGCCCCCGGAGCCCGAGGATGTTGCTCTGC

Ser Thr Gln Arg Arg Asp Pro Tyr Val Ile Ser Gly Ala Ser Gly Ser Tyr Asn Glu Thr
```

```
GACTTTTTGGGCAACTTTCTCAACTTCATCGATAAGGAGGACGACGGGCAGCGGCCGGAC
------+----+----+----+----+----+----+----+----+----+----+----+ 1560
CTGAAAAACCCGTTGAAAGAGTTGAAGTAGCTATTCCTCCTGCTGCCCGTCGCCGGCCTG

Asp Phe Leu Gly Asn Phe Leu Asn Phe Ile Asp Lys Glu Asp Asp Gly Gln Arg Pro Asp
```

```
GACGAGCCCCGCTACACCTACTGGCAGCTGAACCAGAACCTGCTGGAGCGGCTGTCTCGG
------+----+----+----+----+----+----+----+----+----+----+----+ 1620
CTGCTCGGGGCGATGTGGATGACCGTCGACTTGGTCTTGGACGACCTCGCCGACAGAGCC

Asp Glu Pro Arg Tyr Thr Tyr Trp Gln Leu Asn Gln Asn Leu Leu Glu Arg Leu Ser Arg
```

```
CTGGGCATAGACGCTGAAGGAAAGCTAGAGAAGGAGCCCCATGGCCCGCGTGACTTTGTC
------+----+----+----+----+----+----+----+----+----+----+----+ 1680
GACCCGTATCTGCGACTTCCTTTCGATCTCTTCCTCGGGGTACCGGGCGCACTGAAACAG

Leu Gly Ile Asp Ala Glu Gly Lys Leu Glu Lys Glu Pro His Gly Pro Arg Asp Phe Val
```

```
AAGATGTTCAAGGACGTGGATGCGGCGGTGGACGCCGAAGTGGTCCAGTTTATGAACAGC
------+----+----+----+----+----+----+----+----+----+----+----+ 1740
TTCTACAAGTTCCTGCACCTACGCCGCCACCTGCGGCTTCACCAGGTCAAATACTTGTCG

Lys Met Phe Lys Asp Val Asp Ala Ala Val Asp Ala Glu Val Val Gln Phe Met Asn Ser
```

```
ATGGCCAAGAACAACATCACCTACAAGGACCTGGTCAAGAGCTGCTACCACGTGATGCAG
------+----+----+----+----+----+----+----+----+----+----+----+ 1800
TACCGGTTCTTGTTGTAGTGGATGTTCCTGGACCAGTTCTCGACGATGGTGCACTACGTC

Met Ala Lys Asn Asn Ile Thr Tyr Lys Asp Leu Val Lys Ser Cys Tyr His Val Met Gln
```

```
TACTCGTGCAACCCCTTTGCGCAGCCCGCCTGCCCCATCTTCACCCAGCTGTTTTACCGC
------+----+----+----+----+----+----+----+----+----+----+----+ 1860
ATGAGCACGTTGGGGAAACGCGTCGGGCGGACGGGGTAGAAGTGGGTCGACAAAATGGCG

Tyr Ser Cys Asn Pro Phe Ala Gln Pro Ala Cys Pro Ile Phe Thr Gln Leu Phe Tyr Arg
```

FIG. 3E

```
                                        Pst I
                                        |
TCACTGCTGACCATCCTGCAGGACATCTCCCTGCCCATCTGTATGTGCTATGAGAATGAC
----+----+----+----+----+----+----+----+----+----+----+----+ 1920
AGTGACGACTGGTAGGACGTCCTGTAGAGGGACGGGTAGACATACACGATACTCTTACTG

Ser Leu Leu Thr Ile Leu Gln Asp Ile Ser Leu Pro Ile Cys Met Cys Tyr Glu Asn Asp

AACCCCGGGCTTGGCCAGAGCCCCCCAGAGTGGCTAAAGGGTCACTACCAGACGCTGTGC
----+----+----+----+----+----+----+----+----+----+----+----+ 1980
TTGGGGCCCGAACCGGTCTCGGGGGGTCTCACCGATTTCCCAGTGATGGTCTGCGACACG

Asn Pro Gly Leu Gly Gln Ser Pro Pro Glu Trp Leu Lys Gly His Tyr Gln Thr Leu Cys

HgiA1
 |
ACCAACTTTAGGAGCCTGGCCATCGACAAGGGGGTCCTCACGGCCAAGGAGGCCAAGGTG
----+----+----+----+----+----+----+----+----+----+----+----+ 2040
TGGTTGAAATCCTCGGACCGGTAGCTGTTCCCCCAGGAGTGCCGGTTCCTCCGGTTCCAC

Thr Asn Phe Arg Ser Leu Ala Ile Asp Lys Gly Val Leu Thr Ala Lys Glu Ala Lys Val

Pst I
                                              |
GTGCATGGGGAGCCCACCTGCGACCTGCCAGACCTGGACGCGGCCCTGCAGGGCCGGGTG
----+----+----+----+----+----+----+----+----+----+----+----+ 2100
CACGTACCCCTCGGGTGGACGCTGGACGGTCTGGACCTGCGCCGGGACGTCCCGGCCCAC

Val His Gly Glu Pro Thr Cys Asp Leu Pro Asp Leu Asp Ala Ala Leu Gln Gly Arg Val

TACGGCCGGCGGCTGCCTGTGCGCATGTCCAAGGTGCTGATGCTGTGCCCCAGGAACATC
----+----+----+----+----+----+----+----+----+----+----+----+ 2160
ATGCCGGCCGCCGACGGACACGCGTACAGGTTCCACGACTACGACACGGGGTCCTTGTAG

Tyr Gly Arg Arg Leu Pro Val Arg Met Ser Lys Val Leu Met Leu Cys Pro Arg Asn Ile

AAGATCAAGAACAGGGTGGTCTTCACGGGGGAGAATGCCGCCCTCCAGAACAGCTTCATC
----+----+----+----+----+----+----+----+----+----+----+----+ 2220
TTCTAGTTCTTGTCCCACCAGAAGTGCCCCCTCTTACGGCGGGAGGTCTTGTCGAAGTAG

Lys Ile Lys Asn Arg Val Val Phe Thr Gly Glu Asn Ala Ala Leu Gln Asn Ser Phe Ile
```

FIG. 3F

```
AAGTCCACTACCAGGAGGGAGAACTACATCATCAACGGGCCCTACATGAAATTCCTCAAC
────┼────┼────┼────┼────┼────┼────┼────┼────┼────┼────┼────┼  2280
TTCAGGTGATGGTCCTCCCTCTTGATGTAGTAGTTGCCCGGGATGTACTTTAAGGAGTTG

Lys Ser Thr Thr Arg Arg Glu Asn Tyr Ile Ile Asn Gly Pro Tyr Met Lys Phe Leu Asn

ACCTACCACAAGACCCTATTCCCGGACACTAAGCTCTCAAGCCTGTACCTGTGGCACAAC
────┼────┼────┼────┼────┼────┼────┼────┼────┼────┼────┼────┼  2340
TGGATGGTGTTCTGGGATAAGGGCCTGTGATTCGAGAGTTCGGACATGGACACCGTGTTG

Thr Tyr His Lys Thr Leu Phe Pro Asp Thr Lys Leu Ser Ser Leu Tyr Leu Trp His Asn

TTTTCCAGGCGGCGCTCGGTCCCTGTCCCCAGCGGGGCCAGCGCGGAGGAGTACTCTGAC
────┼────┼────┼────┼────┼────┼────┼────┼────┼────┼────┼────┼  2400
AAAAGGTCCGCCGCGAGCCAGGGACAGGGGTCGCCCCGGTCGCGCCTCCTCATGAGACTG

Phe Ser Arg Arg Arg Ser Val Pro Val Pro Ser Gly Ala Ser Ala Glu Glu Tyr Ser Asp

CTGGCCCTCTTTGTGGACGGGGGCTCCCGGGCCCACGAAGAGAGCAACGTCATAGATGTG
────┼────┼────┼────┼────┼────┼────┼────┼────┼────┼────┼────┼  2460
GACCGGGAGAAACACCTGCCCCCGAGGGCCCGGGTGCTTCTCTCGTTGCAGTATCTACAC

Leu Ala Leu Phe Val Asp Gly Gly Ser Arg Ala His Glu Glu Ser Asn Val Ile Asp Val

GTGCCTGGCAACCTGGTCACTTACGCCAAGCAGAGGCTCAACAACGCCATCCTGAAGGCG
────┼────┼────┼────┼────┼────┼────┼────┼────┼────┼────┼────┼  2520
CACGGACCGTTGGACCAGTGAATGCGGTTCGTCTCCGAGTTGTTGCGGTAGGACTTCCGC

Val Pro Gly Asn Leu Val Thr Tyr Ala Lys Gln Arg Leu Asn Asn Ala Ile Leu Lys Ala

TGCGGCCAGACCCAGTTCTACATCAGCCTGATTCAGGGACTGGTGCCGAGGACGCAGTCG
────┼────┼────┼────┼────┼────┼────┼────┼────┼────┼────┼────┼  2580
ACGCCGGTCTGGGTCAAGATGTAGTCGGACTAAGTCCCTGACCACGGCTCCTGCGTCAGC

Cys Gly Gln Thr Gln Phe Tyr Ile Ser Leu Ile Gln Gly Leu Val Pro Arg Thr Gln Ser

GTGCCCGCCCGTGACTACCCCCACGTACTGGGCACGCGGGCGGTGGAGTCGGCAGCGGCC
────┼────┼────┼────┼────┼────┼────┼────┼────┼────┼────┼────┼  2640
CACGGGCGGGCACTGATGGGGGTGCATGACCCGTGCGCCCGCCACCTCAGCCGTCGCCGG

Val Pro Ala Arg Asp Tyr Pro His Val Leu Gly Thr Arg Ala Val Glu Ser Ala Ala Ala
```

FIG. 3G

```
TACGCGGAGGCCACCTCCTCCCTTACTGCGACCACGGTGGTCTGCGCGGCCACAGACTGT
------+----+----+----+----+----+----+----+----+----+----+----+ 2700
ATGCGCCTCCGGTGGAGGAGGGAATGACGCTGGTGCCACCAGACGCGCCGGTGTCTGACA

Tyr Ala Glu Ala Thr Ser Ser Leu Thr Ala Thr Thr Val Val Cys Ala Ala Thr Asp Cys

CTTAGCCAGGTCTGCAAGGCCCGTCCGGTTGTCACGCTGCCAGTGACCATCAACAAGTAC
------+----+----+----+----+----+----+----+----+----+----+----+ 2760
GAATCGGTCCAGACGTTCCGGGCAGGCCAACAGTGCGACGGTCACTGGTAGTTGTTCATG

Leu Ser Gln Val Cys Lys Ala Arg Pro Val Val Thr Leu Pro Val Thr Ile Asn Lys Tyr

ACGGGGGTCAACGGCAACAACCAGATATTCCAGGCCGGGAACCTGGGATACTTTATGGGC
------+----+----+----+----+----+----+----+----+----+----+----+ 2820
TGCCCCCAGTTGCCGTTGTTGGTCTATAAGGTCCGGCCCTTGGACCCTATGAAATACCCG

Thr Gly Val Asn Gly Asn Asn Gln Ile Phe Gln Ala Gly Asn Leu Gly Tyr Phe Met Gly

Pst I
                          |
CGGGGCGTGGACAGGAACCTGCTGCAGGCCCCCGGGGCTGGGCTGCGCAAGCAGGCCGGG
------+----+----+----+----+----+----+----+----+----+----+----+ 2880
GCCCCGCACCTGTCCTTGGACGACGTCCGGGGGCCCCGACCCGACGCGTTCGTCCGGCCC

Arg Gly Val Asp Arg Asn Leu Leu Gln Ala Pro Gly Ala Gly Leu Arg Lys Gln Ala Gly

GGCTCTTCCATGCGGAAGAAGTTTGTCTTTGCCACCCCCACCCTAGGGTTGACCGTGAAG
------+----+----+----+----+----+----+----+----+----+----+----+ 2940
CCGAGAAGGTACGCCTTCTTCAAACAGAAACGGTGGGGGTGGGATCCCAACTGGCACTTC

Gly Ser Ser Met Arg Lys Lys Phe Val Phe Ala Thr Pro Thr Leu Gly Leu Thr Val Lys

CGCCGGACCCAAGCCGCGACCACATATGAGATTGAGAACATCAGGGCTGGCCTGGAGGCC
------+----+----+----+----+----+----+----+----+----+----+----+ 3000
GCGGCCTGGGTTCGGCGCTGGTGTATACTCTAACTCTTGTAGTCCCGACCGGACCTCCGG

Arg Arg Thr Gln Ala Ala Thr Thr Tyr Glu Ile Glu Asn Ile Arg Ala Gly Leu Glu Ala
```

FIG. 3H

```
ATTATATCACAAAAACAGGAGGAAGACTGTGTGTTTGATGTGGTGTGCAACCTTGTGGAT
————————————————————————————————————————————————————————————+ 3060
TAATATAGTGTTTTTGTCCTCCTTCTGACACACAAACTACACCACACGTTGGAACACCTA
 Ile Ile Ser Gln Lys Gln Glu Glu Asp Cys Val Phe Asp Val Val Cys Asn Leu Val Asp

GCCATGGGCGAGGCATGCGCCTCGCTGACTAGGGACGACGCGGAGTACTTATTGGGCCGC
————————————————————————————————————————————————————————————+ 3120
CGGTACCCGCTCCGTACGCGGAGCGACTGATCCCTGCTGCGCCTCATGAATAACCCGGCG
 Ala Met Gly Glu Ala Cys Ala Ser Leu Thr Arg Asp Asp Ala Glu Tyr Leu Leu Gly Arg

TTCTCCGTCCTGGCGGACAGCGTCCTAGAAACCCTGGCGACCATTGCCTCCAGCGGGATA
————————————————————————————————————————————————————————————+ 3180
AAGAGGCAGGACCGCCTGTCGCAGGATCTTTGGGACCGCTGGTAACGGAGGTCGCCCTAT
 Phe Ser Val Leu Ala Asp Ser Val Leu Glu Thr Leu Ala Thr Ile Ala Ser Ser Gly Ile

GAGTGGACGGCGGAGGCCGCTCGGGACTTTCTGGAGGGAGTGTGGGGTGGGCCCGGGGCA
————————————————————————————————————————————————————————————+ 3240
CTCACCTGCCGCCTCCGGCGAGCCCTGAAAGACCTCCCTCACACCCCACCCGGGCCCCGT
 Glu Trp Thr Ala Glu Ala Ala Arg Asp Phe Leu Glu Gly Val Trp Gly Gly Pro Gly Ala

GCCCAGGACAACTTTATCAGCGTGGCCGAGCCGGTCAGCACCGCGTCGCAGGCCTCGGCC
————————————————————————————————————————————————————————————+ 3300
CGGGTCCTGTTGAAATAGTCGCACCGGCTCGGCCAGTCGTGGCGCAGCGTCCGGAGCCGG
 Ala Gln Asp Asn Phe Ile Ser Val Ala Glu Pro Val Ser Thr Ala Ser Gln Ala Ser Ala

GGGCTGCTGCTGGGTGGAGGAGGGCAGGGCTCCGGGGGCAGACGCAAGCGCCGTCTGGCC
————————————————————————————————————————————————————————————+ 3360
CCCGACGACGACCCACCTCCTCCCGTCCCGAGGCCCCCGTCTGCGTTCGCGGCAGACCGG
 Gly Leu Leu Leu Gly Gly Gly Gly Gln Gly Ser Gly Gly Arg Arg Lys Arg Arg Leu Ala

Xho I
         |
ACCGTTCTCCCCGGACTCGAGGTC
—————————————————————→ 3384
TGGCAAGAGGGGCCTGAGCTCCAG
 Thr Val Leu Pro Gly Leu Glu Val
—————————————————→
```

FIG. 31

```
PstI                                      HindIII
    5'                                  3'
    G CGT CGT CGT CGT CGT TGA TA
   AC GTC GCA GCA GCA GCA GCA ACT ATT CGA
      Arg Arg Arg Arg Arg stop stop
```

```
 5'G CGT CGT CGT CGT CGT TGA TAA 3'
AC GTC GCA GCA GCA GCA GCA ACT ATT CGA                    Arg-linker Arg Arg Arg Arg Arg Stop Stop 5'GAC CTG CA                              A GCT TGG CAC 3'
  CTG G                                       ACC GTG      pUC 8

Pst I                                  Hind III
```

FIG. 16A

Induction with IPTG

Transcription/Translation

Lysis, Zentrifugation
↓
Pellet+ Urea
↓
Sephadex SP C-25 Chromatography
NaCl-Gradient
↓
Elution of the expressionproduct
in high salt
↓
Digest with Carboxypeptidase B
↓

↓
Sephadex SP C-25 Chromatography
↓
Elution of the expressionproduct
in low salt

FIG. 16B

```
      GGATCCGAAAAACTGGTCTATGGCTCGTGTGTCGATGCGCTGAAACCAACGGCAACAAAT
  1   ---------+---------+---------+---------+---------+---------+   60

TACTTACCTTGTTGTTGTGTGATGGGTAAAAACACACATCACACACTTAGGCCATAGGGA
 61   ---------+---------+---------+---------+---------+---------+  120

TGCTCACCGTAGCCGCGGCTCCAATCGCTTGAAGAAGTGTTCTTAGATCTAGTGGAAACC
121   ---------+---------+---------+---------+---------+---------+  180

TGCGGAGAATGGCTTCTCGCCCAGGGAGATCCGGCTGGGGTGGGAGCATGGGTCGTGCTG
181   ---------+---------+---------+---------+---------+---------+  240

GAGCTGACCCACCGGCATCATGATCGACCCGCTTTCTCTTCGTACCCTTCTGGGCCGGCT
241   ---------+---------+---------+---------+---------+---------+  300

CCAGGTGGGCATCTTCTGCTTCCTTTTCTGAGCTGCTATCTGATAACTCTATGAGGACAT
301   ---------+---------+---------+---------+---------+---------+  360

TTTCCCAATCTCCCGCCGATACCTGTTCCTGCACAACCGAGGTAGATGGGACTTCTTCTT
361   ---------+---------+---------+---------+---------+---------+  420

CCATGTTGTCATCCAGGGCCGGGGGACCCGGCCTGTCCTTGTCCATTTTGTCTGCAACAA
421   ---------+---------+---------+---------+---------+---------+  480

AAGTGTGACTCACCAACACCGCACCCCCCTTGTACCTATTAAAGAGGATGCTGCCTAGAA
481   ---------+---------+---------+---------+---------+---------+  540

ATCGGTGCCGAGACAATGGAGGCAGCCTTGCTTGTGTGTCAGTACACCATCCAGAGCCTG
541   ---------+---------+---------+---------+---------+---------+  600
                      MetGluAlaAlaLeuLeuValCysGlnTyrThrIleGlnSerLeu
                                                              EcoRI
      ATCCATCTCACGGGTGAAGATCCTGGTTTTTTCAATGTTGAGATTCCGGAATTCCCATTT
601   ---------+---------+---------+---------+---------+---------+  660
      IleHisLeuThrGlyGluAspProGlyPhePheAsnValGluIleProGluPheProPhe

TACCCCACATGCAATGTTTGCACGGCAGATGTCAATGTAACTATCAATTTCGATGTCGGG
661   ---------+---------+---------+---------+---------+---------+  720
      TyrProThrCysAsnValCysThrAlaAspValAsnValThrIleAsnPheAspValGly

GGCAAAAAGCATCAACTTGATCTTGACTTTGGCCAGCTGACACCCCATACGAAGGCTGTC
721   ---------+---------+---------+---------+---------+---------+  780
      GlyLysLysHisGlnLeuAspLeuAspPheGlyGlnLeuThrProHisThrLysAlaVal

TACCAACCTCGAGGTGCATTTGGTGGCTCAGAAAATGCCACCAATCTGTTTCTACTGGAG
781   ---------+---------+---------+---------+---------+---------+  840
      TyrGlnProArgGlyAlaPheGlyGlySerGluAsnAlaThrAsnLeuPheLeuLeuGlu
                                                              HindIII
      CTCCTTGGTGCAGGAGAATTGGCTCTAACTATGCGGTCTAAGAAGCTTCCAATTAACGTC
841   ---------+---------+---------+---------+---------+---------+  900
      LeuLeuGlyAlaGlyGluLeuAlaLeuThrMetArgSerLysLysLeuProIleAsnVal ACCACCGGAGAGGAGCAACAAGTAAGCCTGGAATCTGTAGATGTCTACTTTCAAGATGTG
901   ---------+---------+---------+---------+---------+---------+  960
      ThrThrGlyGluGluGlnGlnValSerLeuGluSerValAspValTyrPheGlnAspVal
```

FIG. 17A

```
      TTTGGAACCATGTGGTGCCACCATGCAGAAATGCAAAACCCCGTGTACCTGATACCAGAA
 961  ------------+----------+----------+----------+----------+----------+  1020
      PheGlyThrMetTrpCysHisHisAlaGluMetGlnAsnProValTyrLeuIleProGlu

ACAGTGCCATACATAAAGTGGGATAACTGTAATTCTACCAATATAACGGCAGTAGTGAGG
1021  ------------+----------+----------+----------+----------+----------+  1080
      ThrValProTyrIleLysTrpAspAsnCysAsnSerThrAsnIleThrAlaValValArg

GCACAGGGGCTGGATGTCACGCTACCCTTAAGTTTGCCAACGTCAGCTCAAGACTCGAAT
1081  ------------+----------+----------+----------+----------+----------+  1140
      AlaGlnGlyLeuAspValThrLeuProLeuSerLeuProThrSerAlaGlnAspSerAsn

TTCAGCGTAAAAACAGAAATGCTCGGTAATGAGATAGATATTGAGTGTATTATGGAGGAT
1141  ------------+----------+----------+----------+----------+----------+  1200
      PheSerValLysThrGluMetLeuGlyAsnGluIleAspIleGluCysIleMetGluAsp
                                                         PstI
      GGCGAAATTTCACAAGTTCTGCCCGGAGACAACAAATTTAACATCACCTGCAGTGGATAC
1201  ------------+----------+----------+----------+----------+----------+  1260
      GlyGluIleSerGlnValLeuProGlyAspAsnLysPheAsnIleThrCysSerGlyTyr
                                                       EcoRI
      GAGAGCCATGTTCCCAGCGGCGGAATTCTCACATCAACGAGTCCCGTGGCCACCCCAATA
1261  ------------+----------+----------+----------+----------+----------+  1320
      GluSerHisValProSerGlyGlyIleLeuThrSerThrSerProValAlaThrProIle

CCTGGTACAGGGTATGCATACAGCCTGCGTCTGACACCACGTCCAGTGTCACGATTTCTT
1321  ------------+----------+----------+----------+----------+----------+  1380
      ProGlyThrGlyTyrAlaTyrSerLeuArgLeuThrProArgProValSerArgPheLeu

GGCAATAACAGTATCCTGTACGTGTTTTACTCTGGGAATGGACCGAAGGCGAGCGGGGGA
1381  ------------+----------+----------+----------+----------+----------+  1440
      GlyAsnAsnSerIleLeuTyrValPheTyrSerGlyAsnGlyProLysAlaSerGlyGly

GATTACTGCATTCAGTCCAACATTGTGTTCTCTGATGAGATTCCAGCTTCACAGGACATG
1441  ------------+----------+----------+----------+----------+----------+  1500
      AspTyrCysIleGlnSerAsnIleValPheSerAspGluIleProAlaSerGlnAspMet

CCGACAAACACCACAGACATCACATATGTGGGTGACAATGCTACCTATTCAGTGCCAATG
1501  ------------+----------+----------+----------+----------+----------+  1560
      ProThrAsnThrThrAspIleThrTyrValGlyAspAsnAlaThrTyrSerValProMet

GTCACTTCTGAGGACGCAAACTCGCCAAATGTTACAGTGACTGCCTTTTGGGCCTGGCCA
1561  ------------+----------+----------+----------+----------+----------+  1620
      ValThrSerGluAspAlaAsnSerProAsnValThrValThrAlaPheTrpAlaTrpPro

AACAACACTGAAACTGACTTTAAGTGCAAATGGACTCTCACCTCGGGGACACCTTCGGGT
1621  ------------+----------+----------+----------+----------+----------+  1680
      AsnAsnThrGluThrAspPheLysCysLysTrpThrLeuThrSerGlyThrProSerGly

TGTGAAAATATTTCTGGTGCATTTGCGAGCAATCGGACATTTGACATTACTGTCTCGGGT
1681  ------------+----------+----------+----------+----------+----------+  1740
      CysGluAsnIleSerGlyAlaPheAlaSerAsnArgThrPheAspIleThrValSerGly

CTTGGCACGGCCCCCAAGACACTCATTATCACACGAACGGCTACCAATGCCACCACAACA
1741  ------------+----------+----------+----------+----------+----------+  1800
      LeuGlyThrAlaProLysThrLeuIleIleThrArgThrAlaThrAsnAlaThrThrThr
```

FIG. 17B

```
1801  ACCCACAAGGTTATATTCTCCAAGGCACCCGAGAGCACCACCACCTCCCCTACCTTGAAT  1860
      ---------+---------+---------+---------+---------+---------+
      ThrHisLysValIlePheSerLysAlaProGluSerThrThrThrSerProThrLeuAsn

1861  ACAACTGGATTTGCTGATCCCAATACAACGACAGGTCTACCCAGCTCTACTCACGTGCCT  1920
      ---------+---------+---------+---------+---------+---------+
      ThrThrGlyPheAlaAspProAsnThrThrThrGlyLeuProSerSerThrHisValPro

1921  ACCAACCTCACCGCACCTGCAAGCACAGGCCCCACTGTATCCACCGCGGATGTCACCAGC  1980
      ---------+---------+---------+---------+---------+---------+
      ThrAsnLeuThrAlaProAlaSerThrGlyProThrValSerThrAlaAspValThrSer

1981  CCAACACCAGCCGGCACAACGTCAGGCGCATCACCGGTGACACCAAGTCCATCTCCATGG  2040
      ---------+---------+---------+---------+---------+---------+
      ProThrProAlaGlyThrThrSerGlyAlaSerProValThrProSerProSerProTrp
                                )(-----

2041  GACAACGGCACAGAAAGTAAGGCCCCCGACATGACCAGCTCCACCTCACCAGTGACTACC  2100
      ---------+---------+---------+---------+---------+---------+
      AspAsnGlyThrGluSerLysAlaProAspMetThrSerSerThrSerProValThrThr

2101  CCAACCCCAAATGCCACCAGCCCCACCCCAGCAGTGACTACCCCAACCCCAAATGCCACC  2160
      ---------+---------+---------+---------+---------+---------+
      ProThrProAsnAlaThrSerProThrProAlaValThrThrProThrProAsnAlaThr

2161  AGCCCCACCCCAGCAGTGACTACCCCAACCCCAAATGCCACCAGCCCCACCTTGGGAAAA  2220
      ---------+---------+---------+---------+---------+---------+
      SerProThrProAlaValThrThrProThrProAsnAlaThrSerProThrLeuGlyLys

2221  ACAAGTCCTACCTCAGCAGTGACTACCCCAACCCCAAATGCCACCAGCCCCACCTTGGGA  2280
      ---------+---------+---------+---------+---------+---------+
      ThrSerProThrSerAlaValThrThrProThrProAsnAlaThrSerProThrLeuGly

2281  AAAACAAGCCCCACCTCAGCAGTGACTACCCCAACCCCAAATGCCACCAGCCCCACCTTG  2340
      ---------+---------+---------+---------+---------+---------+
      LysThrSerProThrSerAlaValThrThrProThrProAsnAlaThrSerProThrLeu

2341  GGAAAAACAAGCCCCACCTCAGCAGTGACTACCCCAACCCCAAATGCCACCGGCCCTACT  2400
      ---------+---------+---------+---------+---------+---------+
      GlyLysThrSerProThrSerAlaValThrThrProThrProAsnAlaThrGlyProThr

2401  GTGGGAGAAACAAGTCCACAGGCAAATGCCACCAACCACACCTTAGGAGGAACAAGTCCC  2460
      ---------+---------+---------+---------+---------+---------+
      ValGlyGluThrSerProGlnAlaAsnAlaThrAsnHisThrLeuGlyGlyThrSerPro

2461  ACCCCAGTAGTTACCAGCCAACCAAAAAATGCAACCAGTGCTGTTACCACAGGCCAACAT  2520
      ---------+---------+---------+---------+---------+---------+
      ThrProValValThrSerGlnProLysAsnAlaThrSerAlaValThrThrGlyGlnHis

2521  AACATAACTTCAAGTTCAACCTCTTCCATGTCACTGAGACCCAGTTCAAACCCAGAGACA  2580
      ---------+---------+---------+---------+---------+---------+
      AsnIleThrSerSerSerThrSerSerMetSerLeuArgProSerSerAsnProGluThr

2581  CTCAGCCCCTCCACCAGTGACAATTCAACGTCACATATGCCTTTACTAACCTCCGCTCAC  2640
      ---------+---------+---------+---------+---------+---------+
      LeuSerProSerThrSerAspAsnSerThrSerHisMetProLeuLeuThrSerAlaHis
```

FIG. 17C

```
              -----)(
         CCAACAGGTGGTGAAAATATAACACAGGTGACACCAGCCTCTATCAGCACACATCATGTG
2641     ---------+---------+---------+---------+---------+---------+    2700
         ProThrGlyGlyGluAsnIleThrGlnValThrProAlaSerIleSerThrHisHisVal

TCCACCAGTTCGCCAGCACCCCGCCCAGGCACCACCAGCCAAGCGTCAGGCCCTGGAAAC
2701     ---------+---------+---------+---------+---------+---------+    2760
         SerThrSerSerProAlaProArgProGlyThrThrSerGlnAlaSerGlyProGlyAsn

AGTTCCACATCCACAAAACCGGGGGAGGTTAATGTCACCAAAGGCACGCCCCCCCAAAAT
2761     ---------+---------+---------+---------+---------+---------+    2820
         SerSerThrSerThrLysProGlyGluValAsnValThrLysGlyThrProProGlnAsn

GCAACGTCGCCCCAGGCCCCCAGTGGCCAAAAGACGGCGGTTCCCACGGTCACCTCAACA
2821     ---------+---------+---------+---------+---------+---------+    2880
         AlaThrSerProGlnAlaProSerGlyGlnLysThrAlaValProThrValThrSerThr

GGTGGAAAGGCCAATTCTACCACCGGTGGAAAGCACACCACAGGACATGGAGCCCGGACA
2881     ---------+---------+---------+---------+---------+---------+    2940
         GlyGlyLysAlaAsnSerThrThrGlyGlyLysHisThrThrGlyHisGlyAlaArgThr

AGTACAGAGCCCACCACAGATTACGGCGGTGATTCAACTACGCCAAGACCGAGATACAAT
2941     ---------+---------+---------+---------+---------+---------+    3000
         SerThrGluProThrThrAspTyrGlyGlyAspSerThrThrProArgProArgTyrAsn

GCGACCACCTATCTACCTCCCAGCACTTCTAGCAAACTGCGGCCCCGCTGGACTTTTACG
3001     ---------+---------+---------+---------+---------+---------+    3060
         AlaThrThrTyrLeuProProSerThrSerSerLysLeuArgProArgTrpThrPheThr

AGCCCACCGGTTACCACAGCCCAAGCCACCGTGCCAGTCCCGCCAACGTCCCAGCCCAGA
3061     ---------+---------+---------+---------+---------+---------+    3120
         SerProProValThrThrAlaGlnAlaThrValProValProThrSerGlnProArg
                                          PstI          **********************
         TTCTCAAACCTCTCCATGCTAGTACTGCAGTGGGCCTCTCTGGCTGTGCTGACCCTTCTG
3121     ---------+---------+---------+---------+---------+---------+    3180
         PheSerAsnLeuSerMetLeuValLeuGlnTrpAlaSerLeuAlaValLeuThrLeuLeu
         ***********
         CTGCTGCTGGTCATGGCGGACTGCGCCTTTAGGCGTAACTTGTCTACATCCCATACCTAC
3181     ---------+---------+---------+---------+---------+---------+    3240
         LeuLeuLeuValMetAlaAspCysAlaPheArgArgAsnLeuSerThrSerHisThrTyr
                                                              ++++++++
         ACCACCCCACCATATGATGACGCCGAGACCTATGTATAAAGTCAATAAAAATTTATTAAT
3241     ---------+---------+---------+---------+---------+---------+    3300
         ThrThrProProTyrAspAspAlaGluThrTyrValEnd

CAGAAATTTGCACTTTCTTTGCTTCACGTCCCCGGGAGCGGGAGCGGGCACGTCGGGTGG
3301     ---------+---------+---------+---------+---------+---------+    3360

CGTTGGGGTCGTTTGATTCTCGTGGTCGTGTTCCCTCACC
3361     ---------+---------+---------+   3400
```

FIG. 17D

```
      ACCATGATTACGGATTCACTGGCCGTCGTTTTACAACGTCGTGACTGGGAAAACCCTGGC
  1   ----------+---------+---------+---------+---------+---------+   60
        MetIleThrAspSerLeuAlaValValLeuGlnArgArgAspTrpGluAsnProGly

GTTACCCAACTTAATCGCCTTGCAGCACATCCCCCTTTCGCCAGCTGGCGTAATAGCGAA
 61   ----------+---------+---------+---------+---------+---------+  120
        ValThrGlnLeuAsnArgLeuAlaAlaHisProProPheAlaSerTrpArgAsnSerGlu

GAGGCCCGCACCGATCGCCCTTCCCAACAGTTGCGCAGCCTGAATGGCGAATGGCGCTTT
121   ----------+---------+---------+---------+---------+---------+  180
        GluAlaArgThrAspArgProSerGlnGlnLeuArgSerLeuAsnGlyGluTrpArgPhe

GCCTGGTTTCCGGCACCAGAAGCGGTGCCGGAAAGCTGGCTGGAGTGCGATCTTCCTGAG
181   ----------+---------+---------+---------+---------+---------+  240
        AlaTrpPheProAlaProGluAlaValProGluSerTrpLeuGluCysAspLeuProGlu

GCCGATACTGTCGTCGTCCCCTCAAACTGGCAGATGCACGGTTACGATGCGCCCATCTAC
241   ----------+---------+---------+---------+---------+---------+  300
        AlaAspThrValValValProSerAsnTrpGlnMetHisGlyTyrAspAlaProIleTyr

ACCAACGTAACCTATCCCATTACGGTCAATCCGCCGTTTGTTCCCACGGAGAATCCGACG
301   ----------+---------+---------+---------+---------+---------+  360
        ThrAsnValThrTyrProIleThrValAsnProProPheValProThrGluAsnProThr

GGTTGTTACTCGCTCACATTTAATGTTGATGAAAGCTGGCTACAGGAAGGCCAGACGCGA
361   ----------+---------+---------+---------+---------+---------+  420
        GlyCysTyrSerLeuThrPheAsnValAspGluSerTrpLeuGlnGluGlyGlnThrArg

ATTATTTTTGATGGCGTTAACTCGGCGTTTCATCTGTGGTGCAACGGGCGCTGGGTCGGT
421   ----------+---------+---------+---------+---------+---------+  480
        IleIlePheAspGlyValAsnSerAlaPheHisLeuTrpCysAsnGlyArgTrpValGly

TACGGCCAGGACAGTCGTTTGCCGTCTGAATTTGACCTGAGCGCATTTTTACGCGCCGGA
481   ----------+---------+---------+---------+---------+---------+  540
        TyrGlyGlnAspSerArgLeuProSerGluPheAspLeuSerAlaPheLeuArgAlaGly

GAAAACCGCCTCGCGGTGATGGTGCTGCGTTGGAGTGACGGCAGTTATCTGGAAGATCAG
541   ----------+---------+---------+---------+---------+---------+  600
        GluAsnArgLeuAlaValMetValLeuArgTrpSerAspGlySerTyrLeuGluAspGln

GATATGTGGCGGATGAGCGGCATTTTCCGTGACGTCTCGTTGCTGCATAAACCGACTACA
601   ----------+---------+---------+---------+---------+---------+  660
        AspMetTrpArgMetSerGlyIlePheArgAspValSerLeuLeuHisLysProThrThr

CAAATCAGCGATTTCCATGTTGCCACTCGCTTTAATGATGATTTCAGCCGCGCTGTACTG
661   ----------+---------+---------+---------+---------+---------+  720
        GlnIleSerAspPheHisValAlaThrArgPheAsnAspAspPheSerArgAlaValLeu

GAGGCTGAAGTTCAGATGTGCGGCGAGTTGCGTGACTACCTACGGGTAACAGTTTCTTTA
721   ----------+---------+---------+---------+---------+---------+  780
        GluAlaGluValGlnMetCysGlyGluLeuArgAspTyrLeuArgValThrValSerLeu

TGGCAGGGTGAAACGCAGGTCGCCAGCGGCACCGCGCCTTTCGGCGGTGAAATTATCGAT
781   ----------+---------+---------+---------+---------+---------+  840
        TrpGlnGlyGluThrGlnValAlaSerGlyThrAlaProPheGlyGlyGluIleIleAsp

GAGCGTGGTGGTTATGCCGATCGCGTCACACTACGTCTGAACGTCGAAAACCCGAAACTG
841   ----------+---------+---------+---------+---------+---------+  900
```

FIG. 21A

```
                  GluArgGlyGlyTyrAlaAspArgValThrLeuArgLeuAsnValGluAsnProLysLeu

TGGAGCGCCGAAATCCCGAATCTCTATCGTGCGGTGGTTGAACTGCACACCGCCGACGGC
     901    ---------+---------+---------+---------+---------+---------+    960
            TrpSerAlaGluIleProAsnLeuTyrArgAlaValValGluLeuHisThrAlaAspGly

ACGCTGATTGAAGCAGAAGCCTGCGATGTCGGTTTCCGCGAGGTGCGGATTGAAAATGGT
     961    ---------+---------+---------+---------+---------+---------+   1020
            ThrLeuIleGluAlaGluAlaCysAspValGlyPheArgGluValArgIleGluAsnGly

CTGCTGCTGCTGAACGGCAAGCCGTTGCTGATTCGAGGCGTTAACCGTCACGAGCATCAT
    1021    ---------+---------+---------+---------+---------+---------+   1080
            LeuLeuLeuLeuAsnGlyLysProLeuLeuIleArgGlyValAsnArgHisGluHisHis

CCTCTGCATGGTCAGGTCATGGATGAGCAGACGATGGTGCAGGATATCCTGCTGATGAAG
    1081    ---------+---------+---------+---------+---------+---------+   1140
            ProLeuHisGlyGlnValMetAspGluGlnThrMetValGlnAspIleLeuLeuMetLys

CAGAACAACTTTAACGCCGTGCGCTGTTCGCATTATCCGAACCATCCGCTGTGGTACACG
    1141    ---------+---------+---------+---------+---------+---------+   1200
            GlnAsnAsnPheAsnAlaValArgCysSerHisTyrProAsnHisProLeuTrpTyrThr

CTGTGCGACCGCTACGGCCTGTATGTGGTGGATGAAGCCAATATTGAAACCCACGGCATG
    1201    ---------+---------+---------+---------+---------+---------+   1260
            LeuCysAspArgTyrGlyLeuTyrValValAspGluAlaAsnIleGluThrHisGlyMet

GTGCCAATGAATCGTCTGACCGATGATCCGCGCTGGCTACCGGCGATGAGCGAACGCGTA
    1261    ---------+---------+---------+---------+---------+---------+   1320
            ValProMetAsnArgLeuThrAspAspProArgTrpLeuProAlaMetSerGluArgVal

ACGCGAATGGTGCAGCGCGATCGTAATCACCCGAGTGTGATCATCTGGTCGCTGGGGAAT
    1321    ---------+---------+---------+---------+---------+---------+   1380
            ThrArgMetValGlnArgAspArgAsnHisProSerValIleIleTrpSerLeuGlyAsn

GAATCAGGCCACGGCGCTAATCACGACGCGCTGTATCGCTGGATCAAATCTGTCGATCCT
    1381    ---------+---------+---------+---------+---------+---------+   1440
            GluSerGlyHisGlyAlaAsnHisAspAlaLeuTyrArgTrpIleLysSerValAspPro

TCCCGCCCGGTGCAGTATGAAGGCGGCGGAGCCGACACCACGGCCACCGATATTATTTGC
    1441    ---------+---------+---------+---------+---------+---------+   1500
            SerArgProValGlnTyrGluGlyGlyGlyAlaAspThrThrAlaThrAspIleIleCys

CCGATGTACGCGCGCGTGGATGAAGACCAGCCCTTCCCGGCTGTGCCGAAATGGTCCATC
    1501    ---------+---------+---------+---------+---------+---------+   1560
            ProMetTyrAlaArgValAspGluAspGlnProPheProAlaValProLysTrpSerIle

AAAAAATGGCTTTCGCTACCTGGAGAGACGCGCCCGCTGATCCTTTGCGAATACGCCCAC
    1561    ---------+---------+---------+---------+---------+---------+   1620
            LysLysTrpLeuSerLeuProGlyGluThrArgProLeuIleLeuCysGluTyrAlaHis

GCGATGGGTAACAGTCTTGGCGGTTTCGCTAAATACTGGCAGGCGTTTCGTCAGTATCCC
    1621    ---------+---------+---------+---------+---------+---------+   1680
            AlaMetGlyAsnSerLeuGlyGlyPheAlaLysTyrTrpGlnAlaPheArgGlnTyrPro
```

FIG. 21B

```
      CGTTTACAGGGCGGCTTCGTCTGGGACTGGGTGGATCAGTCGCTGATTAAATATGATGAA
1681  ---------+---------+---------+---------+---------+---------+  1740
      ArgLeuGlnGlyGlyPheValTrpAspTrpValAspGlnSerLeuIleLysTyrAspGlu

AACGGCAACCCGTGGTCGGCTTACGGCGGTGATTTTGGCGATACGCCGAACGATCGCCAG
1741  ---------+---------+---------+---------+---------+---------+  1800
      AsnGlyAsnProTrpSerAlaTyrGlyGlyAspPheGlyAspThrProAsnAspArgGln

TTCTGTATGAACGGTCTGGTCTTTGCCGACCGCACGCCGCATCCAGCGCTGACGGAAGCA
1801  ---------+---------+---------+---------+---------+---------+  1860
      PheCysMetAsnGlyLeuValPheAlaAspArgThrProHisProAlaLeuThrGluAla

AAACACCAGCAGCAGTTTTTCCAGTTCCGTTTATCCGGGCAAACCATCGAAGTGACCAGC
1861  ---------+---------+---------+---------+---------+---------+  1920
      LysHisGlnGlnGlnPhePheGlnPheArgLeuSerGlyGlnThrIleGluValThrSer

GAATACCTGTTCCGTCATAGCGATAACGAGCTCCTGCACTGGATGGTGGCGCTGGATGGT
1921  ---------+---------+---------+---------+---------+---------+  1980
      GluTyrLeuPheArgHisSerAspAsnGluLeuLeuHisTrpMetValAlaLeuAspGly

AAGCCGCTGGCAAGCGGTGAAGTGCCTCTGGATGTCGCTCCACAAGGTAAACAGTTGATT
1981  ---------+---------+---------+---------+---------+---------+  2040
      LysProLeuAlaSerGlyGluValProLeuAspValAlaProGlnGlyLysGlnLeuIle

GAACTGCCTGAACTACCGCAGCCGGAGAGCGCCGGGCAACTCTGGCTCACAGTACGCGTA
2041  ---------+---------+---------+---------+---------+---------+  2100
      GluLeuProGluLeuProGlnProGluSerAlaGlyGlnLeuTrpLeuThrValArgVal

GTGCAACCGAACGCGACCGCATGGTCAGAAGCCGGGCACATCAGCGCCTGGCAGCAGTGG
2101  ---------+---------+---------+---------+---------+---------+  2160
      ValGlnProAsnAlaThrAlaTrpSerGluAlaGlyHisIleSerAlaTrpGlnGlnTrp

CGTCTGGCGGAAAACCTCAGTGTGACGCTCCCCGCCGCGTCCCACGCCATCCCGCATCTG
2161  ---------+---------+---------+---------+---------+---------+  2220
      ArgLeuAlaGluAsnLeuSerValThrLeuProAlaAlaSerHisAlaIleProHisLeu

ACCACCAGCGAAATGGATTTTTGCATCGAGCTGGGTAATAAGCGTTGGCAATTTAACCGC
2221  ---------+---------+---------+---------+---------+---------+  2280
      ThrThrSerGluMetAspPheCysIleGluLeuGlyAsnLysArgTrpGlnPheAsnArg

CAGTCAGGCTTTCTTTCACAGATGTGGATTGGCGATAAAAAACAACTGCTGACGCCGCTG
2281  ---------+---------+---------+---------+---------+---------+  2340
      GlnSerGlyPheLeuSerGlnMetTrpIleGlyAspLysLysGlnLeuLeuThrProLeu

CGCGATCAGTTCACCCGTGCACCGCTGGATAACGACATTGGCGTAAGTGAAGCGACCCGC
2341  ---------+---------+---------+---------+---------+---------+  2400
      ArgAspGlnPheThrArgAlaProLeuAspAsnAspIleGlyValSerGluAlaThrArg

ATTGACCCTAACGCCTGGGTCGAACGCTGGAAGGCGGCGGGCCATTACCAGGCCGAAGCA
2401  ---------+---------+---------+---------+---------+---------+  2460
      IleAspProAsnAlaTrpValGluArgTrpLysAlaAlaGlyHisTyrGlnAlaGluAla

GCGTTGTTGCAGTGCACGGCAGATACACTTGCTGATGCGGTGCTGATTACGACCGCTCAC
2461  ---------+---------+---------+---------+---------+---------+  2520
      AlaLeuLeuGlnCysThrAlaAspThrLeuAlaAspAlaValLeuIleThrThrAlaHis
```

FIG. 21C

```
       GCGTGGCAGCATCAGGGGAAAACCTTATTTATCAGCCGGAAAACCTACCGGATTGATGGT
2521   ---------+---------+---------+---------+---------+---------+   2580
       AlaTrpGlnHisGlnGlyLysThrLeuPheIleSerArgLysThrTyrArgIleAspGly

AGTGGTCAAATGGCGATTACCGTTGATGTTGAAGTGGCGAGCGATACACCGCATCCGGCG
2581   ---------+---------+---------+---------+---------+---------+   2640
       SerGlyGlnMetAlaIleThrValAspValGluValAlaSerAspThrProHisProAla

CGGATTGGCCTGAACTGCCAGCTGGCGCAGGTAGCAGAGCGGGTAAACTGGCTCGGATTA
2641   ---------+---------+---------+---------+---------+---------+   2700
       ArgIleGlyLeuAsnCysGlnLeuAlaGlnValAlaGluArgValAsnTrpLeuGlyLeu

GGGCCGCAAGAAAACTATCCCGACCGCCTTACTGCCGCCTGTTTTGACCGCTGGGATCTG
2701   ---------+---------+---------+---------+---------+---------+   2760
       GlyProGlnGluAsnTyrProAspArgLeuThrAlaAlaCysPheAspArgTrpAspLeu

CCATTGTCAGACATGTATACCCCGTACGTCTTCCCGAGCGAAAACGGTCTGCGCTGCGGG
2761   ---------+---------+---------+---------+---------+---------+   2820
       ProLeuSerAspMetTyrThrProTyrValPheProSerGluAsnGlyLeuArgCysGly

ACGCGCGAATTGAATTATGGCCCACACCAGTGGCGCGGCGACTTCCAGTTCAACATCAGC
2821   ---------+---------+---------+---------+---------+---------+   2880
       ThrArgGluLeuAsnTyrGlyProHisGlnTrpArgGlyAspPheGlnPheAsnIleSer

CGCTACAGTCAACAGCAACTGATGGAAACCAGCCATCGCCATCTGCTGCACGCGGAAGAA
2881   ---------+---------+---------+---------+---------+---------+   2940
       ArgTyrSerGlnGlnGlnLeuMetGluThrSerHisArgHisLeuLeuHisAlaGluGlu

GGCACATGGCTGAATATCGACGGTTTCCATATGGGGATTGGTGGCGACGACTCCTGGAGC
2941   ---------+---------+---------+---------+---------+---------+   3000
       GlyThrTrpLeuAsnIleAspGlyPheHisMetGlyIleGlyGlyAspAspSerTrpSer

CCGTCAGTATCGGCGGAATTCCAGCTGAGCGCCGGTCGCTACCATTACCAGTTGGTCTGG
3001   ---------+---------+---------+---------+---------+---------+   3060
       ProSerValSerAlaGluPheGlnLeuSerAlaGlyArgTyrHisTyrGlnLeuValTrp

TGTCAAAAAggggatccgtcgacctgcaGTGGATACGAGAGCCATGTTCCCAGCGGCGGA
3061   ---------+---------+---------+---------+---------+---------+   3120
       CysGlnLysGlyAspProSerThrCysSerGlyTyrGluSerHisValProSerGlyGly ATTCTCACATCAACGAGTCCCGTGGCCACCCCAATACCTGGTACAGGGTATGCATACAGC
3121   ---------+---------+---------+---------+---------+---------+   3180
       IleLeuThrSerThrSerProValAlaThrProIleProGlyThrGlyTyrAlaTyrSer CTGCGTCTGACACCACGTCCAGTGTCACGATTTCTTGGCAATAACAGTATCCTGTACGTG
3181   ---------+---------+---------+---------+---------+---------+   3240
       LeuArgLeuThrProArgProValSerArgPheLeuGlyAsnAsnSerIleLeuTyrVal TTTTACTCTGGGAATGGACCGAAGGCGAGCGGGGGAGATTACTGCATTCAGTCCAACATT
3241   ---------+---------+---------+---------+---------+---------+   3300
       PheTyrSerGlyAsnGlyProLysAlaSerGlyGlyAspTyrCysIleGlnSerAsnIle GTGTTCTCTGATGAGATTCCAGCTTCACAGGACATGCCGACAAACACCACAGACATCACA
3301   ---------+---------+---------+---------+---------+---------+   3360
       ValPheSerAspGluIleProAlaSerGlnAspMetProThrAsnThrThrAspIleThr
```

FIG. 21D

```
       TATGTGGGTGACAATGCTACCTATTCAGTGCCAATGGTCACTTCTGAGGACGCAAACTCG
3361   ---------+---------+---------+---------+---------+---------+   3420
       TyrValGlyAspAsnAlaThrTyrSerValProMetValThrSerGluAspAlaAsnSer

CCAAATGTTACAGTGACTGCCTTTTGGGCCTGGCCAAACAACACTGAAACTGACTTTAAG
3421   ---------+---------+---------+---------+---------+---------+   3480
       ProAsnValThrValThrAlaPheTrpAlaTrpProAsnAsnThrGluThrAspPheLys

TGCAAATGGACTCTCACCTCGGGGACACCTTCGGGTTGTGAAAATATTTCTGGTGCATTT
3481   ---------+---------+---------+---------+---------+---------+   3540
       CysLysTrpThrLeuThrSerGlyThrProSerGlyCysGluAsnIleSerGlyAlaPhe

GCGAGCAATCGGACATTTGACATTACTGTCTCGGGTCTTGGCACGGCCCCCAAGACACTC
3541   ---------+---------+---------+---------+---------+---------+   3600
       AlaSerAsnArgThrPheAspIleThrValSerGlyLeuGlyThrAlaProLysThrLeu

ATTATCACACGAACGGCTACCAATGCCACCACAACAACCCACAAGGTTATATTCTCCAAG
3601   ---------+---------+---------+---------+---------+---------+   3660
       IleIleThrArgThrAlaThrAsnAlaThrThrThrThrHisLysValIlePheSerLys

GCACCCGAGAGCACCACCACCTCCCCTACCTTGAATACAACTGGATTTGCTGATCCCAAT
3661   ---------+---------+---------+---------+---------+---------+   3720
       AlaProGluSerThrThrThrSerProThrLeuAsnThrThrGlyPheAlaAspProAsn

ACAACGACAGGTCTACCCAGCTCTACTCACGTGCCTACCAACCTCACCGCACCTGCAAGC
3721   ---------+---------+---------+---------+---------+---------+   3780
       ThrThrThrGlyLeuProSerSerThrHisValProThrAsnLeuThrAlaProAlaSer

ACAGGCCCCACTGTATCCACCGCGGATGTCACCAGCCCAACACCAGCCGGCACAACGTCA
3781   ---------+---------+---------+---------+---------+---------+   3840
       ThrGlyProThrValSerThrAlaAspValThrSerProThrProAlaGlyThrThrSer

GGCGCATCACCGGTGACACCAAGTCCATCTCCATGGGACAACGGCACAGAAAGTAAGGCC
3841   ---------+---------+---------+---------+---------+---------+   3900
       GlyAlaSerProValThrProSerProSerProTrpAspAsnGlyThrGluSerLysAla

CCCGACATGACCAGCTCCACCTCACCAGTGACTACCCCAACCCCAAATGCCACCAGCCCC
3901   ---------+---------+---------+---------+---------+---------+   3960
       ProAspMetThrSerSerThrSerProValThrThrProThrProAsnAlaThrSerPro

ACCCCAGCAGTGACTACCCCAACCCCAAATGCCACCAGCCCCACCCCAGCAGTGACTACC
3961   ---------+---------+---------+---------+---------+---------+   4020
       ThrProAlaValThrThrProThrProAsnAlaThrSerProThrProAlaValThrThr

CCAACCCCAAATGCCACCAGCCCCACCTTGGGAAAAACAAGTCCTACCTCAGCAGTGACT
4021   ---------+---------+---------+---------+---------+---------+   4080
       ProThrProAsnAlaThrSerProThrLeuGlyLysThrSerProThrSerAlaValThr

ACCCCAACCCCAAATGCCACCAGCCCCACCTTGGGAAAAACAAGCCCCACCTCAGCAGTG
4081   ---------+---------+---------+---------+---------+---------+   4140
       ThrProThrProAsnAlaThrSerProThrLeuGlyLysThrSerProThrSerAlaVal

ACTACCCCAACCCCAAATGCCACCAGCCCCACCTTGGGAAAAACAAGCCCCACCTCAGCA
4141   ---------+---------+---------+---------+---------+---------+   4200
       ThrThrProThrProAsnAlaThrSerProThrLeuGlyLysThrSerProThrSerAla
```

FIG. 21E

```
        GTGACTACCCCAACCCCAAATGCCACCGGCCCTACTGTGGGAGAAACAAGTCCACAGGCA
4201    ---------+---------+---------+---------+---------+---------+    4260
        ValThrThrProThrProAsnAlaThrGlyProThrValGlyGluThrSerProGlnAla

AATGCCACCAACCACACCTTAGGAGGAACAAGTCCCACCCCAGTAGTTACCAGCCAACCA
4261    ---------+---------+---------+---------+---------+---------+    4320
        AsnAlaThrAsnHisThrLeuGlyGlyThrSerProThrProValValThrSerGlnPro

AAAAATGCAACCAGTGCTGTTACCACAGGCCAACATAACATAACTTCAAGTTCAACCTCT
4321    ---------+---------+---------+---------+---------+---------+    4380
        LysAsnAlaThrSerAlaValThrThrGlyGlnHisAsnIleThrSerSerSerThrSer

TCCATGTCACTGAGACCCAGTTCAAACCCAGAGACACTCAGCCCCTCCACCAGTGACAAT
4381    ---------+---------+---------+---------+---------+---------+    4440
        SerMetSerLeuArgProSerSerAsnProGluThrLeuSerProSerThrSerAspAsn

TCAACGTCACATATGCCTTTACTAACCTCCGCTCACCCAACAGGTGGTGAAAATATAACA
4441    ---------+---------+---------+---------+---------+---------+    4500
        SerThrSerHisMetProLeuLeuThrSerAlaHisProThrGlyGlyGluAsnIleThr

CAGGTGACACCAGCCTCTATCAGCACACATCATGTGTCCACCAGTTCGCCAGCACCCCGC
4501    ---------+---------+---------+---------+---------+---------+    4560
        GlnValThrProAlaSerIleSerThrHisHisValSerThrSerSerProAlaProArg

CCAGGCACCACCAGCCAAGCGTCAGGCCCTGGAAACAGTTCCACATCCACAAAACCGGGG
4561    ---------+---------+---------+---------+---------+---------+    4620
        ProGlyThrThrSerGlnAlaSerGlyProGlyAsnSerSerThrSerThrLysProGly

GAGGTTAATGTCACCAAAGGCACGCCCCCCCAAAATGCAACGTCGCCCCAGGCCCCCAGT
4621    ---------+---------+---------+---------+---------+---------+    4680
        GluValAsnValThrLysGlyThrProProGlnAsnAlaThrSerProGlnAlaProSer

GGCCAAAAGACGGCGGTTCCCACGGTCACCTCAACAGGTGGAAAGGCCAATTCTACCACC
4681    ---------+---------+---------+---------+---------+---------+    4740
        GlyGlnLysThrAlaValProThrValThrSerThrGlyGlyLysAlaAsnSerThrThr

GGTGGAAAGCACACCACAGGACATGGAGCCCGGACAAGTACAGAGCCCACCACAGATTAC
4741    ---------+---------+---------+---------+---------+---------+    4800
        GlyGlyLysHisThrThrGlyHisGlyAlaArgThrSerThrGluProThrThrAspTyr

GGCGGTGATTCAACTACGCCAAGACCGAGATACAATGCGACCACCTATCTACCTCCCAGC
4801    ---------+---------+---------+---------+---------+---------+    4860
        GlyGlyAspSerThrThrProArgProArgTyrAsnAlaThrThrTyrLeuProProSer

ACTTCTAGCAAACTGCGGCCCCGCTGGACTTTTACGAGCCCACCGGTTACCACAGCCCAA
4861    ---------+---------+---------+---------+---------+---------+    4920
        ThrSerSerLysLeuArgProArgTrpThrPheThrSerProProValThrThrAlaGln

GCCACCGTGCCAGTCCCGCCAACGTCCCAGCCCAGATTCTCAAACCTCTCCATGCTAGTA
4921    ---------+---------+---------+---------+---------+---------+    4980
        AlaThrValProValProProThrSerGlnProArgPheSerAsnLeuSerMetLeuVal

CTGCAGccaagcttATCGATGATAAGCTGTCAAACATGA
4981    ---------+---------+---------+---------    5019
        LeuGlnProSerLeuSerMetIleSerCysGlnThrEnd
```

FIG. 21F

```
ATGGAAACCACTCAGACTCTCCGCTTTAAGACCAAGGCCCTAGCCGTCCTGTCCAAGTGC
                                                                    60
TACCTTTGGTGAGTCTGAGAGGCGAAATTCTGGTTCCGGGATCGGCAGGACAGGTTCACG
Met Glu Thr Thr Gln Thr Leu Arg Phe Lys Thr Lys Ala Leu Ala Val Leu Ser Lys Cys

TATGACCATGCCCAGACTCATCTCAAGGGAGGAGTGCTGCAGGTAAACCTTCTGTCTGTA
                                                                    120
ATACTGGTACGGGTCTGAGTAGAGTTCCCTCCTCACGACGTCCATTTGGAAGACAGACAT
Tyr Asp His Ala Gln Thr His Leu Lys Gly Gly Val Leu Gln Val Asn Leu Leu Ser Val

AACTATGGAGGCCCCCGGCTGGCCGCCGTGGCCAACGCAGGCACGGCCGGGCTAATCAGC
                                                                    180
TTGATACCTCCGGGGGCCGACCGGCGGCACCGGTTGCGTCCGTGCCGGCCCGATTAGTCG
Asn Tyr Gly Gly Pro Arg Leu Ala Ala Val Ala Asn Ala Gly Thr Ala Gly Leu Ile Ser

TTCGAGGTCTCCCCTGACGCTGTGGCCGAGTGGCAGAATCACCAGGACCCAGAGGAGGCC
                                                                    240
AAGCTCCAGAGGGGACTGCGACACCGGCTCACCGTCTTAGTGGTCCTGGGTCTCCTCCGG
Phe Glu Val Ser Pro Asp Ala Val Ala Glu Trp Gln Asn His Gln Asp Pro Glu Glu Ala

CCGGCCGCCGTGTCATTTAGAAACCTTGCCTACGGGCGCACCTGTGTCCTGGGCAAGGAG
                                                                    300
GGCCGGCGGCACAGTAAATCTTTGGAACGGATGCCCGCGTGGACACAGGACCCGTTCCTC
Pro Ala Ala Val Ser Phe Arg Asn Leu Ala Tyr Gly Arg Thr Cys Val Leu Gly Lys Glu

CTGTTTGGCTCGGCTGTGGAGCAGGCTTCCCTGCAATTTTACAAGCGGCCACAAGGGGGT
                                                                    360
GACAAACCGAGCCGACACCTCGTCCGAAGGGACGTTAAAATGTTCGCCGGTGTTCCCCCA
Leu Phe Gly Ser Ala Val Glu Gln Ala Ser Leu Gln Phe Tyr Lys Arg Pro Gln Gly Gly

TCCCGGCCTGAATTTGTTAAGCTCACTATGGAATATGATGATAAGGTGTCCAAGAGCCAC
                                                                    420
AGGGCCGGACTTAAACAATTCGAGTGATACCTTATACTACTATTCCACAGGTTCTCGGTG
Ser Arg Pro Glu Phe Val Lys Leu Thr Met Glu Tyr Asp Asp Lys Val Ser Lys Ser His
```

FIG. 28A-1

```
CACACCTGCGCCCTGATGCCCTATATGCCCCCGGCCAGCGACAGGCTGAGGACCGAGCAG
------+---------+---------+---------+---------+---------+  480
GTGTGGACGCGGGACTACGGGATATACGGGGGCCGGTCGCTGTCCGACTCCTGGCTCGTC
 His Thr Cys Ala Leu Met Pro Tyr Met Pro Pro Ala Ser Asp Arg Leu Arg Thr Glu Gln

ATGATTGGGCAGGTGCTGTTGATGCCCAAGACGGCTTCCTCGTTGCAGAAGTGGGCACGC
------+---------+---------+---------+---------+---------+  540
TACTAACCCGTCCACGACAACTACGGGTTCTGCCGAAGGAGCAACGTCTTCACCCGTGCG
 Met Ile Gly Gln Val Leu Leu Met Pro Lys Thr Ala Ser Ser Leu Gln Lys Trp Ala Arg

CAGCAAGGCTCAGGCGGCGTTAAGGTGACACTCAATCCGGATATATACGTCACCACGTAT
------+---------+---------+---------+---------+---------+  600
GTCGTTCCGAGTCCGCCGCAATTCCACTGTGAGTTAGGCCTATATATGCAGTGGTGCATA
 Gln Gln Gly Ser Gly Gly Val Lys Val Thr Leu Asn Pro Asp Ile Tyr Val Thr Thr Tyr

ACTTCTGGGGAGGCCTGCCTCACCCTAGACTACAAGCCTCTGAGTGTGGGGCCATACGAG
------+---------+---------+---------+---------+---------+  660
TGAAGACCCCTCCGGACGGAGTGGGATCTGATGTTCGGAGACTCACACCCCGGTATGCTC
 Thr Ser Gly Glu Ala Cys Leu Thr Leu Asp Tyr Lys Pro Leu Ser Val Gly Pro Tyr Glu

GCCTTCACTGGCCCTGTGGCCAAGGCTCAGGACGTGGGGGCCGTTGAGGCCCACGTTGTC
------+---------+---------+---------+---------+---------+  720
CGGAAGTGACCGGGACACCGGTTCCGAGTCCTGCACCCCCGGCAACTCCGGGTGCAACAG
 Ala Phe Thr Gly Pro Val Ala Lys Ala Gln Asp Val Gly Ala Val Glu Ala His Val Val

TGCTCGGTAGCAGCGGACTCGCTGGCGGCGGCGCTTAGCCTCTGCCGCATTCCGGCCGTT
------+---------+---------+---------+---------+---------+  780
ACGAGCCATCGTCGCCTGAGCGACCGCCGCCGCGAATCGGAGACGGCGTAAGGCCGGCAA
 Cys Ser Val Ala Ala Asp Ser Leu Ala Ala Ala Leu Ser Leu Cys Arg Ile Pro Ala Val

AGCGTGCCAATCTTGAGGTTTTACAGGTCTGGCATCATAGCTGTGGTGGCCGGCCTGCTG
------+---------+---------+---------+---------+---------+  840
TCGCACGGTTAGAACTCCAAAATGTCCAGACCGTAGTATCGACACCACCGGCCGGACGAC
 Ser Val Pro Ile Leu Arg Phe Tyr Arg Ser Gly Ile Ile Ala Val Val Ala Gly Leu Leu
```

FIG. 28A-2

```
ACGTCAGCGGGGGACCTGCCGTTGGATCTTAGTGTTATTTTATTTAACCACGCCTCCGAA
                                                              900
TGCAGTCGCCCCCTGGACGGCAACCTAGAATCACAATAAAATAAATTGGTGCGGAGGCTT
Thr Ser Ala Gly Asp Leu Pro Leu Asp Leu Ser Val Ile Leu Phe Asn His Ala Ser Glu

GAGGCGGCCGCCAGTACGGCCTCTGAGCCAGAAGATAAAAGTCCCCGGGTGCAACCACTG
                                                              960
CTCCGCCGGCGGTCATGCCGGAGACTCGGTCTTCTATTTTCAGGGGCCCACGTTGGTGAC
Glu Ala Ala Ala Ser Thr Ala Ser Glu Pro Glu Asp Lys Ser Pro Arg Val Gln Pro Leu

GGCACAGGACTCCAACAACGCCCCAGACATACGGTCAGTCCATCTCCTTCACCTCCGCCA
                                                              1020
CCGTGTCCTGAGGTTGTTGCGGGGTCTGTATGCCAGTCAGGTAGAGGAAGTGGAGGCGGT
Gly Thr Gly Leu Gln Gln Arg Pro Arg His Thr Val Ser Pro Ser Pro Ser Pro Pro

CCTCCTAGGACCCCTACTTGGGAGAGTCCGGCAAGGCCAGAGACACCCTCGCCTGCCATT
                                                              1080
GGAGGATCCTGGGGATGAACCCTCTCAGGCCGTTCCGGTCTCTGTGGGAGCGGACGGTAA
Pro Pro Arg Thr Pro Thr Trp Glu Ser Pro Ala Arg Pro Glu Thr Pro Ser Pro Ala Ile

CCCAGCCACTCCAGCAACACCGCACTGGAGAGGCCTCTGGCTGTTCAGCTCGCGAGGAAA
                                                              1140
GGGTCGGTGAGGTCGTTGTGGCGTGACCTCTCCGGAGACCGACAAGTCGAGCGCTCCTTT
Pro Ser His Ser Ser Asn Thr Ala Leu Glu Arg Pro Leu Ala Val Gln Leu Ala Arg Lys

AGGACATCGTCGGAGGCCAGGCAGAAGCAGAAGCACCCCAAGAAAGTGAAGCAGGCCTTT
                                                              1200
TCCTGTAGCAGCCTCCGGTCCGTCTTCGTCTTCGTGGGGTTCTTTCACTTCGTCCGGAAA
Arg Thr Ser Ser Glu Ala Arg Gln Lys Gln Lys His Pro Lys Lys Val Lys Gln Ala Phe

AACCCCCTCATT
─────┼─────┼─► 1212
TTGGGGGAGTAA
Asn Pro Leu Ile
```

FIG. 28A-3

```
ATGGCAACGACCAGTCATGTCGAGCATGAGCTCCTCTCCAAATTGATTGATGAGTTAAAG
                                                             60
TACCGTTGCTGGTCAGTACAGCTCGTACTCGAGGAGAGGTTTAACTAACTACTCAATTTC
Met Ala Thr Thr Ser His Val Glu His Glu Leu Leu Ser Lys Leu Ile Asp Glu Leu Lys

GTCAAGGCCAACTCAGACCCCGAGGCTGATGTCCTGGCCGGGCGCCTGCTCCACCGCCTT
                                                             120
CAGTTCCGGTTGAGTCTGGGGCTCCGACTACAGGACCGGCCCGCGGACGAGGTGGCGGAA
Val Lys Ala Asn Ser Asp Pro Glu Ala Asp Val Leu Ala Gly Arg Leu Leu His Arg Leu

AAGGCCGAGTCAGTTACACACACAGTAGCCGAATATCTGGAGGTCTTCTCTGACAAATTC
                                                             180
TTCCGGCTCAGTCAATGTGTGTGTCATCGGCTTATAGACCTCCAGAAGAGACTGTTTAAG
Lys Ala Glu Ser Val Thr His Thr Val Ala Glu Tyr Leu Glu Val Phe Ser Asp Lys Phe

TACGATGAGGAATTCTTCCAGATGCACCGGGATGAGCTGGAGACCCGAGTCTCTGCTTTC
                                                             240
ATGCTACTCCTTAAGAAGGTCTACGTGGCCCTACTCGACCTCTGGGCTCAGAGACGAAAG
Tyr Asp Glu Glu Phe Phe Gln Met His Arg Asp Glu Leu Glu Thr Arg Val Ser Ala Phe

GCGCAGAGCCCGGCCTACGAGCGCATCGTCTCCAGCGGCTACCTGTCGGCCCTGCGCTAC
                                                             300
CGCGTCTCGGGCCGGATGCTCGCGTAGCAGAGGTCGCCGATGGACAGCCGGGACGCGATG
Ala Gln Ser Pro Ala Tyr Glu Arg Ile Val Ser Ser Gly Tyr Leu Ser Ala Leu Arg Tyr

TATGACACCTATCTGTATGTGGGGCGCAGCGGGAAGCAGGAGAGTGTGCAGCACTTTTAC
                                                             360
ATACTGTGGATAGACATACACCCCGCGTCGCCCTTCGTCCTCTCACACGTCGTGAAAATG
Tyr Asp Thr Tyr Leu Tyr Val Gly Arg Ser Gly Lys Gln Glu Ser Val Gln His Phe Tyr

ATGCGGTTAGCCGGCTTCTGTGCCTCAACCACCTGCCTCTACGCGGGTCTCAGGGCAGCC
                                                             420
TACGCCAATCGGCCGAAGACACGGAGTTGGTGGACGGAGATGCGCCCAGAGTCCCGTCGG
Met Arg Leu Ala Gly Phe Cys Ala Ser Thr Thr Cys Leu Tyr Ala Gly Leu Arg Ala Ala
```

FIG. 28B-1

```
CTGCAGCGGGCCAGGCCGGAGATTGAGAGTGACATGGAGGTGTTTGATTACTACTTTGAG
                                                              480
GACGTCGCCCGGTCCGGCCTCTAACTCTCACTGTACCTCCACAAACTAATGATGAAACTC

Leu Gln Arg Ala Arg Pro Glu Ile Glu Ser Asp Met Glu Val Phe Asp Tyr Tyr Phe Glu

CACCTAACCTCCCAGACGGTGTGCTGCTCCACGCCCTTTATGCGCTTTGCCGGGGTGGAA
                                                              540
GTGGATTGGAGGGTCTGCCACACGACGAGGTGCGGGAAATACGCGAAACGGCCCCACCTT

His Leu Thr Ser Gln Thr Val Cys Cys Ser Thr Pro Phe Met Arg Phe Ala Gly Val Glu

AACTCCACTCTGGCCAGCTGCATCCTCACCACCCCCGACCTCAGCTCCGAGTGGGACGTG
                                                              600
TTGAGGTGAGACCGGTCGACGTAGGAGTGGTGGGGGCTGGAGTCGAGGCTCACCCTGCAC

Asn Ser Thr Leu Ala Ser Cys Ile Leu Thr Thr Pro Asp Leu Ser Ser Glu Trp Asp Val

ACCCAGGCCCTCTATAGGCACCTGGGGCGCTACCTCTTTCAGCGAGCCGGGGTGGGTGTA
                                                              660
TGGGTCCGGGAGATATCCGTGGACCCCGCGATGGAGAAAGTCGCTCGGCCCCACCCACAT

Thr Gln Ala Leu Tyr Arg His Leu Gly Arg Tyr Leu Phe Gln Arg Ala Gly Val Gly Val

GGGGTGACGGGGGCTGGCCAGGATGGGAAACACATCAGCCTCCTGATGAGGATGATCAAC
                                                              720
CCCCACTGCCCCCGACCGGTCCTACCCTTTGTGTAGTCGGAGGACTACTCCTACTAGTTG

Gly Val Thr Gly Ala Gly Gln Asp Gly Lys His Ile Ser Leu Leu Met Arg Met Ile Asn

AGCCACGTGGAGTACCACAACTATGGCTGCAAGAGGCCGGTCAGTGTGGCGGCCTACATG
                                                              780
TCGGTGCACCTCATGGTGTTGATACCGACGTTCTCCGGCCAGTCACACCGCCGGATGTAC

Ser His Val Glu Tyr His Asn Tyr Gly Cys Lys Arg Pro Val Ser Val Ala Ala Tyr Met

GAGCCCTGGCACAGCCAGATTTTCAAGTTTTTGGAAACGAAGCTGCCGGAGAACCACGAG
                                                              840
CTCGGGACCGTGTCGGTCTAAAAGTTCAAAAACCTTTGCTTCGACGGCCTCTTGGTGCTC

Glu Pro Trp His Ser Gln Ile Phe Lys Phe Leu Glu Thr Lys Leu Pro Glu Asn His Glu
```

FIG. 28B-2

```
AGGTGCCCGGGCATCTTTACGGGGCTCTTTGTCCCCGAGCTCTTCTTCAAGCTTTTTAGG
------+----+----+----+----+----+----+----+----+----+----+----+  900
TCCACGGGCCCGTAGAAATGCCCCGAGAAACAGGGGCTCGAGAAGAAGTTCGAAAAATCC
```
Arg Cys Pro Gly Ile Phe Thr Gly Leu Phe Val Pro Glu Leu Phe Phe Lys Leu Phe Arg

```
GACACGCCCTGGTCGGACTGGTACCTGTTTGACCCCAAGGACGCCGGGGACCTGGAGAGG
------+----+----+----+----+----+----+----+----+----+----+----+  960
CTGTGCGGGACCAGCCTGACCATGGACAAACTGGGGTTCCTGCGGCCCCTGGACCTCTCC
```
Asp Thr Pro Trp Ser Asp Trp Tyr Leu Phe Asp Pro Lys Asp Ala Gly Asp Leu Glu Arg

```
CTCTACGGGGAGGAGTTTGAGCGCGAGTACTATCGGCTGGTGACAGCGGGCAAGTTTTGT
------+----+----+----+----+----+----+----+----+----+----+----+  1020
GAGATGCCCCTCCTCAAACTCGCGCTCATGATAGCCGACCACTGTCGCCCGTTCAAAACA
```
Leu Tyr Gly Glu Glu Phe Glu Arg Glu Tyr Tyr Arg Leu Val Thr Ala Gly Lys Phe Cys

```
GGGCGGGTCTCCATCAAGTCCCTGATGTTCTCTATCGTCAACTGCGCCGTCAAGGCCGGC
------+----+----+----+----+----+----+----+----+----+----+----+  1080
CCCGCCCAGAGGTAGTTCAGGGACTACAAGAGATAGCAGTTGACGCGGCAGTTCCGGCCG
```
Gly Arg Val Ser Ile Lys Ser Leu Met Phe Ser Ile Val Asn Cys Ala Val Lys Ala Gly

```
AGCCCCTTCATCCTTTTGAAGGAGGCCTGCAACGCCCACTTTTGGCGCGACCTGCAGGGC
------+----+----+----+----+----+----+----+----+----+----+----+  1140
TCGGGGAAGTAGGAAAACTTCCTCCGGACGTTGCGGGTGAAAACCGCGCTGGACGTCCCG
```
Ser Pro Phe Ile Leu Leu Lys Glu Ala Cys Asn Ala His Phe Trp Arg Asp Leu Gln Gly

```
GAGGCCATGAACGCCGCCAACCTGTGCGCCGAGGTGCTGCAGCCCTCGAGGAAGTCTGTG
------+----+----+----+----+----+----+----+----+----+----+----+  1200
CTCCGGTACTTGCGGCGGTTGGACACGCGGCTCCACGACGTCGGGAGCTCCTTCAGACAC
```
Glu Ala Met Asn Ala Ala Asn Leu Cys Ala Glu Val Leu Gln Pro Ser Arg Lys Ser Val

```
GCCACCTGCAATCTGGCCAACATCTGCCTCCCGCGCTGCCTGGTGAATGCGCCTCTGGCG
------+----+----+----+----+----+----+----+----+----+----+----+  1260
CGGTGGACGTTAGACCGGTTGTAGACGGAGGGCGCGACGGACCACTTACGCGGAGACCGC
```
Ala Thr Cys Asn Leu Ala Asn Ile Cys Leu Pro Arg Cys Leu Val Asn Ala Pro Leu Ala

FIG. 28B-3

```
GTGCGGGCACAGCGGGCCGACACGCAGGGGGATGAACTCCTGCTGGCCCTCCCTCGACTC
------+----+----+----+----+----+----+----+----+----+----+----+  1320
CACGCCCGTGTCGCCCGGCTGTGCGTCCCCCTACTTGAGGACGACCGGGAGGGAGCTGAG

Val Arg Ala Gln Arg Ala Asp Thr Gln Gly Asp Glu Leu Leu Leu Ala Leu Pro Arg Leu
```

```
TCAGTCACCCTACCTGGAGAGGGGGCAGTCGGTGATGGATTCTCGCTAGCCCGCCTCAGA
------+----+----+----+----+----+----+----+----+----+----+----+  1380
AGTCAGTGGGATGGACCTCTCCCCCGTCAGCCACTACCTAAGAGCGATCGGGCGGAGTCT

Ser Val Thr Leu Pro Gly Glu Gly Ala Val Gly Asp Gly Phe Ser Leu Ala Arg Leu Arg
```

```
GATGCCACCCAGTGTGCCACCTTTGTGGTGGCCTGCTCCATTCTTCAGGGATCCCCCACT
------+----+----+----+----+----+----+----+----+----+----+----+  1440
CTACGGTGGGTCACACGGTGGAAACACCACCGGACGAGGTAAGAAGTCCCTAGGGGGTGA

Asp Ala Thr Gln Cys Ala Thr Phe Val Val Ala Cys Ser Ile Leu Gln Gly Ser Pro Thr
```

```
TATGATTCCAGGGATATGGCCTCCATGGGCCTCGGGGTGCAGGGCCTGGCCGATGTCTTT
------+----+----+----+----+----+----+----+----+----+----+----+  1500
ATACTAAGGTCCCTATACCGGAGGTACCCGGAGCCCCACGTCCCGGACCGGCTACAGAAA

Tyr Asp Ser Arg Asp Met Ala Ser Met Gly Leu Gly Val Gln Gly Leu Ala Asp Val Phe
```

```
GCGGACCTGGGCTGGCAGTACACTGACCCTCCCTCTCGCTCGTTAAACAAGGAAATATTC
------+----+----+----+----+----+----+----+----+----+----+----+  1560
CGCCTGGACCCGACCGTCATGTGACTGGGAGGGAGAGCGAGCAATTTGTTCCTTTATAAG

Ala Asp Leu Gly Trp Gln Tyr Thr Asp Pro Pro Ser Arg Ser Leu Asn Lys Glu Ile Phe
```

```
GAACATATGTACTTTACGGCCCTCTGCACCAGTAGTCTGATTGGACTTCACACCAGGAAG
------+----+----+----+----+----+----+----+----+----+----+----+  1620
CTTGTATACATGAAATGCCGGGAGACGTGGTCATCAGACTAACCTGAAGTGTGGTCCTTC

Glu His Met Tyr Phe Thr Ala Leu Cys Thr Ser Ser Leu Ile Gly Leu His Thr Arg Lys
```

```
ATTTTTCCGGGTTTCAAACAGAGCAAGTATGCCGGGGGGTGGTTTCACTGGCACGATTGG
------+----+----+----+----+----+----+----+----+----+----+----+  1680
TAAAAAGGCCCAAAGTTTGTCTCGTTCATACGGCCCCCCACCAAAGTGACCGTGCTAACC

Ile Phe Pro Gly Phe Lys Gln Ser Lys Tyr Ala Gly Gly Trp Phe His Trp His Asp Trp
```

FIG. 28B-4

```
GCAGGAACAGACCTTTCTATTCCCAGGGAAATTTGGTCTCGCCTCTCTGAACGCATTGTG
────┼────┼────┼────┼────┼────┼────┼────┼────┼────┼────┼────+ 1740
CGTCCTTGTCTGGAAAGATAAGGGTCCCTTTAAACCAGAGCGGAGAGACTTGCGTAACAC
Ala Gly Thr Asp Leu Ser Ile Pro Arg Glu Ile Trp Ser Arg Leu Ser Glu Arg Ile Val

AGGGATGGGCTTTTCAATTCACAGTTTATCGCCCTGATGCCCACCTCAGGCTGTGCCCAG
────┼────┼────┼────┼────┼────┼────┼────┼────┼────┼────┼────+ 1800
TCCCTACCCGAAAAGTTAAGTGTCAAATAGCGGGACTACGGGTGGAGTCCGACACGGGTC
Arg Asp Gly Leu Phe Asn Ser Gln Phe Ile Ala Leu Met Pro Thr Ser Gly Cys Ala Gln

GTGACGGGCTGTTCGGACGCCTTCTACCCCTTCTATGCCAATGCGTCCACCAAGGTCACC
────┼────┼────┼────┼────┼────┼────┼────┼────┼────┼────┼────+ 1860
CACTGCCCGACAAGCCTGCGGAAGATGGGGAAGATACGGTTACGCAGGTGGTTCCAGTGG
Val Thr Gly Cys Ser Asp Ala Phe Tyr Pro Phe Tyr Ala Asn Ala Ser Thr Lys Val Thr

AACAAGGAGGAGGCCCTTAGGCCAAACCGGTCTTTTTGGCGTCATGTGCGTCTGGATGAC
────┼────┼────┼────┼────┼────┼────┼────┼────┼────┼────┼────+ 1920
TTGTTCCTCCTCCGGGAATCCGGTTTGGCCAGAAAAACCGCAGTACACGCAGACCTACTG
Asn Lys Glu Glu Ala Leu Arg Pro Asn Arg Ser Phe Trp Arg His Val Arg Leu Asp Asp

AGGGAAGCTTTGAATCTTGTCGGGGGCCGTGTCTCCTGCCTCCCGGAGGCTCTGCGGCAG
────┼────┼────┼────┼────┼────┼────┼────┼────┼────┼────┼────+ 1980
TCCCTTCGAAACTTAGAACAGCCCCCGGCACAGAGGACGGAGGGCCTCCGAGACGCCGTC
Arg Glu Ala Leu Asn Leu Val Gly Gly Arg Val Ser Cys Leu Pro Glu Ala Leu Arg Gln

CGCTACCTGCGTTTCCAAACGGCCTTTGATTACAACCAGGAGGACCTGATTCAGATGTCC
────┼────┼────┼────┼────┼────┼────┼────┼────┼────┼────┼────+ 2040
GCGATGGACGCAAAGGTTTGCCGGAAACTAATGTTGGTCCTCCTGGACTAAGTCTACAGG
Arg Tyr Leu Arg Phe Gln Thr Ala Phe Asp Tyr Asn Gln Glu Asp Leu Ile Gln Met Ser

CGGGACAGGGCCCCCTTTGTGGACCAGAGCCAATCTCACAGCCTGTTTTTGCGTGAGGAA
────┼────┼────┼────┼────┼────┼────┼────┼────┼────┼────┼────+ 2100
GCCCTGTCCCGGGGGAAACACCTGGTCTCGGTTAGAGTGTCGGACAAAAACGCACTCCTT
Arg Asp Arg Ala Pro Phe Val Asp Gln Ser Gln Ser His Ser Leu Phe Leu Arg Glu Glu
```

FIG. 28B-5

```
GATGCCGCGCGGGCCAGCACGCTAGCCAACCTACTGGTGCGCAGCTACGAGCTGGGCCTG
------+----+----+----+----+----+----+----+----+----+----+----+  2160
CTACGGCGCGCCCGGTCGTGCGATCGGTTGGATGACCACGCGTCGATGCTCGACCCGGAC
```
Asp Ala Ala Arg Ala Ser Thr Leu Ala Asn Leu Leu Val Arg Ser Tyr Glu Leu Gly Leu

```
AAGACTATCATGTACTATTGTCGCATTGAGAAGGCCGCCGATCTGGGGGTGATGGAGTGT
------+----+----+----+----+----+----+----+----+----+----+----+  2220
TTCTGATAGTACATGATAACAGCGTAACTCTTCCGGCGGCTAGACCCCCACTACCTCACA
```
Lys Thr Ile Met Tyr Tyr Cys Arg Ile Glu Lys Ala Ala Asp Leu Gly Val Met Glu Cys

```
AAGGCCAGCGCGGCTCTGTCGGTGCCGCGGGAGGAACAGAATGAGCGGAGTCCCGCTGAG
------+----+----+----+----+----+----+----+----+----+----+----+  2280
TTCCGGTCGCGCCGAGACAGCCACGGCGCCCTCCTTGTCTTACTCGCCTCAGGGCGACTC
```
Lys Ala Ser Ala Ala Leu Ser Val Pro Arg Glu Glu Gln Asn Glu Arg Ser Pro Ala Glu

```
CAGATGCCGCCTCGTCCCATGGAACCGGCGCAGGTTGCGGGGCCGGTTGACATCATGAGC
------+----+----+----+----+----+----+----+----+----+----+----+  2340
GTCTACGGCGGAGCAGGGTACCTTGGCCGCGTCCAACGCCCCGGCCAACTGTAGTACTCG
```
Gln Met Pro Pro Arg Pro Met Glu Pro Ala Gln Val Ala Gly Pro Val Asp Ile Met Ser

```
AAGGGCCCAGGGGAGGGACCAGGTGGGTGGTGTGTGCCCGGGGGATTGGAAGTGTGCTAT
------+----+----+----+----+----+----+----+----+----+----+----+  2400
TTCCCGGGTCCCCTCCCTGGTCCACCCACCACACACGGGCCCCCTAACCTTCACACGATA
```
Lys Gly Pro Gly Glu Gly Pro Gly Gly Trp Cys Val Pro Gly Gly Leu Glu Val Cys Tyr

```
AAGTACCGTCAGCTCTTCTCAGAGGATGATCTGTTGGAGACTGACGGTTTTACTGAACGA
------+----+----+----+----+----+----+----+----+----+----+----+  2460
TTCATGGCAGTCGAGAAGAGTCTCCTACTAGACAACCTCTGACTGCCAAAATGACTTGCT
```
Lys Tyr Arg Gln Leu Phe Ser Glu Asp Asp Leu Leu Glu Thr Asp Gly Phe Thr Glu Arg

```
GCCTGTGAATCTTGCCAA
------+----+-----→  2478
CGGACACTTAGAACGGTT
```
Ala Cys Glu Ser Cys Gln

FIG. 28B-6

```
ATGGAAGAGAGGGGCAGGGAAACGCAAATGCCGGTTGCCCGGTATGGGGGCCCGTTTATT
                                                              60
TACCTTCTCTCCCCGTCCCTTTGCGTTTACGGCCAACGGGCCATACCCCCGGGCAAATAA
Met Glu Glu Arg Gly Arg Glu Thr Gln Met Pro Val Ala Arg Tyr Gly Gly Pro Phe Ile

ATGGTAAGGCTCTTCGGGCAAGATGGAGAGGCAAACATACAGGAGGAAAGGCTATATGAG
                                                              120
TACCATTCCGAGAAGCCCGTTCTACCTCTCCGTTTGTATGTCCTCCTTTCCGATATACTC
Met Val Arg Leu Phe Gly Gln Asp Gly Glu Ala Asn Ile Gln Glu Glu Arg Leu Tyr Glu

CTACTCTCTGACCCACGCTCCGCGCTCGGCCTAGACCCGGGGCCCCTGATTGCTGAGAAC
                                                              180
GATGAGAGACTGGGTGCGAGGCGCGAGCCGGATCTGGGCCCCGGGGACTAACGACTCTTG
Leu Leu Ser Asp Pro Arg Ser Ala Leu Gly Leu Asp Pro Gly Pro Leu Ile Ala Glu Asn

CTGCTGCTAGTGGCGCTGCGTGGCACCAACAACGATCCCAGGCCTCAGCGTCAGGAGAGG
                                                              240
GACGACGATCACCGCGACGCACCGTGGTTGTTGCTAGGGTCCGGAGTCGCAGTCCTCTCC
Leu Leu Leu Val Ala Leu Arg Gly Thr Asn Asn Asp Pro Arg Pro Gln Arg Gln Glu Arg

GCCAGAGAACTGGCCCTCGTTGGCATTCTACTAGGAAACGGCGAGCAGGGTGAACACTTG
                                                              300
CGGTCTCTTGACCGGGAGCAACCGTAAGATGATCCTTTGCCGCTCGTCCCACTTGTGAAC
Ala Arg Glu Leu Ala Leu Val Gly Ile Leu Leu Gly Asn Gly Glu Gln Gly Glu His Leu

GGCACGGAGAGTGCCCTGGAGGCCTCAGGCAACAACTATGTGTATGCCTACGGACCAGAC
                                                              360
CCGTGCCTCTCACGGGACCTCCGGAGTCCGTTGTTGATACACATACGGATGCCTGGTCTG
Gly Thr Glu Ser Ala Leu Glu Ala Ser Gly Asn Asn Tyr Val Tyr Ala Tyr Gly Pro Asp

TGGATGGCAAGGCCTTCCACATGGTCCGCGGAAATCCAGCAATTCCTGCGACTCCTGGGC
                                                              420
ACCTACCGTTCCGGAAGGTGTACCAGGCGCCTTTAGGTCGTTAAGGACGCTGAGGACCCG
Trp Met Ala Arg Pro Ser Thr Trp Ser Ala Glu Ile Gln Gln Phe Leu Arg Leu Leu Gly
```

FIG. 28C-1

```
GCCACGTACGTGCTTCGCGTGGAGATGGGCAGGCAGTTTGGCTTCGAGGTGCATAGAAGC
------+------+------+------+------+------+------+------+------+------+ 480
CGGTGCATGCACGAAGCGCACCTCTACCCGTCCGTCAAACCGAAGCTCCACGTATCTTCG
 Ala Thr Tyr Val Leu Arg Val Glu Met Gly Arg Gln Phe Gly Phe Glu Val His Arg Ser

CGGCCCTCCTTCCGTCAGTTCCAGGCCATCAATCACCTTGTCCTGTTTGACAACGCCCTT
------+------+------+------+------+------+------+------+------+------+ 540
GCCGGGAGGAAGGCAGTCAAGGTCCGGTAGTTAGTGGAACAGGACAAACTGTTGCGGGAA
 Arg Pro Ser Phe Arg Gln Phe Gln Ala Ile Asn His Leu Val Leu Phe Asp Asn Ala Leu

CGCAAGTACGATTCCGGCCAGGTGGCGGCGGGCTTCCAGAGGGCCCTTCTGGTGGCCGGG
------+------+------+------+------+------+------+------+------+------+ 600
GCGTTCATGCTAAGGCCGGTCCACCGCCGCCCGAAGGTCTCCCGGGAAGACCACCGGCCC
 Arg Lys Tyr Asp Ser Gly Gln Val Ala Ala Gly Phe Gln Arg Ala Leu Leu Val Ala Gly

CCAGAGACCGCTGACACGAGGCCGGACCTCCGCAAGCTGAATGAGTGGGTGTTTGGTGGC
------+------+------+------+------+------+------+------+------+------+ 660
GGTCTCTGGCGACTGTGCTCCGGCCTGGAGGCGTTCGACTTACTCACCCACAAACCACCG
 Pro Glu Thr Ala Asp Thr Arg Pro Asp Leu Arg Lys Leu Asn Glu Trp Val Phe Gly Gly

AGGGCTGCTGGTGGCAGACAGCTGGCCGACGAGCTAAAGATCGTGTCCGCGCTGCGAGAC
------+------+------+------+------+------+------+------+------+------+ 720
TCCCGACGACCACCGTCTGTCGACCGGCTGCTCGATTTCTAGCACAGGCGCGACGCTCTG
 Arg Ala Ala Gly Gly Arg Gln Leu Ala Asp Glu Leu Lys Ile Val Ser Ala Leu Arg Asp

ACTTACTCGGGCCACTTGGTCCTTCAGCCCACGGAGACCCTTGACACATGGAAGGTGTTG
------+------+------+------+------+------+------+------+------+------+ 780
TGAATGAGCCCGGTGAACCAGGAAGTCGGGTGCCTCTGGGAACTGTGTACCTTCCACAAC
 Thr Tyr Ser Gly His Leu Val Leu Gln Pro Thr Glu Thr Leu Asp Thr Trp Lys Val Leu

AGCAGGGACACACGAACCGCTCATAGTTTGGAGCACGGATTCATTCATGCCGCGGGGACC
------+------+------+------+------+------+------+------+------+------+ 840
TCGTCCCTGTGTGCTTGGCGAGTATCAAACCTCGTGCCTAAGTAAGTACGGCGCCCCTGG
 Ser Arg Asp Thr Arg Thr Ala His Ser Leu Glu His Gly Phe Ile His Ala Ala Gly Thr
```

FIG. 28C-2

```
ATCCAGGCCAACTGCCCACAGCTGTTTATGAGACGCCAGCACCCCGGCCTCTTTCCCTTC
------+----+----+----+----+----+----+----+----+----+----+----+ 900
TAGGTCCGGTTGACGGGTGTCGACAAATACTCTGCGGTCGTGGGGCCGGAGAAAGGGAAG

Ile Gln Ala Asn Cys Pro Gln Leu Phe Met Arg Arg Gln His Pro Gly Leu Phe Pro Phe

GTTAATGCAATAGCATCATCGCTGGGCTGGTACTACCAGACCGCCACCGGCCCCGGAGCA
------+----+----+----+----+----+----+----+----+----+----+----+ 960
CAATTACGTTATCGTAGTAGCGACCCGACCATGATGGTCTGGCGGTGGCCGGGGCCTCGT

Val Asn Ala Ile Ala Ser Ser Leu Gly Trp Tyr Tyr Gln Thr Ala Thr Gly Pro Gly Ala

GATGCCAGGGCGGCGGCCCGGCGCCAACAGGCCTTTCAGACCAGGGCGGCGGCTGAATGC
------+----+----+----+----+----+----+----+----+----+----+----+ 1020
CTACGGTCCCGCCGCCGGGCCGCGGTTGTCCGGAAAGTCTGGTCCCGCCGCCGACTTACG

Asp Ala Arg Ala Ala Arg Arg Gln Gln Ala Phe Gln Thr Arg Ala Ala Ala Glu Cys

CATGCCAAAAGCGGGGTGCCGGTCGTGGCCGGCTTCTACAGGACCATCAACGCCACGCTC
------+----+----+----+----+----+----+----+----+----+----+----+ 1080
GTACGGTTTTCGCCCCACGGCCAGCACCGGCCGAAGATGTCCTGGTAGTTGCGGTGCGAG

His Ala Lys Ser Gly Val Pro Val Val Ala Gly Phe Tyr Arg Thr Ile Asn Ala Thr Leu

AAGGGAGGAGAGGGCCTACAGCCCACTATGTTTAACGGGGAGCTGGGGGCCATCAAGCAC
------+----+----+----+----+----+----+----+----+----+----+----+ 1140
TTCCCTCCTCTCCCGGATGTCGGGTGATACAAATTGCCCCTCGACCCCCGGTAGTTCGTG

Lys Gly Gly Glu Gly Leu Gln Pro Thr Met Phe Asn Gly Glu Leu Gly Ala Ile Lys His

CAGGCACTTGACACTGTGAGGTATGACTACGGCCACTATCTCATAATGTTGGGGCCATTC
------+----+----+----+----+----+----+----+----+----+----+----+ 1200
GTCCGTGAACTGTGACACTCCATACTGATGCCGGTGATAGAGTATTACAACCCCGGTAAG

Gln Ala Leu Asp Thr Val Arg Tyr Asp Tyr Gly His Tyr Leu Ile Met Leu Gly Pro Phe

CAGCCATGGAGCGGACTGACGGCCCCTCCGTGCCCCTACGCCGAAAGTTCATGGGCACAG
------+----+----+----+----+----+----+----+----+----+----+----+ 1260
GTCGGTACCTCGCCTGACTGCCGGGGAGGCACGGGGATGCGGCTTTCAAGTACCCGTGTC

Gln Pro Trp Ser Gly Leu Thr Ala Pro Pro Cys Pro Tyr Ala Glu Ser Ser Trp Ala Gln
```

FIG. 28C-3

```
GCGGCCGTGCAGACGGCCCTCGAGCTGTTCTCGGCCCTGTACCCGGCCCCGTGCATCTCG
------------------------------------------------------------ 1320
CGCCGGCACGTCTGCCGGGAGCTCGACAAGAGCCGGGACATGGGCCGGGGCACGTAGAGC
 Ala Ala Val Gln Thr Ala Leu Glu Leu Phe Ser Ala Leu Tyr Pro Ala Pro Cys Ile Ser

GGCTACGCGCGCCCCCGGGCCCCAGTGCTGTGATCGAGCATCTGGGGTCCCTAGTTCCA
------------------------------------------------------------ 1380
CCGATGCGCGCGGGGGGCCCGGGGTCACGACACTAGCTCGTAGACCCCAGGGATCAAGGT
 Gly Tyr Ala Arg Pro Pro Gly Pro Ser Ala Val Ile Glu His Leu Gly Ser Leu Val Pro

AAGGGGGGTCTGCTGTTGTTTCTGTCTCACCTACCGGATGATGTTAAGGACGGGCTCGGA
------------------------------------------------------------ 1440
TTCCCCCCAGACGACAACAAAGACAGAGTGGATGGCCTACTACAATTCCTGCCCGAGCCT
 Lys Gly Gly Leu Leu Leu Phe Leu Ser His Leu Pro Asp Asp Val Lys Asp Gly Leu Gly

GAAATGGGGCCGGCCAGGGCCACGGGACCTGGAATGCAGCAGTTTGTCAGCAGCTACTTC
------------------------------------------------------------ 1500
CTTTACCCCGGCCGGTCCCGGTGCCCTGGACCTTACGTCGTCAAACAGTCGTCGATGAAG
 Glu Met Gly Pro Ala Arg Ala Thr Gly Pro Gly Met Gln Gln Phe Val Ser Ser Tyr Phe

CTCAACCCCGCCTGTTCCAACGTCTTCATTACAGTGAGGCAGCGAGGGGAGAAGATCAAC
------------------------------------------------------------ 1560
GAGTTGGGGCGGACAAGGTTGCAGAAGTAATGTCACTCCGTCGCTCCCCTCTTCTAGTTG
 Leu Asn Pro Ala Cys Ser Asn Val Phe Ile Thr Val Arg Gln Arg Gly Glu Lys Ile Asn

GGCCGTACCGTCCTCCAAGCGCTCGGACGCGCATGCGATATGGCAGGCTGCCAGCACTAT
------------------------------------------------------------ 1620
CCGGCATGGCAGGAGGTTCGCGAGCCTGCGCGTACGCTATACCGTCCGACGGTCGTGATA
 Gly Arg Thr Val Leu Gln Ala Leu Gly Arg Ala Cys Asp Met Ala Gly Cys Gln His Tyr

GTGCTGGGCTCCACGGTTCCCCTCGGTGGACTCAACTTTGTCAACGACCTGGCGTCCCCG
------------------------------------------------------------ 1680
CACGACCCGAGGTGCCAAGGGGAGCCACCTGAGTTGAAACAGTTGCTGGACCGCAGGGGC
 Val Leu Gly Ser Thr Val Pro Leu Gly Gly Leu Asn Phe Val Asn Asp Leu Ala Ser Pro
```

FIG. 28C-4

```
GTTCCACCGCCGAGATGATGGATGATTTCTCTCCCTTCTTCACCGTGGAGTTTCCCCCG
------+----+----+----+----+----+----+----+----+----+----+----+ 1740
CAAAGGTGGCGGCTCTACTACCTACTAAAGAGAGGGAAGAAGTGGCACCTCAAAGGGGGC

Val Ser Thr Ala Glu Met Met Asp Asp Phe Ser Pro Phe Phe Thr Val Glu Phe Pro Pro

ATTCAAGAGGAGGGCGCAAGTTCTCCGGTACCCTTAGATGTGGACGAGAGCATGGACATC
------+----+----+----+----+----+----+----+----+----+----+----+ 1800
TAAGTTCTCCTCCCGCGTTCAAGAGGCCATGGGAATCTACACCTGCTCTCGTACCTGTAG

Ile Gln Glu Glu Gly Ala Ser Ser Pro Val Pro Leu Asp Val Asp Glu Ser Met Asp Ile

TCTCCGTCTTACGAGTTGCCCTGGCTCTCGCTGGAGTCATGCCTCACAAGCATCCTGTCA
------+----+----+----+----+----+----+----+----+----+----+----+ 1860
AGAGGCAGAATGCTCAACGGGACCGAGAGCGACCTCAGTACGGAGTGTTCGTAGGACAGT

Ser Pro Ser Tyr Glu Leu Pro Trp Leu Ser Leu Glu Ser Cys Leu Thr Ser Ile Leu Ser

CACCCCACCGTGGGAAGCAAGGAGCACTTGGTCAGGCACACGGACAGGGTCAGCGGAGGA
------+----+----+----+----+----+----+----+----+----+----+----+ 1920
GTGGGGTGGCACCCTTCGTTCCTCGTGAACCAGTCCGTGTGCCTGTCCCAGTCGCCTCCT

His Pro Thr Val Gly Ser Lys Glu His Leu Val Arg His Thr Asp Arg Val Ser Gly Gly

CGCGTGGCACAGCAGCCCGGGGTAGGTCCCCTGGACCTGCCGCTGGCGGACTACGCCTTC
------+----+----+----+----+----+----+----+----+----+----+----+ 1980
GCGCACCGTGTCGTCGGGCCCCATCCAGGGGACCTGGACGGCGACCGCCTGATGCGGAAG

Arg Val Ala Gln Gln Pro Gly Val Gly Pro Leu Asp Leu Pro Leu Ala Asp Tyr Ala Phe

GTTGCCCACAGTCAGGTCTGGACCAGGCCCGGTGGGGCTCCTCCCTTGCCCTATCGTACC
------+----+----+----+----+----+----+----+----+----+----+----+ 2040
CAACGGGTGTCAGTCCAGACCTGGTCCGGGCCACCCCGAGGAGGGAACGGGATAGCATGG

Val Ala His Ser Gln Val Trp Thr Arg Pro Gly Gly Ala Pro Pro Leu Pro Tyr Arg Thr

TGGGATCGAATGACAGAGAAGCTGCTTGTCTCCGCAAAACCCGGCGGAGAGAACGTTAAG
------+----+----+----+----+----+----+----+----+----+----+----+ 2100
ACCCTAGCTTACTGTCTCTTCGACGAACAGAGGCGTTTTGGGCCGCCTCTCTTGCAATTC

Trp Asp Arg Met Thr Glu Lys Leu Leu Val Ser Ala Lys Pro Gly Gly Glu Asn Val Lys
```

FIG. 28C-5

```
GTTTCAGGTACCGTGATTACATTGGGAGAACAGGGGTACAAAGTGTCGTTGGATCTGAGG
-----+----+----+----+----+----+----+----+----+----+----+----+ 2160
CAAAGTCCATGGCACTAATGTAACCCTCTTGTCCCCATGTTTCACAGCAACCTAGACTCC

Val Ser Gly Thr Val Ile Thr Leu Gly Glu Gln Gly Tyr Lys Val Ser Leu Asp Leu Arg

GAGGGAACCAGGCTGGCAATGGCTGAGGCGCTGCTGAACGCAGCATGTGCCCCAATCTTG
-----+----+----+----+----+----+----+----+----+----+----+----+ 2220
CTCCCTTGGTCCGACCGTTACCGACTCCGCGACGACTTGCGTCGTACACGGGGTTAGAAC

Glu Gly Thr Arg Leu Ala Met Ala Glu Ala Leu Leu Asn Ala Ala Cys Ala Pro Ile Leu

GATCCGGAAGACGTCTTGCTCACCCTGCATCTACACCTGGATCCGCGCCGGGCAGACAAC
-----+----+----+----+----+----+----+----+----+----+----+----+ 2280
CTAGGCCTTCTGCAGAACGAGTGGGACGTAGATGTGGACCTAGGCGCGGCCCGTCTGTTG

Asp Pro Glu Asp Val Leu Leu Thr Leu His Leu His Leu Asp Pro Arg Arg Ala Asp Asn

TCGGCCGTGATGGAGGCTATGACGGCGGCGAGTGACTACGCGCGTGGCCTGGGCGTGAAG
-----+----+----+----+----+----+----+----+----+----+----+----+ 2340
AGCCGGCACTACCTCCGATACTGCCGCCGCTCACTGATGCGCGCACCGGACCCGCACTTC

Ser Ala Val Met Glu Ala Met Thr Ala Ala Ser Asp Tyr Ala Arg Gly Leu Gly Val Lys

CTGACCTTTGGCTCGGCCTCCTGCCCCGAGACCGGCTCGTCCGCCTCCAACTTCATGACC
-----+----+----+----+----+----+----+----+----+----+----+----+ 2400
GACTGGAAACCGAGCCGGAGGACGGGGCTCTGGCCGAGCAGGCGGAGGTTGAAGTACTGG

Leu Thr Phe Gly Ser Ala Ser Cys Pro Glu Thr Gly Ser Ser Ala Ser Asn Phe Met Thr

GTGGTGGCCTCTGTCTCCGCCCCAGGGGAATTCTCGGGTCCTCTGATCACGCCAGTGCTT
-----+----+----+----+----+----+----+----+----+----+----+----+ 2460
CACCACCGGAGACAGAGGCGGGGTCCCCTTAAGAGCCCAGGAGACTAGTGCGGTCACGAA

Val Val Ala Ser Val Ser Ala Pro Gly Glu Phe Ser Gly Pro Leu Ile Thr Pro Val Leu

CAGAAGACGGGCAGTCTCCTGATTGCGGTGCGTTGCGGGGATGGCAAGATCCAGGGAGGG
-----+----+----+----+----+----+----+----+----+----+----+----+ 2520
GTCTTCTGCCCGTCAGAGGACTAACGCCACGCAACGCCCCTACCGTTCTAGGTCCCTCCC

Gln Lys Thr Gly Ser Leu Leu Ile Ala Val Arg Cys Gly Asp Gly Lys Ile Gln Gly Gly
```

FIG. 28C-6

```
TCGCTGTTTGAGCAGCTCTTTAGCGACGTGGCCACGACCCCACGGGCACCCGAGGCGTTG
────┼────┼────┼────┼────┼────┼────┼────┼────┼────┼────┼────┼──── 2580
AGCGACAAACTCGTCGAGAAATCGCTGCACCGGTGCTGGGGTGCCCGTGGGCTCCGCAAC
Ser Leu Phe Glu Gln Leu Phe Ser Asp Val Ala Thr Thr Pro Arg Ala Pro Glu Ala Leu

TCTCTGAAGAATCTCTTCCGGGCAGTCCAGCAGCTGGTCAAGAGCGGCATCGTGCTGTCA
────┼────┼────┼────┼────┼────┼────┼────┼────┼────┼────┼────┼──── 2640
AGAGACTTCTTAGAGAAGGCCCGTCAGGTCGTCGACCAGTTCTCGCCGTAGCACGACAGT
Ser Leu Lys Asn Leu Phe Arg Ala Val Gln Gln Leu Val Lys Ser Gly Ile Val Leu Ser

GGGCATGACATCAGCGACGGGGGCCTGGTGACCTGCCTGGTGGAGATGGCCCTGGCCGGG
────┼────┼────┼────┼────┼────┼────┼────┼────┼────┼────┼────┼──── 2700
CCCGTACTGTAGTCGCTGCCCCCGGACCACTGGACGGACCACCTCTACCGGGACCGGCCC
Gly His Asp Ile Ser Asp Gly Gly Leu Val Thr Cys Leu Val Glu Met Ala Leu Ala Gly

CAGCGGGGAGTGACCATCACTATGCCGGTGGCCTCCGACTACCTCCCGGAGATGTTTGCA
────┼────┼────┼────┼────┼────┼────┼────┼────┼────┼────┼────┼──── 2760
GTCGCCCCTCACTGGTAGTGATACGGCCACCGGAGGCTGATGGAGGGCCTCTACAAACGT
Gln Arg Gly Val Thr Ile Thr Met Pro Val Ala Ser Asp Tyr Leu Pro Glu Met Phe Ala

GAGCACCCCGGCCTGGTGTTTGAGGTGGAGGAGCGCAGCGTGGGTGAGGTGCTGCAGACC
────┼────┼────┼────┼────┼────┼────┼────┼────┼────┼────┼────┼──── 2820
CTCGTGGGGCCGGACCACAAACTCCACCTCCTCGCGTCGCACCCACTCCACGACGTCTGG
Glu His Pro Gly Leu Val Phe Glu Val Glu Glu Arg Ser Val Gly Glu Val Leu Gln Thr

CTGCGCTCCATGAACATGTACCCGGCAGTCCTCGGTCGAGTGGGCGAGCAAGGTCCAGAT
────┼────┼────┼────┼────┼────┼────┼────┼────┼────┼────┼────┼──── 2880
GACGCGAGGTACTTGTACATGGGCCGTCAGGAGCCAGCTCACCCGCTCGTTCCAGGTCTA
Leu Arg Ser Met Asn Met Tyr Pro Ala Val Leu Gly Arg Val Gly Glu Gln Gly Pro Asp

CAAATGTTTGAGGTGCAGCACGGCCCAGAGACGGTGTTGCGCCAGTCGCTGCGCCTGCTG
────┼────┼────┼────┼────┼────┼────┼────┼────┼────┼────┼────┼──── 2940
GTTTACAAACTCCACGTCGTGCCGGGTCTCTGCCACAACGCGGTCAGCGACGCGGACGAC
Gln Met Phe Glu Val Gln His Gly Pro Glu Thr Val Leu Arg Gln Ser Leu Arg Leu Leu
```

FIG. 28C-7

```
CTGGGAACCTGGTCATCCTTTGCCAGCGAGCAGTACGAGTGCCTGCGACCAGATCGGATT
                                                              3000
GACCCTTGGACCAGTAGGAAACGGTCGCTCGTCATGCTCACGGACGCTGGTCTAGCCTAA
Leu Gly Thr Trp Ser Ser Phe Ala Ser Glu Gln Tyr Glu Cys Leu Arg Pro Asp Arg Ile

AACCGGTCCATGCACGTGTCCGACTACGGCTATAACGAAGCACTGGCAGTCTCCCCGTTG
                                                              3060
TTGGCCAGGTACGTGCACAGGCTGATGCCGATATTGCTTCGTGACCGTCAGAGGGGCAAC
Asn Arg Ser Met His Val Ser Asp Tyr Gly Tyr Asn Glu Ala Leu Ala Val Ser Pro Leu

ACAGGAAAGAATCTCAGCCCACGCCGGTTGGTGACAGAGCCTGACCCACGATGTCAGGTG
                                                              3120
TGTCCTTTCTTAGAGTCGGGTGCGGCCAACCACTGTCTCGGACTGGGTGCTACAGTCCAC
Thr Gly Lys Asn Leu Ser Pro Arg Arg Leu Val Thr Glu Pro Asp Pro Arg Cys Gln Val

GCCGTGCTATGCGCCCCGGGCACCAGGGGCCATGAAAGCCTCCTGGCGGCCTTCACGAAT
                                                              3180
CGGCACGATACGCGGGGCCCGTGGTCCCCGGTACTTTCGGAGGACCGCCGGAAGTGCTTA
Ala Val Leu Cys Ala Pro Gly Thr Arg Gly His Glu Ser Leu Leu Ala Ala Phe Thr Asn

GCCGGATGCCTGTGCCGACGGGTGTTCTTTCGCGAGGTTAGGGACAACACGTTCCTCGAC
                                                              3240
CGGCCTACGGACACGGCTGCCCACAAGAAAGCGCTCCAATCCCTGTTGTGCAAGGAGCTG
Ala Gly Cys Leu Cys Arg Arg Val Phe Phe Arg Glu Val Arg Asp Asn Thr Phe Leu Asp

AAGTACGTGGGTCTGGCCATCGGAGGAGTTCATGGGGCCAGGGACTCTGCCCTGGCAGGC
                                                              3300
TTCATGCACCCAGACCGGTAGCCTCCTCAAGTACCCCGGTCCCTGAGACGGGACCGTCCG
Lys Tyr Val Gly Leu Ala Ile Gly Gly Val His Gly Ala Arg Asp Ser Ala Leu Ala Gly

CGTGCCACCGTGGCGCTGATTAATCGTTTCCCCGCCCTGCGTGACGCTATTCTAAAGTTC
                                                              3360
GCACGGTGGCACCGCGACTAATTAGCAAAGGGGCGGGACGCACTGCGATAAGATTTCAAG
Arg Ala Thr Val Ala Leu Ile Asn Arg Phe Pro Ala Leu Arg Asp Ala Ile Leu Lys Phe
```

FIG. 28C-8

```
CTCAACAGGCCAGATACGTTCTCGGTGGCCTTGGGGGAGCTGGGGGTGCAAGTTTTGGCT
----+----+----+----+----+----+----+----+----+----+----+----+ 3420
GAGTTGTCCGGTCTATGCAAGAGCCACCGGAACCCCCTCGACCCCCACGTTCAAAACCGA

Leu Asn Arg Pro Asp Thr Phe Ser Val Ala Leu Gly Glu Leu Gly Val Gln Val Leu Ala

GGCCTGGGGGCCGTGGGGTCAACAGATAATCCACCCGCCCCTGGCGTGGAAGTTAATGTC
----+----+----+----+----+----+----+----+----+----+----+----+ 3480
CCGGACCCCCGGCACCCCAGTTGTCTATTAGGTGGGCGGGGACCGCACCTTCAATTACAG

Gly Leu Gly Ala Val Gly Ser Thr Asp Asn Pro Pro Ala Pro Gly Val Glu Val Asn Val

CAGAGATCACCTCTGATTCTGGCCCCCAACGCCTCTGGCATGTTTGAGTCCCGCTGGCTG
----+----+----+----+----+----+----+----+----+----+----+----+ 3540
GTCTCTAGTGGAGACTAAGACCGGGGGTTGCGGAGACCGTACAAACTCAGGGCGACCGAC

Gln Arg Ser Pro Leu Ile Leu Ala Pro Asn Ala Ser Gly Met Phe Glu Ser Arg Trp Leu

AACATTAGCATCCCGGCGACCACCAGCTCTGTCATGCTGCGTGGCCTCCGGGGCTGCGTC
----+----+----+----+----+----+----+----+----+----+----+----+ 3600
TTGTAATCGTAGGGCCGCTGGTGGTCGAGACAGTACGACGCACCGGAGGCCCCGACGCAG

Asn Ile Ser Ile Pro Ala Thr Thr Ser Ser Val Met Leu Arg Gly Leu Arg Gly Cys Val

CTGCCTTGTTGGGTGCAAGGCTCGTGCCTGGGCCTGCAATTTACTAACCTCGGGATGCCA
----+----+----+----+----+----+----+----+----+----+----+----+ 3660
GACGGAACAACCCACGTTCCGAGCACGGACCCGGACGTTAAATGATTGGAGCCCTACGGT

Leu Pro Cys Trp Val Gln Gly Ser Cys Leu Gly Leu Gln Phe Thr Asn Leu Gly Met Pro

TATGTTTTGCAGAATGCCCACCAGATCGCCTGCCACTTCCACAGCAATGGCACGGATGCC
----+----+----+----+----+----+----+----+----+----+----+----+ 3720
ATACAAAACGTCTTACGGGTGGTCTAGCGGACGGTGAAGGTGTCGTTACCGTGCCTACGG

Tyr Val Leu Gln Asn Ala His Gln Ile Ala Cys His Phe His Ser Asn Gly Thr Asp Ala

TGGCGCTTTGCTATGAATTATCCAAGAAACCCCACGGAGCAGGGCAACATTGCAGGGCTC
----+----+----+----+----+----+----+----+----+----+----+----+ 3780
ACCGCGAAACGATACTTAATAGGTTCTTTGGGGTGCCTCGTCCCGTTGTAACGTCCCGAG

Trp Arg Phe Ala Met Asn Tyr Pro Arg Asn Pro Thr Glu Gln Gly Asn Ile Ala Gly Leu
```

FIG. 28C-9

```
TGTTCACGCGATGGTCGTCATCTGGCTCTCCTGTGTGACCCCTCACTTTGTACAGACTTT
----+----+----+----+----+----+----+----+----+----+----+----+ 3840
ACAAGTGCGCTACCAGCAGTAGACCGAGAGGACACACTGGGGAGTGAAACATGTCTGAAA

Cys Ser Arg Asp Gly Arg His Leu Ala Leu Leu Cys Asp Pro Ser Leu Cys Thr Asp Phe

TGGCAATGGGAGCACATTCCCCCCGCCTTTGGGCACCCCACGGGGTGCTCCCCCTGGACA
----+----+----+----+----+----+----+----+----+----+----+----+ 3900
ACCGTTACCCTCGTGTAAGGGGGGCGGAAACCCGTGGGGTGCCCCACGAGGGGGACCTGT

Trp Gln Trp Glu His Ile Pro Pro Ala Phe Gly His Pro Thr Gly Cys Ser Pro Trp Thr

CTTATGTTTCAAGCAGCTCACCTATGGTCACTCAGGCACGGTCGCCCCTCCGAG
----+----+----+----+----+----+----+----+----+----+---→ 3954
GAATACAAAGTTCGTCGAGTGGATACCAGTGAGTCCGTGCCAGCGGGGAGGCTC

Leu Met Phe Gln Ala Ala His Leu Trp Ser Leu Arg His Gly Arg Pro Ser Glu
```

FIG. 28C-10

```
ATGGCCTCAAATGAGGGTGTGGAAAACAGACCCTTCCCCTATCTGACGGTGGATGCCGAC
                                                            + 60
TACCGGAGTTTACTCCCACACCTTTTGTCTGGGAAGGGGATAGACTGCCACCTACGGCTG
Met Ala Ser Asn Glu Gly Val Glu Asn Arg Pro Phe Pro Tyr Leu Thr Val Asp Ala Asp

CTGCTCTCGAACCTGCGGCAGTCAGCGGCTGAGGGGTTGTTTCATAGCTTTGACCTGCTG
                                                            + 120
GACGAGAGCTTGGACGCCGTCAGTCGCCGACTCCCCAACAAAGTATCGAAACTGGACGAC
Leu Leu Ser Asn Leu Arg Gln Ser Ala Ala Glu Gly Leu Phe His Ser Phe Asp Leu Leu

GTGGGCAAGGATGCCAGAGAGGCGGGCATCAAGTTTGAGGTGCTACTCGGGGTCTACACG
                                                            + 180
CACCCGTTCCTACGGTCTCTCCGCCCGTAGTTCAAACTCCACGATGAGCCCCAGATGTGC
Val Gly Lys Asp Ala Arg Glu Ala Gly Ile Lys Phe Glu Val Leu Leu Gly Val Tyr Thr

AACGCCATCCAATATGTTCGCTTCCTGGAGACGGCACTGGCCGTGTCCTGTGTGAACACG
                                                            + 240
TTGCGGTAGGTTATACAAGCGAAGGACCTCTGCCGTGACCGGCACAGGACACACTTGTGC
Asn Ala Ile Gln Tyr Val Arg Phe Leu Glu Thr Ala Leu Ala Val Ser Cys Val Asn Thr

GAATTCAAAGACCTGAGTCGTATGACGGATGGCAAGATTCAATTTCGAATCTCCGTCCCC
                                                            + 300
CTTAAGTTTCTGGACTCAGCATACTGCCTACCGTTCTAAGTTAAAGCTTAGAGGCAGGGG
Glu Phe Lys Asp Leu Ser Arg Met Thr Asp Gly Lys Ile Gln Phe Arg Ile Ser Val Pro

ACCATTGCTCACGGGGACGGAAGGAGACCCAGCAAGCAGCGGACATTCATTGTGGTCAAA
                                                            + 360
TGGTAACGAGTGCCCCTGCCTTCCTCTGGGTCGTTCGTCGCCTGTAAGTAACACCAGTTT
Thr Ile Ala His Gly Asp Gly Arg Arg Pro Ser Lys Gln Arg Thr Phe Ile Val Val Lys

AATTGCCACAAACACCACATTAGTACGGAAATGGAACTGTCCATGCTGGATCTGGAGATC
                                                            + 420
TTAACGGTGTTTGTGGTGTAATCATGCCTTTACCTTGACAGGTACGACCTAGACCTCTAG
Asn Cys His Lys His His Ile Ser Thr Glu Met Glu Leu Ser Met Leu Asp Leu Glu Ile
```

FIG. 28D-1

```
CTGCATAGTATCCCCGAGACCCCGGTCGAGTACGCAGAGTACGTGGGGGCTGTCAAGACC
────┼────┼────┼────┼────┼────┼────┼────┼────┼────┼────┼────┼ 480
GACGTATCATAGGGGCTCTGGGGCCAGCTCATGCGTCTCATGCACCCCGACAGTTCTGG

Leu His Ser Ile Pro Glu Thr Pro Val Glu Tyr Ala Glu Tyr Val Gly Ala Val Lys Thr

GTGGCCTCGGCCCTACAGTTTGGGGTCGATGCCCTGGAGAGGGGCCTCATTAACACCGTC
────┼────┼────┼────┼────┼────┼────┼────┼────┼────┼────┼────┼ 540
CACCGGAGCCGGGATGTCAAACCCCAGCTACGGGACCTCTCCCCGGAGTAATTGTGGCAG

Val Ala Ser Ala Leu Gln Phe Gly Val Asp Ala Leu Glu Arg Gly Leu Ile Asn Thr Val

CTGAGTGTGAAGCTTCGCCATGCCCCTCCCATGTTTATCCTGCAGACCCTGGCGGATCCC
────┼────┼────┼────┼────┼────┼────┼────┼────┼────┼────┼────┼ 600
GACTCACACTTCGAAGCGGTACGGGGAGGGTACAAATAGGACGTCTGGGACCGCCTAGGG

Leu Ser Val Lys Leu Arg His Ala Pro Pro Met Phe Ile Leu Gln Thr Leu Ala Asp Pro

ACCTTCACTGAGAGGGGGTTCTCCAAGACTGTCAAGTCTGACCTCATTGCCATGTTCAAG
────┼────┼────┼────┼────┼────┼────┼────┼────┼────┼────┼────┼ 660
TGGAAGTGACTCTCCCCCAAGAGGTTCTGACAGTTCAGACTGGAGTAACGGTACAAGTTC

Thr Phe Thr Glu Arg Gly Phe Ser Lys Thr Val Lys Ser Asp Leu Ile Ala Met Phe Lys

AGGCATCTGCTGGAGCACTCCTTCTTCCTGGACCGGGCCGAGAACATGGGCTCCGGGTTT
────┼────┼────┼────┼────┼────┼────┼────┼────┼────┼────┼────┼ 720
TCCGTAGACGACCTCGTGAGGAAGAAGGACCTGGCCCGGCTCTTGTACCCGAGGCCCAAA

Arg His Leu Leu Glu His Ser Phe Phe Leu Asp Arg Ala Glu Asn Met Gly Ser Gly Phe

TCTCAGTACGTGCGAAGCCGTCTCTCTGAGATGGTAGCGGCCGTGTCCGGGGAGAGCGTG
────┼────┼────┼────┼────┼────┼────┼────┼────┼────┼────┼────┼ 780
AGAGTCATGCACGCTTCGGCAGAGAGACTCTACCATCGCCGGCACAGGCCCCTCTCGCAC

Ser Gln Tyr Val Arg Ser Arg Leu Ser Glu Met Val Ala Ala Val Ser Gly Glu Ser Val

CTCAAGGGGGTCAGTACCTACACGACCGCCAAGGGGGGAGAGCCAGTGGGGGGGGTGTTT
────┼────┼────┼────┼────┼────┼────┼────┼────┼────┼────┼────┼ 840
GAGTTCCCCCAGTCATGGATGTGCTGGCGGTTCCCCCCTCTCGGTCACCCCCCCCACAAA

Leu Lys Gly Val Ser Thr Tyr Thr Thr Ala Lys Gly Gly Glu Pro Val Gly Gly Val Phe
```

FIG. 28D-2

```
ATTGTCACCGACAACGTTCTGCGCCAGCTCTTGACCTTCCTGGGTGAGGAGGCCGACAAC
------+---------+---------+---------+---------+---------+ 900
TAACAGTGGCTGTTGCAAGACGCGGTCGAGAACTGGAAGGACCCACTCCTCCGGCTGTTG
 Ile Val Thr Asp Asn Val Leu Arg Gln Leu Leu Thr Phe Leu Gly Glu Glu Ala Asp Asn

CAGATTATGGGGCCCTCGAGCTATGCTTCTTTTGTGGTACGGGGGGAGAACCTGGTCACT
------+---------+---------+---------+---------+---------+ 960
GTCTAATACCCCGGGAGCTCGATACGAAGAAAACACCATGCCCCCCTCTTGGACCAGTGA
 Gln Ile Met Gly Pro Ser Ser Tyr Ala Ser Phe Val Val Arg Gly Glu Asn Leu Val Thr

GCCGTGAGCTACGGGCGCGTGATGCGTACGTTTGAGCATTTCATGGCTAGGATCGTGGAC
------+---------+---------+---------+---------+---------+ 1020
CGGCACTCGATGCCCGCGCACTACGCATGCAAACTCGTAAAGTACCGATCCTAGCACCTG
 Ala Val Ser Tyr Gly Arg Val Met Arg Thr Phe Glu His Phe Met Ala Arg Ile Val Asp

TCACCGGAAAAAGCCGGAAGCACCAAGTCTGACCTGCCGGCTGTGGCCGCAGGGGTCGAG
------+---------+---------+---------+---------+---------+ 1080
AGTGGCCTTTTTCGGCCTTCGTGGTTCAGACTGGACGGCCGACACCGGCGTCCCCAGCTC
 Ser Pro Glu Lys Ala Gly Ser Thr Lys Ser Asp Leu Pro Ala Val Ala Ala Gly Val Glu

GATCAGCCCCGGGTGCCGATCTCAGCCGCCGTCATCAAGCTGGGCAACCACGCGGTGGCC
------+---------+---------+---------+---------+---------+ 1140
CTAGTCGGGGCCCACGGCTAGAGTCGGCGGCAGTAGTTCGACCCGTTGGTGCGCCACCGG
 Asp Gln Pro Arg Val Pro Ile Ser Ala Ala Val Ile Lys Leu Gly Asn His Ala Val Ala

GTGGAAAGCCTGCAAAAGATGTACAATGACACTCAGTCCCCATACCCCCTCAACAGAAGA
------+---------+---------+---------+---------+---------+ 1200
CACCTTTCGGACGTTTTCTACATGTTACTGTGAGTCAGGGGTATGGGGGAGTTGTCTTCT
 Val Glu Ser Leu Gln Lys Met Tyr Asn Asp Thr Gln Ser Pro Tyr Pro Leu Asn Arg Arg

ATGCAGTACAGCTACTATTTCCCAGTGGGCCTGTTTATGCCCAATCCCAAGTACACGACC
------+---------+---------+---------+---------+---------+ 1260
TACGTCATGTCGATGATAAAGGGTCACCCGGACAAATACGGGTTAGGGTTCATGTGCTGG
 Met Gln Tyr Ser Tyr Tyr Phe Pro Val Gly Leu Phe Met Pro Asn Pro Lys Tyr Thr Thr
```

FIG. 28D-3

```
TCCGCCGCCATCAAAATGCTGGACAACCCCACACAGCAGCTACCGGTGGAGGCATGGATC
------------------------------------------------------------  1320
AGGCGGCGGTAGTTTTACGACCTGTTGGGGTGTGTCGTCGATGGCCACCTCCGTACCTAG
 Ser Ala Ala Ile Lys Met Leu Asp Asn Pro Thr Gln Gln Leu Pro Val Glu Ala Trp Ile

GTAAACAAGAATAACCTTCTCCTCGCGTTTAACCTACAGAATGCTCTCAAGGTTCTCTGT
------------------------------------------------------------  1380
CATTTGTTCTTATTGGAAGAGGAGCGCAAATTGGATGTCTTACGAGAGTTCCAAGAGACA
 Val Asn Lys Asn Asn Leu Leu Leu Ala Phe Asn Leu Gln Asn Ala Leu Lys Val Leu Cys

CACCCCCGACTCCACACACCCGCCCATACCCTAAACAGCCTCAACGCGGCCCCGGCCCCG
------------------------------------------------------------  1440
GTGGGGGCTGAGGTGTGTGGGCGGGTATGGGATTTGTCGGAGTTGCGCCGGGGCCGGGGC
 His Pro Arg Leu His Thr Pro Ala His Thr Leu Asn Ser Leu Asn Ala Ala Pro Ala Pro

CGAGACAGGCGCGAGACCTACTCCCTGCAACACAGGAGGCCCAATCACATGAATGTGCTT
------------------------------------------------------------  1500
GCTCTGTCCGCGCTCTGGATGAGGGACGTTGTGTCCTCCGGGTTAGTGTACTTACACGAA
 Arg Asp Arg Arg Glu Thr Tyr Ser Leu Gln His Arg Arg Pro Asn His Met Asn Val Leu

GTTATTGTGGACGAGTTCTATGATAACAAGTATGCAGCCCCGTGACAGATATAGCTCTC
------------------------------------------------------------  1560
CAATAACACCTGCTCAAGATACTATTGTTCATACGTCGGGGGCACTGTCTATATCGAGAG
 Val Ile Val Asp Glu Phe Tyr Asp Asn Lys Tyr Ala Ala Pro Val Thr Asp Ile Ala Leu

AAGTGCGGGCTGCCCACCGAAGACTTCCTCCACCCGTCCAATTATGACCTGCTGCGGCTG
------------------------------------------------------------  1620
TTCACGCCCGACGGGTGGCTTCTGAAGGAGGTGGGCAGGTTAATACTGGACGACGCCGAC
 Lys Cys Gly Leu Pro Thr Glu Asp Phe Leu His Pro Ser Asn Tyr Asp Leu Leu Arg Leu

GAGCTGCACCCCCTTTATGATATTTACATTGGCAGGGATGCCGGGGAGAGGGCCAGGCAC
------------------------------------------------------------  1680
CTCGACGTGGGGGAAATACTATAAATGTAACCGTCCCTACGGCCCCTCTCCCGGTCCGTG
 Glu Leu His Pro Leu Tyr Asp Ile Tyr Ile Gly Arg Asp Ala Gly Glu Arg Ala Arg His
```

FIG. 28D-4

```
AGGGCTGTGCACCGGCTAATGGTGGGTAACCTGCCGACTCCCCTGGCCCCAGCTGCATTC
----+----+----+----+----+----+----+----+----+----+----+----+ 1740
TCCCGACACGTGGCCGATTACCACCCATTGGACGGCTGAGGGGACCGGGGTCGACGTAAG
 Arg Ala Val His Arg Leu Met Val Gly Asn Leu Pro Thr Pro Leu Ala Pro Ala Ala Phe

CAAGAGGCCCGGGGGCAGCAGTTTGAGACCGCCACATCTCTGGCCCACGTGGTGGATCAG
----+----+----+----+----+----+----+----+----+----+----+----+ 1800
GTTCTCCGGGCCCCCGTCGTCAAACTCTGGCGGTGTAGAGACCGGGTGCACCACCTAGTC
 Gln Glu Ala Arg Gly Gln Gln Phe Glu Thr Ala Thr Ser Leu Ala His Val Val Asp Gln

GCCGTTATTGAGACTGTGCAGGATACTGCCTATGACACTGCCTATCCAGCCTTCTTCTAC
----+----+----+----+----+----+----+----+----+----+----+----+ 1860
CGGCAATAACTCTGACACGTCCTATGACGGATACTGTGACGGATAGGTCGGAAGAAGATG
 Ala Val Ile Glu Thr Val Gln Asp Thr Ala Tyr Asp Thr Ala Tyr Pro Ala Phe Phe Tyr

GTAGTCGAGGCTATGATCCACGGGTTTGAGGAAAAGTTTGTCATGAACGTGCCTTTGGTG
----+----+----+----+----+----+----+----+----+----+----+----+ 1920
CATCAGCTCCGATACTAGGTGCCCAAACTCCTTTTCAAACAGTACTTGCACGGAAACCAC
 Val Val Glu Ala Met Ile His Gly Phe Glu Glu Lys Phe Val Met Asn Val Pro Leu Val

TCCCTGTGCATCAACACCTACTGGGAACGGTCAGGGAGGCTTGCCTTTGTGAACAGCTTT
----+----+----+----+----+----+----+----+----+----+----+----+ 1980
AGGGACACGTAGTTGTGGATGACCCTTGCCAGTCCCTCCGAACGGAAACACTTGTCGAAA
 Ser Leu Cys Ile Asn Thr Tyr Trp Glu Arg Ser Gly Arg Leu Ala Phe Val Asn Ser Phe

TCCATGATCAAGTTCATCTGCCGCCACCTGGGAAATAACGCCATCTCCAAGGAGGCCTAT
----+----+----+----+----+----+----+----+----+----+----+----+ 2040
AGGTACTAGTTCAAGTAGACGGCGGTGGACCCTTTATTGCGGTAGAGGTTCCTCCGGATA
 Ser Met Ile Lys Phe Ile Cys Arg His Leu Gly Asn Asn Ala Ile Ser Lys Glu Ala Tyr

TCCATGTATAGAAAAATCTATGGGGAACTTATAGCCCTAGAGCAGGCCCTGATGCGCCTG
----+----+----+----+----+----+----+----+----+----+----+----+ 2100
AGGTACATATCTTTTTAGATACCCCTTGAATATCGGGATCTCGTCCGGGACTACGCGGAC
 Ser Met Tyr Arg Lys Ile Tyr Gly Glu Leu Ile Ala Leu Glu Gln Ala Leu Met Arg Leu
```

FIG. 28D-5

```
GCCGGGTCAGATGTTGTGGGGGATGAGAGCGTGGGTCAGTATGTCTGCGCTCTCCTGGAC
------+---------+---------+---------+---------+---------+  2160
CGGCCCAGTCTACAACACCCCCTACTCTCGCACCCAGTCATACAGACGCGAGAGGACCTG
 Ala Gly Ser Asp Val Val Gly Asp Glu Ser Val Gly Gln Tyr Val Cys Ala Leu Leu Asp

CCTAACCTGCTCCCCCCGGTGGCCTACACAGACATTTTCACCCATCTTCTCACCGTTAGT
------+---------+---------+---------+---------+---------+  2220
GGATTGGACGAGGGGGGCCACCGGATGTGTCTGTAAAAGTGGGTAGAAGAGTGGCAATCA
 Pro Asn Leu Leu Pro Pro Val Ala Tyr Thr Asp Ile Phe Thr His Leu Leu Thr Val Ser

GACCGGGCCCCCCAGATTATTATCGGAAATGAGGTTTACGCTGACACCCTGGCCGCGCCC
------+---------+---------+---------+---------+---------+  2280
CTGGCCCGGGGGGTCTAATAATAGCCTTTACTCCAAATGCGACTGTGGGACCGGCGCGGG
 Asp Arg Ala Pro Gln Ile Ile Ile Gly Asn Glu Val Tyr Ala Asp Thr Leu Ala Ala Pro

CAGTTTATTGAGAGGGTTGGAAACATGGATGAGATGGCTGCCCAATTTGTGGCCTTGTAC
------+---------+---------+---------+---------+---------+  2340
GTCAAATAACTCTCCCAACCTTTGTACCTACTCTACCGACGGGTTAAACACCGGAACATG
 Gln Phe Ile Glu Arg Val Gly Asn Met Asp Glu Met Ala Ala Gln Phe Val Ala Leu Tyr

GGCTACCGGGTTAACGGAGACCACGACCACGATTTCCGTCTGCACCTAGGCCCTTATGTA
------+---------+---------+---------+---------+---------+  2400
CCGATGGCCCAATTGCCTCTGGTGCTGGTGCTAAAGGCAGACGTGGATCCGGGAATACAT
 Gly Tyr Arg Val Asn Gly Asp His Asp His Asp Phe Arg Leu His Leu Gly Pro Tyr Val

GATGAGGGGCATGCGGATGTGCTGGAAAAGATCTTTTACTACGTTTTCCTCCCAACCTGC
------+---------+---------+---------+---------+---------+  2460
CTACTCCCCGTACGCCTACACGACCTTTTCTAGAAAATGATGCAAAAGGAGGGTTGGACG
 Asp Glu Gly His Ala Asp Val Leu Glu Lys Ile Phe Tyr Tyr Val Phe Leu Pro Thr Cys

ACCAATGCCCACATGTGCGGCCTCGGGGTGGACTTTCAGCACGTGGCCCAGACCCTGGCC
------+---------+---------+---------+---------+---------+  2520
TGGTTACGGGTGTACACGCCGGAGCCCCACCTGAAAGTCGTGCACCGGGTCTGGGACCGG
 Thr Asn Ala His Met Cys Gly Leu Gly Val Asp Phe Gln His Val Ala Gln Thr Leu Ala
```

FIG. 28D-6

```
TACAACGGGCCAGCCTTCAGCCACCATTTTACCAGGGACGAGGACATCCTCGACAATTTG
------------------------------------------------------------ 2580
ATGTTGCCCGGTCGGAAGTCGGTGGTAAAATGGTCCCTGCTCCTGTAGGAGCTGTTAAAC
 Tyr Asn Gly Pro Ala Phe Ser His His Phe Thr Arg Asp Glu Asp Ile Leu Asp Asn Leu

GAGAATGGGACGCTCAGGGATCTGCTGGAGATCTCCGACCTCCGCCCCACCGTGGGCATG
------------------------------------------------------------ 2640
CTCTTACCCTGCGAGTCCCTAGACGACCTCTAGAGGCTGGAGGCGGGGTGGCACCCGTAC
 Glu Asn Gly Thr Leu Arg Asp Leu Leu Glu Ile Ser Asp Leu Arg Pro Thr Val Gly Met

ATCAGGGACCTCAGCGCCTCATTCATGACCTGCCCCACTTTCACCCGTGCCGTGCGTGTG
------------------------------------------------------------ 2700
TAGTCCCTGGAGTCGCGGAGTAAGTACTGGACGGGGTGAAAGTGGGCACGGCACGCACAC
 Ile Arg Asp Leu Ser Ala Ser Phe Met Thr Cys Pro Thr Phe Thr Arg Ala Val Arg Val

TCGGTGGACAATGACGTTACGCAGCAGCTGGCCCCGAATCCCGCCGACAAGCGGACAGAG
------------------------------------------------------------ 2760
AGCCACCTGTTACTGCAATGCGTCGTCGACCGGGGCTTAGGGCGGCTGTTCGCCTGTCTC
 Ser Val Asp Asn Asp Val Thr Gln Gln Leu Ala Pro Asn Pro Ala Asp Lys Arg Thr Glu

CAGACTGTTTTGGTGAACGGGCTGGTGGCCTTTGCCTTCTCCGAGAGGACCCGGGCCGTC
------------------------------------------------------------ 2820
GTCTGACAAAACCACTTGCCCGACCACCGGAAACGGAAGAGGCTCTCCTGGGCCCGGCAG
 Gln Thr Val Leu Val Asn Gly Leu Val Ala Phe Ala Phe Ser Glu Arg Thr Arg Ala Val

ACCCAGTGTCTCTTTCACGCCATTCCTTTCCATATGTTTTACGGGGACCCGCGAGTGGCT
------------------------------------------------------------ 2880
TGGGTCACAGAGAAAGTGCGGTAAGGAAAGGTATACAAAATGCCCCTGGGCGCTCACCGA
 Thr Gln Cys Leu Phe His Ala Ile Pro Phe His Met Phe Tyr Gly Asp Pro Arg Val Ala

GCCACCATGCACCAGGATGTTGCCACCTTTGTTATGCGCAATCCTCAGCAGCGGGCCGTG
------------------------------------------------------------ 2940
CGGTGGTACGTGGTCCTACAACGGTGGAAACAATACGCGTTAGGAGTCGTCGCCCGGCAC
 Ala Thr Met His Gln Asp Val Ala Thr Phe Val Met Arg Asn Pro Gln Gln Arg Ala Val
```

FIG. 28D-7

```
GAAGCCTTCAACCGGCCAGAGCAGCTCTTTGCAGAGTACCGGGAGTGGCACCGCTCGCCC
————+————+————+————+————+————+————+————+————+————+————+————+ 3000
CTTCGGAAGTTGGCCGGTCTCGTCGAGAAACGTCTCATGGCCCTCACCGTGGCGAGCGGG
 Glu Ala Phe Asn Arg Pro Glu Gln Leu Phe Ala Glu Tyr Arg Glu Trp His Arg Ser Pro

ATGGGCAAATACGCGGCCGAATGTCTTCCTTCCCTCGTTTCAATCAGTGGAATGACCGCC
————+————+————+————+————+————+————+————+————+————+————+————+ 3060
TACCCGTTTATGCGCCGGCTTACAGAAGGAAGGGAGCAAAGTTAGTCACCTTACTGGCGG
 Met Gly Lys Tyr Ala Ala Glu Cys Leu Pro Ser Leu Val Ser Ile Ser Gly Met Thr Ala

ATGCACATCAAGATGTCCCCCATGGCCTATATTGCCCAGGCCAAGCTCAAGATCCACCCA
————+————+————+————+————+————+————+————+————+————+————+————+ 3120
TACGTGTAGTTCTACAGGGGGTACCGGATATAACGGGTCCGGTTCGAGTTCTAGGTGGGT
 Met His Ile Lys Met Ser Pro Met Ala Tyr Ile Ala Gln Ala Lys Leu Lys Ile His Pro

GGGGTGGCCATGACCGTGGTCAGGACCGATGAGATCCTCTCTGAAAACATATTGTTTAGC
————+————+————+————+————+————+————+————+————+————+————+————+ 3180
CCCCACCGGTACTGGCACCAGTCCTGGCTACTCTAGGAGAGACTTTTGTATAACAAATCG
 Gly Val Ala Met Thr Val Val Arg Thr Asp Glu Ile Leu Ser Glu Asn Ile Leu Phe Ser

TCCAGGGCCTCAACATCCATGTTCATTGGGACCCCAAATGTTAGCCGCCGGGAGGCCAGG
————+————+————+————+————+————+————+————+————+————+————+————+ 3240
AGGTCCCGGAGTTGTAGGTACAAGTAACCCTGGGGTTTACAATCGGCGGCCCTCCGGTCC
 Ser Arg Ala Ser Thr Ser Met Phe Ile Gly Thr Pro Asn Val Ser Arg Arg Glu Ala Arg

GTGGACGCGGTAACCTTTGAGGTGCATCACGAGATGGCCTCCATCGACACCGGGCTTAGT
————+————+————+————+————+————+————+————+————+————+————+————+ 3300
CACCTGCGCCATTGGAAACTCCACGTAGTGCTCTACCGGAGGTAGCTGTGGCCCGAATCA
 Val Asp Ala Val Thr Phe Glu Val His His Glu Met Ala Ser Ile Asp Thr Gly Leu Ser

TATAGCTCGACCATGACTCCGGCCAGGGTGGCGGCCATCACTACTGACATGGGTATCCAC
————+————+————+————+————+————+————+————+————+————+————+————+ 3360
ATATCGAGCTGGTACTGAGGCCGGTCCCACCGCCGGTAGTGATGACTGTACCCATAGGTG
 Tyr Ser Ser Thr Met Thr Pro Ala Arg Val Ala Ala Ile Thr Thr Asp Met Gly Ile His
```

FIG. 28D-8

```
ACCCAAGACTTCTTTAGCGTCTTTCCGGCCGAGGCCTTTGGCAACCAGCAAGTCAATGAC
————+————+————+————+————+————+————+————+————+————+————+————+  3420
TGGGTTCTGAAGAAATCGCAGAAAGGCCGGCTCCGGAAACCGTTGGTCGTTCAGTTACTG

Thr Gln Asp Phe Phe Ser Val Phe Pro Ala Glu Ala Phe Gly Asn Gln Gln Val Asn Asp

TACATCAAGGCCAAGGTGGGCGCTCAGCGCAATGGGACGCTGCTTCGGGACCCCAGGACA
————+————+————+————+————+————+————+————+————+————+————+————+  3480
ATGTAGTTCCGGTTCCACCCGCGAGTCGCGTTACCCTGCGACGAAGCCCTGGGGTCCTGT

Tyr Ile Lys Ala Lys Val Gly Ala Gln Arg Asn Gly Thr Leu Leu Arg Asp Pro Arg Thr

TACCTGGCAGGTATGACTAATGTTAATGGAGCTCCAGGACTCTGCCACGGCCAGCAGGCC
————+————+————+————+————+————+————+————+————+————+————+————+  3540
ATGGACCGTCCATACTGATTACAATTACCTCGAGGTCCTGAGACGGTGCCGGTCGTCCGG

Tyr Leu Ala Gly Met Thr Asn Val Asn Gly Ala Pro Gly Leu Cys His Gly Gln Gln Ala

ACCTGTGAGATTATCGTAACACCGGTCACGGCAGACGTGGCTTATTTTCAAAAGTCCAAC
————+————+————+————+————+————+————+————+————+————+————+————+  3600
TGGACACTCTAATAGCATTGTGGCCAGTGCCGTCTGCACCGAATAAAAGTTTTCAGGTTG

Thr Cys Glu Ile Ile Val Thr Pro Val Thr Ala Asp Val Ala Tyr Phe Gln Lys Ser Asn

TCTCCAAGGGGACGGGCCGCCTGTGTGGTCTCCTGTGAAAACTACAATCAGGAGGTTGCC
————+————+————+————+————+————+————+————+————+————+————+————+  3660
AGAGGTTCCCCTGCCCGGCGGACACACCAGAGGACACTTTTGATGTTAGTCCTCCAACGG

Ser Pro Arg Gly Arg Ala Ala Cys Val Val Ser Cys Glu Asn Tyr Asn Gln Glu Val Ala

GAGGGGCTCATCTATGACCATTCTCGCCCGGATGCCGCCTATGAATACCGGAGCACTGTG
————+————+————+————+————+————+————+————+————+————+————+————+  3720
CTCCCCGAGTAGATACTGGTAAGAGCGGGCCTACGGCGGATACTTATGGCCTCGTGACAC

Glu Gly Leu Ile Tyr Asp His Ser Arg Pro Asp Ala Ala Tyr Glu Tyr Arg Ser Thr Val

AATCCCTGGGCATCTCAGCTGGGTTCTCTGGGTGACATCATGTACAACTCCTCCTATCGC
————+————+————+————+————+————+————+————+————+————+————+————+  3780
TTAGGGACCCGTAGAGTCGACCCAAGAGACCCACTGTAGTACATGTTGAGGAGGATAGCG

Asn Pro Trp Ala Ser Gln Leu Gly Ser Leu Gly Asp Ile Met Tyr Asn Ser Ser Tyr Arg
```

FIG. 28D-9

```
CAGACGGCCGTCCCGGGCCTCTACAGCCCCTGCCGGGCATTTTTCAACAAGGAGGAGCTT
────┼────┼────┼────┼────┼────┼────┼────┼────┼────┼────┼────┼ 3840
GTCTGCCGGCAGGGCCCGGAGATGTCGGGGACGGCCCGTAAAAAGTTGTTCCTCCTCGAA
 Gln Thr Ala Val Pro Gly Leu Tyr Ser Pro Cys Arg Ala Phe Phe Asn Lys Glu Glu Leu

CTGCGCAACAACAGGGGACTCTACAACATGGTCAACGAGTACAGCCAGCGACTTGGAGGG
────┼────┼────┼────┼────┼────┼────┼────┼────┼────┼────┼────┼ 3900
GACGCGTTGTTGTCCCCTGAGATGTTGTACCAGTTGCTCATGTCGGTCGCTGAACCTCCC
 Leu Arg Asn Asn Arg Gly Leu Tyr Asn Met Val Asn Glu Tyr Ser Gln Arg Leu Gly Gly

CACCCAGCCACCAGCAACACAGAGGTGCAGTTTGTAGTGATTGCTGGCACTGACGTGTTT
────┼────┼────┼────┼────┼────┼────┼────┼────┼────┼────┼────┼ 3960
GTGGGTCGGTGGTCGTTGTGTCTCCACGTCAAACATCACTAACGACCGTGACTGCACAAA
 His Pro Ala Thr Ser Asn Thr Glu Val Gln Phe Val Val Ile Ala Gly Thr Asp Val Phe

CTGGAGCAGCCCTGCAGCTTTCTGCAGGAGGCATTCCCCGCACTCTCAGCCTCCTCCCGG
────┼────┼────┼────┼────┼────┼────┼────┼────┼────┼────┼────┼ 4020
GACCTCGTCGGGACGTCGAAAGACGTCCTCCGTAAGGGGCGTGAGAGTCGGAGGAGGGCC
 Leu Glu Gln Pro Cys Ser Phe Leu Gln Glu Ala Phe Pro Ala Leu Ser Ala Ser Ser Arg

GCACTCATCGATGAGTTTATGTCTGTCAAACAGACCCACGCCCCCATCCATTACGGACAC
────┼────┼────┼────┼────┼────┼────┼────┼────┼────┼────┼────┼ 4080
CGTGAGTAGCTACTCAAATACAGACAGTTTGTCTGGGTGCGGGGGTAGGTAATGCCTGTG
 Ala Leu Ile Asp Glu Phe Met Ser Val Lys Gln Thr His Ala Pro Ile His Tyr Gly His

TATATAATTGAAGAGGTGGCGCCGGTACGAAGAATATTAAAGTTTGGAAATAAGGTGGTT
────┼────┼────┼────┼────┼────┼────┼────┼────┼────┼────┼────┼ 4140
ATATATTAACTTCTCCACCGCGGCCATGCTTCTTATAATTTCAAACCTTTATTCCACCAA
 Tyr Ile Ile Glu Glu Val Ala Pro Val Arg Arg Ile Leu Lys Phe Gly Asn Lys Val Val

TTT
───▶ 4143
AAA
Phe
───▶
```

FIG. 28D-10

DNA SEQUENCES OF THE EBV GENOME, RECOMBINANT DNA MOLECULES, PROCESSES FOR PREPARING EBV-RELATED ANTIGENS, DIAGNOSTIC COMPOSITIONS AND PHARMACEUTICAL COMPOSITIONS CONTAINING SAID ANTIGENS

This is a Continuation of application Ser. No. 08/152,096, filed on Nov. 15, 1993, now abandoned, which is a Continuation of application Ser. No. 07/802,701, filed on Dec. 5, 1991, now abandoned, which is a continuation of Ser. No. 07/613,969, filed on Nov. 15, 1990, now abandoned, which is a continuation of Ser. No. 07/331,016, filed on Mar. 29, 1989, now abandoned, which is continuation of Ser. No. 06/768,334, filed Aug. 22, 1985, now abandoned.

TECHNICAL FIELD OF INVENTION

This invention relates to DNA sequences of the EBV genome coding at least for parts of EBV-related antigens to be used in methods and diagnostic and pharmaceutical compositions referred to below and methods of localising and isolating at least part of the respective DNA sequences.

Furthermore the invention relates to recombinant DNA molecules i.e. cloning and expression vectors useful for the production of antigenic determinants of said EBV-related antigens after introduction of these vectors into appropriate hosts such as bacteria, yeasts and mammalian cells.

Finally this invention relates to methods and compositions or kits, respectively, for a rapid, simple, highly sensitive and highly specific determination of antibodies directed to EBV-related antigens. In these tests different antigens of EBV are used to detect specific antibody classes in the patient's serum, directed to these antigens. This detection allows fairly reliable conclusions as to the status of infection of the serum donor such as preinfection, fresh infection, chronic infection, convalescence and neoplastic condition. Furthermore, this invention relates to pharmaceutical compositions, e.g. vaccines containing said antigens useful for prophylaxis and therapy of EBV-related diseases.

BACKGROUND ART

The herpesviruses (Herpetoviridiae) are enveloped icosahedral capsids with an overall diameter of 15o nm. The viral genome consists of a double-stranded DNA with a molecular weight of approximately 108 D. Human herpes-viruses are Herpes simplex I ("fever blisters"), Herpes simplex II (genital herpes), Varicella-Zoster (chickenpox, shingles), Cytomegalovirus (congenital abnormalities, e.g. microcephaly), and Epstein-Barr virus (EBV) (infectious mononucleosis (IM), Burkitt's lymphoma (BL), nasopharyngeal carcinoma (NPC)

Herpesviruses display a remarkable propensity for establishing latent infections which may persist for the life of the host. After the primary infection the virus may remain quiescent, being demonstrable only sporadically or not at all, until it is reactivated by one of several known types of stimulus, such as irradiation or immunosuppression. Such exacerbations of endogenous disease may take the form of a crop of vesicles on the skin in the case of herpes simplex or zoster, or more generalized effects in the case of cytomegalovirus or EBV. The capacity to persist indefinitely as a latent infection enables these viruses to survive in nature for a long time. During the last years, attention has turned to the correlation of human cancer and EBV.

Epstein-Barr-Virus (EBV), infections and their consequences

EBV causes infectious mononucleosis as a primary disease. Predominantly it affects children or young adults. More than 90% of the average adult population is infected by EBV that persists for lifetime in peripheral B-lymphocytes. The virus is produced in the parotid gland and spread via the oral route during the lifetime of the infected person.

Serology suggests that EBV might be involved in causing two neoplastic diseases of man, African Burkitt's lymphoma (BL) and nasopharyngeal carcinoma (NPC). Infectious mononucleosis is a consequence of primary infection by EBV. It is not a life-threatening disease if additional risk factors are absent.

However, the subjective feeling of sickness, frequently for extended periods (such as for several weeks), and the necessity to avoid physical stress due to the drastically increased risk of spleenic rupture indicates that there is a need to control this disease.

The clinical diagnosis of infectious mononucleosis is usually derived from a combination of the following parameters:

1. High leukocyte count ranging from 10,000 to 20,000 and reaching up to 50,000
2. 10% atypical cells
3. lymphadenitis
4. fever.

Patients with infectious mononucleosis shed EBV in their saliva. Virus shedding does not require special prevention against spreading the disease as epidemics and infection of persons in close contact are rare (A. S. Evans, "The transmission of EB viral infections. Viral Infections in Oral Medicine.", edited by J. Hooks, G. Jordan, Elsevier North Holland Amsterdam, p. 211 (1982)). Virus shedding does not stop with recovery from disease and at least 60% (possibly up to 100%) of the adult population shed at least low levels of EBV which is produced for a libetine in epithelial cells of the salivary duct of the parotid gland (H. Wolf, M. Haus, E. Wilmes, "Persistence of Epstein-Barr virus in the parotid gland", J. Virol. 51 (1984)).

About 1% of the infectious mononucleosis cases show complications either already at the onset of the disease or as a late consequence. Most complications are due to autoimmune mechanisms and are in some cases indiscernable from graft versus host disease, a mechanism by which the body might clear itself from the excess of EBV converted proliferating B-cells.

If the T-cell response is insufficient, e.g. due to circumstances like treatment with high doses of Cyclosporin A in combination with corticosteroids or due to AIDS or a certain genetic predisposition as described by Purtilo (Duncan's syndrome, X-chromosome-linked lympho-proliferative disease (XLP); D. T. Purtilo, K. Sakamoto, V. Barnabei, J. Seeley, T. Bechtolg, G. Rogers, J. Yenz, S. Harada and the XLP-collaborators: "Epstein-Barr virus-induced diseases in boys with the X-Linked lymopho-proliferative syndrome (XLP). Update on studies of the registry." Am. J. Med. 73, p. 49 (1982)), infected B-cells may have a chance to escape from host control and grow without limitation as they would do when being cultivated in vitro. The consequences have been described as BL-like disease in cases of AIDS patients (J. L. Ziegler, R. C. Miner, E. Rosenbaum, E. T. Lennette, E. Shillitoe, C. Casavant, W. L. Drew, L. Mintz, J Gershor, J. Greenspan, J. Beckstead, K. Yamamoto, "Outbreak of Burkitt's-like lymphoma in homosexual men.", Lancet 2, p. 631 (1982)) or as a polyclonal lympho-proliferative disease for XLP-patients (D. T. Purtilo et al., supra) or kidney transplant recipients (D. W. Hanto, G. Frizzera, D. T. Purtilo, K. Sakamoto, J. L. Sullivan, A. K. Saemundsen, G. Klein, R. L. Simmons, J. S. Najarian, "Clinical spectrum of lymphoproliferative disorders in renal transplant recipients and evidence for the role of Epstein-Barr virus.", Cancer Res. 41, p. 4253 (1981)).

The positive and fast identification of infectious mononucleosis or acute EBV infection is especially important in cases where a differential diagnosis to leukemia or, in case of transplant recipient, to graft rejection crisis is necessary. In these cases, a false diagnosis may lead to incorrect therapy, which may have serious, even life-threatening effects.

Prevention of primary disease caused by EBV

Infectious mononucleosis seems to be unknown in areas like the Philippines or Malaysia (D. S. K. Tan, "Absence of infectious mononucleosis among Asians in Malaya.", Med. J. Malaya 21, p. 358 (1967)) where infection by EBV occurs very early in life. Almost the whole population has antibodies at the age of 2–10 years at the latest. Clinical symptoms seem to be a consequence of juvenile or adult infection. It can be assumed that a vaccine-primed organism will be infected without significant clinical symptoms and that the consequences often fatal in the risk groups listed above could be eliminated by a vaccine.

Burkitt's Lymphoma and EBV

The development of Burkitt's lymphoma is linked to chromosomal rearrangements. Not all cases contain EBV genomes in the tumor cells. However, at least in areas with high incidence, 97% of these neoplasias are EBV-related and a control of EBV infection is likely to reduce the risk of developing Burkitt's lymphoma.

Nasopharyngeal carcinoma as a possible "secondary disease" related to EBV

The other disease where EBV shows a 100% association is nasopharyngeal carcinoma (NPC) ("The Biology of Nasopharyngeal Carcinoma", UICC technical report series, vol. 71, edited by M. J. Simons and K. Shanmugaratnam, International Union Against Cancer, Geneva, p. 1 (1982)). NPC most frequently starts at the fossa of Rosenmueller (Recessus pharyngeus) at the postnasal space. Frequently patients are hospitalized only after the first typical metastases have developed in the cervical lymph nodes.

In some areas of Southern China and amongst Chinese in Singapore and Malaysia, NPC is the most frequent neoplasia of man with an incidence of up to 10 per 100,000 per year. In other parts of the world, like Borneo or Tunesia the incidence is also high. In most other areas, the incidence is around 0.2 per 100,000 per year which represents about 4% of ear, nose and throat (ENT)-tumors. The age distribution shows a clear single peak around the age of 40 to 50 in almost all high-risk areas. In Borneo and to some extent in Tunesia, a remarkable second peak has, however, been observed at an early age ranging from 5 to 15 years (M. J. Simons et al., supra).

Environmental factors including traditional Chinese medicine may be responsible for the increased risk of nasopharyngeal carcinoma in certain, predominantly Chinese, populations of Southern Asia (H. Wolf, "Biology of Epstein-Barr virus in: "Immune deficiency and cancer: Epstein-Barr virus and lymphoproliferative malignancies"; ed. D. Purtilo, Plenum Press, p. 233 (1984)).

Control of EBV-related neoplasia

There are three possible basic strategies to control neoplasia:

1. Early detection followed by therapy, 2. delay of onset of disease ideally beyond the average lifespan, and 3. prevention.

These goals may be achieved also in multifactorial diseases such as many neoplasias. Incidence of disease may be reduced by eliminating one or more of the essential factors which are not necessarily sufficient by themselves to cause the disease, or by reducing factors which promote the manifestation of neoplastic conditions. The use of the specific virus-related antigens of this invention, or antibodies or genetic materials as tools for early diagnosis of virus-related tumors, might facilitate the elimination of essential factors.

Selection of EBV-related gene products for diagnosis of EBV-related NPC

A. Primary infection with EBV: Development of antibodies against VCA (viral capsid antigen), EA (early antigen) and EBNA (Epstein-Barr Nuclear Antigen)

EBV infects B-lymphocytes during acute or primary infection (mononucleosis). Due to the lack of immune response, a number of cells enter into the lytic cycle and produce a full set of viral antigens which are shed into the blood stream during cytolysis. Against these antigens, specific antibodies will be synthesized by the host's immune system (Table A).

Probably not all B-lymphocytes are capable of supporting a fully lytic infection due to a cellular factor which prevents expression of EBV. These cells are latently carrying EBV genomes for the rest of the host's life.

TABLE A

| DISEASE | VCA: $I_gG$ | $I_gM$ | $I_gA$ | EA | EBNA | MA[1] |
|---|---|---|---|---|---|---|
| NORMAL ADULTS | + | − | − | − | + | + |
| ACUTE ADULTS (EARLY) | ++ | + | − | + | − | − |
| CHRONIC INFECTION | + | + | − | ± | ± | ±? |
| REACTIVATION | + | + | − | + | + | + |
| XLP[2] | + | − | − | ± | (+) | ? |
| NPC | ++ | − | + | +(D) | + | ++ |
| BL | ++ | − | − | +(R) | + | + |

[2]XLP AS AN EXAMPLE OF IMMUNOLOGICALLY DEPRIVED HOSTS
[1]DETERMINED BYT IMMUNOPRECIPITATION OF GP 240/200
(MA; membrane antigen)

B. Convalescence: Disappearance of antibodies against EA and maintenance of antibodies against VCA and EBNA As the immune defense mechanisms of the body remove the lytically infected cells from the circulation, the antibody levels will start to fall during the convalescent phase. After a certain period, anti-EA-antibodies disappear. However, as mentioned above, EBV is produced in the parotid gland. The viral particles and intercellular virus-associated antigens including EA will be shed into the saliva and reach the oropharynx. Here the viral particles bind to the B-lymphocytes and are presented to the body as antigens, thus the antibody titer against VCA is maintained. Since EA cannot bind to the lymphocytes it will be degraded by proteases and therefore will not be available to the immune system as an antibody-inducing antigen.

The circulating lymphocytes that are latently infected by EBV contain EBNA. At the end of their life cycle these cells disintegrate and release EBNA into the blood stream. Therefore antibodies to this antigen will persist.

Thus, due to the EBV-production in the parotid gland and to the release of EBNA from latently infected B-cells, sera of convalescents will have low anti-VCA and anti-EBNA IgG-antibody levels (see Table A, supra). In addition EA released from rare B lymphocytes which may enter a lytic cycle may be an inferior antigen and may not give rise to antibody levels detectable with the test systems used.

In combination with the known sequence of appearance of antibody classes, specifically the early presence of IgM antibodies followed by IgG antibodies, the various antigen classes of primary disease caused by EBV can be utilized for improved diagnostic procedures. However, available test systems which are mainly based on cellular antigens or cell derived antigens nave serious limitations. This concerns the sensitivity, especially for detection of IgM antibodies and also unspecific reactions.

C. EBV-related antibodies in individuals suffering of NPC:

The first suggestive evidence that Epstein-Barr virus might be causally related to nasopharyngeal carcinoma and African Burkitt's Lymphoma was derived from serological data (for review see M. A. Epstein, B. G. Achong, "The Epstein-Barr Virus" Springer Verlag Berlin, Heidelberg, N.Y. (1979)).

Using mainly indirect immunofluorescence on cells producing virus or at least early viral antigens, significantly higher antibody titers to these antigens were found in patients' sera. These first tests which detected unspecified immunoglobulin classes against a group of proteins named Early Antigen (EA) and another group of proteins named Virus Capsid Antigens (VCA) were helpful for the establishment of a relationship between EBV and these diseases. These tests, however, are of limited value for definite diagnosis of the malignancies from a single serum, and cannot be used for monitoring therapy.

The introduction of antigen and antibody class specific tests, specifically the determination of peripheral IgA antibodies for the two antigen families EA and VCA and also the first attempts to subdivide at least the EA-family (EA, D or R; G. Henle, W. Henle and G. Klein, "Demonstration of 2 distinct components in the early antigen complex of Epstein-Barr Virus infected cells", Int. J. Cancer 8, p. 272 (1971)) achieved remarkable improvements* of the diagnostic and prognostic value of the tests.

In the areas of high risk for NPC, 1% of the adult population has IgA antibodies for EBV-Capsid antigen (VCA). Three percent of this group has NPC upon clinical examination and, with the exception of terminal cases, there were no anti-VCA IgA negative cases detected. Out of the IgA anti-VCA positives, about 1% per year developed NPC in a 3 year follow up. A test of this quality, if available as a highly specific automat-readable ELISA test, would provide an excellent "first step" screening for a population of extreme risk.

Detection of EB virus IgA/VCA antibody is helpful for diagnosis of NPC (see table on page 14), and of special value for the detection of early stages. For example, in Wuzhou City (China; high risk area for NPC), the frequency of NPC detected by serological mass survey revealed a much higher percentage of patients in stages I (42%) and II (48%) than otherwise detected in outpatient clinics (1.7% stage I and 30% stage II). The chance of survival is clearly related to the stage at which therapy is begun. The survival rates for stage I are (according to Shanghai Tumor Hospital) 93%, for stage II 75%, and are very low for more advanced stages. Therefore it is possible to reduce the mortality rate of NPC through early detection and early treatment.

IgA antibodies to the early antigen complex of EBV can be detected in 40% to 70% of NPC patients, depending on the method used. These antibodies are virtually absent in the non-tumorbearing population. Such test of the tumorbearing individuals should be of great importance for the decision to start therapy, and its value would be even higher if the sensitivity could be enhanced to allow detection of disease in closer to 100% of the tumor patients.

The detection rate of NPC among IgA/VCA antibody-positive individuals is 1.9% and that of IgA/EA individuals is 30–40%. These data indicate that the IgA/EA antibody test is more specific for the detection of NPC, but not as sensitive as IgA/VCA antibody.

A number of laboratories have used the continuous determination of IgA antibodies to EA and VCA to monitor the success of therapy and for early detection of relapse with very good success.

Membrane protein gp 250/350 and its use

Four proteins of the vital envelope constituting the so-called membrane antigen complex (MA) have been described (L. F. Qualtiere, G. R. Pearson, et. al., supra; J. North, A. J. Morgan, M. A. Epstein, "Observations on the EB virus envelope and virus-determined membrane antigen (MA) polypeptides", Int. J. Cancer 26, p. 231 (1980)). Two of these proteins, i.e. gp 250and gp 350, antigenically closely related (D. A. Thorley-Lawson and K. Geilinger, "Monoclonal antibodies against the major glycoprotein (gp 250/350) of Epstein-Barr virus neutralize infectivity", Proc. Natl. Acad. Sci. USA 77, p. 5307 (1980)). The molecular weight of one component ranges from 200,000 to 250,000 D depending on the cell line where the virus is derived from and the second antigenetically related glycoprotein has a molecular weight of 300,000–350,000 D but is absent in some cell lines. Since these glyco-proteins are all related in antigenicity, protein and encoding DNA sequence, they are usually referred to as gp 220/350 or gp 250/350 or simply as gp 250 or gp 350 but meaning the whole family of related glycoproteins.

Glycoprotein 250/350 is able to bind to the EBV receptor of human and some primate B-lymphocytes and to thus initiate the infection of these cells (A. Wells, N. Koide, G. Klein, "Two large virion envelope glycoproteins mediate Epstein-Barr virus binding to receptor-positive cells", J. Virol. 41, p. 286 (1982)). Antibodies against these proteins neutralize the infectivity of the virus, which could be demonstrated for human as well as for rabbit antisera and mouse monoclonal antibodies (D. A. Thorley-Lawson et. al., supra). By the use of monoclonal antibodies it has been shown that blocking of only one antigenic determinant present both in gp 350 and gp 250 was sufficient for virus neutralization. Adsorption of human sera to immobilized gp 350 and gp 250 removed the neutralizing antibodies (D. A. Thorley-Lawson et. al., supra). Thus, there is convincing evidence that a) gp 350 and gp 250 induce the production of neutralizing antibodies, and that b) antibodies against gp 350 and gp 250 have neutralizing capacity.

Therefore, this protein as well as its related viral gene product, gp 350 (with a molecular weight of 350,000), are candidates for a possible EBV vaccine (A. J. Morgan, M. A. Epstein, J. R. North, "Comparative immunogenicity studies on Epstein-Barr virus membrane antigen (MA) gp 34o with novel adjuvants in mice, rabbits and cotton-top tamarins", J. Med. Virol. 13, p. 281 (1984)). These glycoproteins are expressed on induced EBV producer cell lines and can be easily demonstrated after radioiodination of cell surface proteins (L. F. Qualtiere, G. R. Pearson, "Epstein-Barr virus-induced membrane antigens: immunochemical characterization of Triton X-100 solubilized viral membrane antigens from EBV superinfected Raji cells", Int. J. Cancer 23, p. 808 (1979)).

Application of gp 250/350 for the diagnosis of EBV-related diseases

IgG antibodies are absent during the acute phase of primary EBV infection, but present for lifetime after convalescence. IgM antibodies are present in the early stage of the disease and absent during convalescence.

IgA antibodies against EBV-antigens are present almost exclusively in NPC patients and can be detected in sera of at least 58% of these patients even with not very sensitive tests (Zeng Yi and Hans Wolf, manuscript in preparation and example 16, infra).

Comparison of Positive Rate of IgG and IgA Antibodies
to VCA and MA from NPC Patients and Normal Individuals

|  | MA/IgG | | MA/IgA | | VCA/IgA | | EA/IgA | |
| --- | --- | --- | --- | --- | --- | --- | --- | --- |
| Cases | (+) No. | (+) rate % | (+) No. | (+) rate % | (+) No. | (+) rate % | (+) No. | (+) rate % |
| NPC Patients 48 | 48 | 100 | 28 | 58.3 | 48 | 100 | 31 | 64.6 |
| Normal Individuals 48 | 47 | 97.9 | 0 | 0 | 0 | 0 | 0 | 0 |

*MA/IgG and MA/IgA detected by immunofluorescence test
VCA/IgA and EA/IgA detected by immunoenzymatic test The whole gp 250 molecule or parts of its backbone polypeptide chain can be utilized as reagents in preferentially class-specific antibody detection tests such as passive hemagglutination, counter gel electrophoresis, radioimmunoassays or enzyme-linked immuno-absorbent assays.

Highly specific test antigens allow better signals and detect otherwise unrevealed low antibody levels of clinical significance. The use of singular antigenic sites of the gp 250 instead of the entire gene product may, in some cases, permit a more precise diagnosis of the disease.

Application of gp 250/350 for prophylaxis and treatment of EBV-related disease s A. Since infection by EBV early in life only causes sub-clinical servoconversion, it may be anticipated that the presence of maternal antibodies or antibodies induced by a vaccine will influence the clinical manifestation of a primary EBV infection. It is expected that the vaccination of children or young adults, preferably before the peak of risk of catching an EBV infection, reduces effectively the clinical manifestation of infectious mononucleosis in the population.

B. In all areas with high incidence rates for NPC or BL, the population shows almost 100% seroconversion to EBV within the first one to two years of life. Vaccination will have to take place soon after birth. If this vaccination is regularly repeated, it will in all probability prevent EBV infection, delay it or reduce the biological effects of early primary infection. Each of these consequences is expected to either prevent the subsequent development of neoplasia, to delay its onset considerably or to decrease the relative risk.

C. In NPC, occasional production of viral antigens at the site of the tumor will stimulate primarily IgA secreting B-lymphocytes. IgA antibodies are capable of blocking antibody-mediated cytotoxicity. IgA antibodies to viral membrane antigens, such as gp 250, are present in NPC and BL patients and may not only be indicators of the disease, but may even contribute to the failure of the immune system to eliminate the tumor cells by their masking potential. Large doses of the purified antigen given to tumor patients may bind IgA and initiate the formation of an excess of IgG antibodies directed to the same antigen. These specific IgG antibodies may then compete with remaining IgA antibodies and allow the elimination of tumor cells by antibody-dependent mechanisms.

D. Appropriate administration of gp 250 or related products might also enhance the cellular immune mechanisms and thus restrict the growth of tumors.

Production of EBV specific antigens according to the present invention

1. As a consequence of all findings, it is one of the objects of this invention to improve the sensitivity of tests for detection of antibody classes and antigen specific antibodies and to develop a system which allows mass testing and better standardization.

2. EBV cannot be efficiently produced in a lytic cell cycle since efficiently infectable cells are not known at present and because all of the cells used as source for the preparation of EBV or related antigens are immortalized cells or even tumor derived cells. In most cell lines retroviruses have been demonstrated. The products isolated from such cultures therefore are not only very expensive but their use is also a potential safety risk.

3. The application of recombinant DNA technology has made possible the production of useful polypeptides by appropriate host cells transformed with recombinant DNA molecules and grown in appropriate culture systems.

4. According to the present invention, recombinant DNA methods are used to express the genetic information of the genes or at least of parts of the genes encoding the EBV proteins p138, p150 and gp 250/350 in appropriate host cells, such as bacteria (e.g. the genera Escherichia, Salmonella, Pseudomonas or Bacillus), yeasts (e.g. the genera Candida, or Saccharomyces) and mammalian cells (e.g. Vero-cells, CHO-cells or lymphoblastoid cell lines).

5. Furthermore, the genomic regions encoding the EBV proteins p150, p143, p138, p110, p105, p90, p80 and p54 were identified and their relevance for diagnostic purpose has been identified. Therefore, the key information for the production of these proteins or antigenic determinants thereof in a manner as demonstrated for the proteins p138, p150 and gp 250/350 is also disclosed in the present invention.

Recombinant DNA technology

A. Expression control systems

Prokaryotes most frequently are represented by various strains of *E. coli*. However, other microbial strains may also be used, such as bacilli, for example *Bacillus subtilis*, various species of Pseudomonas, or other bacterial strains. In such prokaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al., Gene 2, p. 95 (1977). pBR322 contains genes for ampicillin and tetracycline resistance, and these markers can be either retained or destroyed in constructing the desired vector. Commonly used prokaryotic control sequences which are defined herein to include promoters for transcription initation, optionally with an operator, along with ribosome binding site sequences, include such commonly used promoters as the beta-lactamase (penicillinase) and lactose (lac)

promoter systems (Chang, et. al. Nature 198, p. 1056 (1977)) and the tryptophan (trp) promoter system (Goeddel, et al., Nucleic Acids Res. 8, p. 4057 (1980). The lambda-derived $P_L$ promoter and N-gene ribosome binding site (Shimatake et al., Nature 292, p. 128 (1981), which has been made useful as a portable control cassette are further examples. However, any available promoter system compatible with prokaryotes can be used.

In addition to bacteria, eukaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (J. R. Broach, Meth. Enz. 101, p. 307 (1983)), other plasmid vectors suitable for yeast expression are known (see, for example, Stinchcomb et al., Nature 282, p. 39 (1979); Tschempe et al., Gene 101, p. 157 (1980) and L. Clarke et al., Meth. Enz. 101, p. 300 (1983)). Control sequences for yeast vectors include promoters for the synthesis of glycolytic enzymes (Hess et. al., J. Adv. Enzyme Reg. 7, p. 149 (1968); Holland et al., Biochemistry 17, p. 4900 (1978)). Additional promoters known in the art include the promoter for 3-phosphoglycerate kinase (Hitzeman et al., J. Biol. Chem. 255, p. 2073 (1980)), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosohate isomerase, phosphoglucose isomerase, and glucokinase. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

Evidence suggests that terminator sequences are desirable at the 3' end of the coding sequences. Such terminators are found in the 3' untranslated region following the coding sequences in yeast-derived genes. Many of the vectors illustrated contain control sequences derived from the enolase-I gene containing plasmid peno46 (M. J. Holland et al., J. Biol. Chem. 256, p. 1385 (1981)) or the LEU 2 gene obtained from YEp13 (J. Broach et al., Gene 8, p. 121 (1979)), however, any vector containing a yeast-compatible promoter, origin of replication and other control sequences is suitable.

It is also, of course, possible to express genes encoding polypeptides in eukaryotic host cell cultures derived from multicellular organisms. See, for example, Cruz and Patterson, editors, "Tissue Cultures", Academic Press (1973). Useful host cell lines include VERO and HeLa cells, and Chinese hamstar ovary (CHO) cells. Expression vectors for such cells ordinarily include promoters and control sequences compatible with mammalian cells such as, for example, the commonly used early and late promoters from Simian Virus 40 (SV 40) (Fiers et al., Nature 273, p. 113 (1978)), or other viral promoters such as those derived from polyoma, Adenovirus 2, bovine papiloma virus, or avian sarcoma virusses. General aspects of mammalian call host system transformations have been described by Axel in U.S. Pat. No. 4,339,216 issued Aug. 16, 1983 it now appears also than "enhancer" regions are important in optimizing expression; these are, generally, sequences found frequently upstream of the promoter region. Origins of replication may be obtained, if needed, from vital sources. However, gene integration into the chromosame is a common mechanism for DNA replication in eukaryotes, and hence independently replicating-vectors are not required. Plant cells are also now available as hosts, and control sequences compatible with plant cells such as the nopaline synthase promoter and polyadenylation signal sequences (A. Depicker et al., J. Mol. Appl. Gen. 1, p. 561 (1982)) are available.

B. Transformation of suitable hosts

Depending on the host cell used, transformation is done using standard techniques appropriate to such cells. The calcium treatment employing calcium chloride, as described by S. N. Cohen, Proc. Natl. Acad. Sci. (USA) 69, p. 2110 (1972) is used for prokaryotes or other cells which contain substantial cell wall barriers. Infection with *Agrobacterium tumefaciens* (C. H. Shaw et al., Gene 23, p. 315 (1983)) is used for carmain plant cells. For mammalian cells without such cell walls, the calcium phosphate precipitation method of Graham and van der Eb (Virology 52, p. 546 (1978)) is preferred. Transformations into yeast are carried out according to the method of P. van Solingen et al. (J. Bact. 130, p. 946 (1977)) and C. L. Hsiao et al. (Proc. Natl. Acad. Sci. (USA) 76, p. 3829 (1979)). Alternatively, the procedure of Klebe, et al. (Gene 25, p. 333 (1983)) can be used.

C. Construction of recombinant cloning and expression vectors

Construction of suitable vectors containing the desired coding and control sequences employs standard ligation and restriction techniques which are well understood in the art. Isolated plasmids, DNA sequences, or synthesized oligodeoxyribonucleosides are cleaved, tailored and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog.

If desired, size separation of the cleaved fragments may be performed by polyacrylamide gel or agarose gel electrophoresis using standard techniques. A general description of size separations is found in "Methods in Enzymology" 65, p. 499–560 (1980).

Restriction cleaved fragments may be blunt ended by treating with the large fragment of *E. coli* DNA polymerase I (Klenow) in the presence of the four deoxynucleotide triphosphates (dNTPs). The Klenow fragment fills in at 5' sticky ends but chews back protruding 3' single strands, even though the four dNTPs are present. If desired, selective repair can be performed by supplying only a selected one or more dNTPs within the limitations dictated by the nature of the sticky ends. Treatment under appropriate conditions with S1 nuclease results in hydrolysis of any single-stranded portion.

Synthetic oligonucleotides may be prepared by the triester method of Matteucci et al. (J. Am. Chem. Soc. 103, p. 3185 (1981)) or the diethylphosphoramidite method of Caruthers, described in U.S. Pat. No. 4,415,732, issued Nov. 15, 1983.

Ligations are performed under standard conditions and temperatures (as described below) using T4 DNA ligase. In vector constructions employing "vector fragments", the vector fragment is commonly treated with bacterial alkaline phosphatase (BAP) in order to remove the 5' phosphate and prevent religation of the vector. BAP digestions are carried out under standard conditions (as described below).

D. Selection of transformants

In the constructions correct ligations for plasmid construction are confirmed by transforming *E. coli* or other suitable hosts with the ligation mixture. Successful transformants are selected by ampicillin, tetracycline or other antibiotic resistance or using other markers depending on the mode of plasmid construction, as is understood in the art.

BRIEF SUMMARY OF THE INVENTION

The present invention relates to the production of EBV specific antigens by recombinant DNA technology and their use in diagnosis, prophylaxis and therapy of EBV-related dieseases. Therefore, it is an object of this invention to identify novel Epstein-Barr viral antigens, such as p150, p143, p138, p110, p105, p90, p80, p54 (G. J. Bayliss, H. Wolf, infra), which are correlated with Epstein-Barr virus related diseases like nasopharyngeal carcinoma (NPC), infectious mononucleosis, and Burkitt's lymphoma (see legend to FIG. 1 and FIG. 28) by immunological methods.

Another object of this invention is the localization and identification of genomic regions of EBV, for example as it has been cloned from B95-8 cells (American Type Culture Collection, Rockville, Md., USA (ATCC) CRL1612) (J. Skare, J. L. Strominger, "Cloning and mapping of BamHI endonuclease fragments of the DNA from the transforming B95-8 strain of Epstein-Barr Virus", Proc. Natl. Acad. Sci. USA 77, p3860(1980)) coding for said antigens of diagnostic importance and of relevance for medical purposes. This is achieved by using the hybrid selection method.

A further object of the present invention is the sub-cloning of a genomic region of EBV, for example from existing libraries of EBV, cloned from B95-8 cells which encodes at least a part of useful antigens for medical purposes, such as p138 and p150. This is achieved by joining a subgenomic fragment, e.g. an XhoI-fragment, derived from the EBV B95-8 subclone pBR322 BamA, (J. Skare et al., supra) to the plasmid pUC8 (J. Messing, infra) (puC635, see FIG. 4A).

Another object of this invention is the production of proteins by expression of the respective genetic information in suitable host cells, such as bacteria (e.g. of the genera Escherichia, Salmonella, Pseudomonas or Bacillus), yeasts (e.g. of the genera Candida or Saccharomyces) animal cells and human cells (e.g. Vero-cells; CHO-cells; CHO dhfr⁻ cells in combination with an appropriate selection system, optionally a plasmid carrying a functional dhfr gene as well as the genetic information for the EBV gene under control of a suitable regulation sequence; or lymphoblastoid cell lines). The proteins produced by these host cells contain e.g. p138, p150 or gp250/350-related antigenic determinants (epitopes) and are, depending on the expression system, synthesized either as a fusion protein or as a non-fusion protein.

For the production of a fusion protein by bacteria the expression of the genomic subfragments, for example that encoding a part of p138 of EBV B95-8 and introduced into the known plasmid pUC8, was induced e.g. by isopropyl-β-D-thioglactopyranoside (IPTG). The respective expression products were identified by immunological methods.

Another fusion protein is provided by cleaving subclone pUC635 with EcoRI and BglII and introducing this fragment into the vector plasmid pUC9 (U. Rüther, infra). The resulting recombinant plasmid is pUC924 (FIG. 6). The expression product has a size of about 94 kd.

A further fusion protein is produced by expressing the genetic information of said Xhoi-p138-encoding fragment of pBR322 BamA in the plasmid pEA305 (E. Amann, J. Brosius, M. Ptashne, "Vectors bearing a hybrid trp-lac-promoter useful for regulated expression of cloned genes in E. coli", Gene 25, p. 167 (1983)). After putting the p138 related information into a proper reading frame relative to pEA305, the clone pMF924 synthezises a fusion protein that contains a part of the λ-repressor protein $c_1$ (FIG. 7).

Still another fusion protein is provided by cloning a 3.0 kb genomic XhoI-fragment containing p138-related genetic information 3' to a hybrid trp-lac promoter (as described by F. Amann et. al., supra). Forth is purpose the known plasmid pKK240-11 was used. The resulting clone pKK378 synthezises a fusion protein that is composed of an aminoterminal methionine residue followed by p138 related DNA sequences (FIG. 8).

Still another object of the present invention is to provide fusion proteins, non-fusion proteins or oligopeptides which contain only the antigenic determinant protein sub-regions of viral proteins like p138. For this purpose the determinants of the protein are located by a computer-directed analysis, using a computer program developed by us for the Digital Equipment VAX 11/750 computer. A similar program has been used for other problems and another computer by G. H. Cohen, B. Dietzschold, M. Ponce de Leon, D. Long, E. Golub, A. Varrichio. L. Pereira, R. J. Eisenberg, "Localization and synthesis of an antigenic determinant of Herpes simplex virus glycoprotein D that stimulates the production of neutralizing antibody", J. Virol 49, p. 102 (1984). By cloning the respective fragments into vectors like pUC8 or pUR288 (U. Rüther et al., infra) plasmids as pUR600 and pUR540 were obtained. The produced large and small fusion proteins are investigated by gel electrophoresis and immunoblotting experiments. The cloning experiments in pUR288 were done for stabilizing the small p138-related polypeptides.

A further object of the present invention is the expression of polyantigens composed of antigenic determinants of several different EBV-serotypes. For that purpose the corresponding DNA fragments are linked and introduced in a suitable vector. The expression products are fusion and non-fusion EBV-specific polyantigens.

In particular, the invention relates to polyantigen fusion proteins, comprising at least two of the EBV proteins of the invention, wherein the proteins are encoded by DNA sequences corresponding to a single EBV serotype. The invention also relates to polyantigen fusion protein, comprising at least two of the EBV proteins of the invention, wherein the proteins are encoded by DNA sequences corresponding to different EBV serotypes.

Further fusion proteins containing p150-related antigenic determinants were obtained by cloning and expression of the corresponding DNA sequences in pUR plasmids and pUC plasmids. The obtained constructs were the recombinant plasmids pUR290CXH580, pUR290DBX320, pUR292DBB180, pUR288DTT700, pUR288DTT740, pUR290DTP680, and pUR288DPP320.

Another object of the present invention is the construction of new expression vectors, such as pUC600 and pUC601 which contain a part of the coding region of the viral protein p138. If DNA sequences are introduced 3' to this sequence into the vector, the expression products are stabilized by the p138-specific aminoacid sequence and protected against protease degradation.

Still another object of this invention is the modification of said expression vectors by introducing a DNA-sequence coding for three to fifteen Arginine residues and at least one stop codon 3' of the cloning site of said expression vectors and furthermore positioned in an appropriate reading frame. The obtained vector is pUCARG601. If DNA-sequences coding for proteinaceous material are inserted into this expression vector the expression products will be fusion proteins carrying said Arginine residues at their carboxy terminus, such as those fusion proteins encoded by plasmids pUCARG1140 (see FIG. 12a)) and pUCARG680.

Thus it is an object of this invention to provide a simple method for isolating proteins useful for diagnosis, prophylaxis and therapy such as EBV p138 or related polypeptides or oligopeptides (antigens) from the host cell lysate according to the method of H. M. Sassenfeld, S. J. Brewer ("A polypeptide fusion designed for the purification of recombinant proteins", Bio/Technology 2, p. 76 (1984)).

By introducing Arginine residues the net charge of the expressed proteins becomes more positive and after lysis of the host cells the oligo-arginine linked proteins are isolated by a SP SEPHADEX C-25 column chromatography. Due to the oligo-arginine group the EBV specific proteins are eluted at a high NaCl-concentration. This eluate is then treated with carboxypeptidase B which degrades carboxy-terminal lysine and arginine residues. Finally another SP SEPHADEX C-25 chromatography is carried out wherein the EBV-related proteins are eluted at low salt concentrations (see FIG. 16). It is evident, however, that this procedure may be used also for the purification of proteins secreted into the medium.

It is also evident that other established methods for protein-purification such as molecular sieving or affinity chromatography on ion exchange columns or columns loaded with specific antibodies to the expressed proteins can be used as additional or alternate purification methods. For the production of non-fusion proteins which essentially contain amino acid sequences of the naturally occurring proteins or parts thereof the recombinant plasmids of the present invention may be modified. If an oligonucleotide linker is inserted between the bacterial protein encoding region and the EBV-related protein encoding region of the expression vector, the amino acid sequence corresponding to the oligonucleotide linker becomes part of the expressed fusion protein. After isolation of this fusion protein from the transformants expressing it, it is cleaved either by amino acid sequence specific proteases in the introduced aminoacid linker or, if the amino acid linker comprises peptide bonds sensitive to acid cleavage, by treatment with acids, e.g. formic acid.

A further object of this invention is the cloning of a genomic region of EBV coding for at least a part of the specific viral antigen gp 250 and gp 350. This is achieved by joining a subgenomic PstI-PstI fragment of the EBV genome from the cell strain B95-8 (ATCC CRL 1612) (R. Baer et al., infra) contained in pBR322 BamL (J. Skate et al, supra) to the plasmid pUC8 (J. Messing et al., infra). The resulting recombinant plasmid is designated as pUCLP1.9 (see FIG. 19).

For the production of a fusion protein by bacteria, a genomic subfragment coding for a part of gp 250 and gp 350 of EBV B95-8 was cloned into the vector pUR 290 (U. R uther et al., infra) which carries a region of the lacZ gene coding for the enzyme β-galactosidase (pURLP1.9, see FIG. 20). The respective expression product was purified and identified by immunological methods.

Still another object of the present invention is to provide fusion proteins or non-fusion proteins which contain only the antigenic determinant protein subregions of gp 250 and gp 350. For this purpose the antigenic determinants of the proteins were localized by a computer-directed analysis using a computer program developed by us for the Digital Equipment VAX 11/750 computer.

The respective DNA-fragments are then cloned in a conventional expression vector such as pUR (β-galactosidase) (U. Rüther, et al., infra). Plasmids obtained were e.g. pURLEP600 and pURLXP390 (see FIG. 27). Furthermore, the N-terminal antigenic determinant of gp250/350 was expressed as a fusion protein in a pUC vector (pUCLEP600, see FIG. 27). Another fusion protein is provided by cloning a DNA-fragment coding for the N-terminal antigenic determinant of gp 250 and gp 350 into the expression vector pUCARG601 mentioned above.

A further object of the present invention is the expression of polyantigens containing several antigenic determinants of gp 250 and gp 350 located by said computer analysis. For this purpose the corresponding DNA fragments are linked and introduced in a suitable vector. The expression products are fusion and non-fusion EBV-specific polyantigens.

A final object of the present invention is the utilization of either said EBV-related proteins or subregions thereof or, if suitable, EBV-related DNA fragments or clones, for the production of diagnostic compositions (kits) useful in clinical diagnosis or scientific research. These tests are based on principles as ELISA (Enzyme-linked immunosorbent assay), RIA (Radio immuno assay) or the indirect hemagglutination assay. Furthermore, the EBV-related proteins can be used, e.g. for monitoring vaccination programs, analyzing epidemiological problems, for patients treatment, and for the production of vaccines for prophylaxis and therapy of EBV-related diseases, such as mononucleosis, Burkitt's lymphoma and nasopharyngeal carcinoma. Vaccines can be manufactured according to conventional methods. Unit doses are filled in vials optionally together with a conventional adjuvant such as aluminium hydroxide. Alternatively the product may be administered in the form of aggregates with liposomes. Patients may be vaccinated with a dose sufficient to stimulate antibody formation and revaccinated after one month and after 6 months.

Finally the proteins are useful for prophylaxis and therapy of EBV-related diseases, because they are able to modulate the immune response in patients suffering from diseases such as NPC, chronic infectious mononucleosis or EBV-related Burkitt's lymphoma.

The immunoprecipitated $^{35}$S-labelled proteins were separated by a SDS-polyacrylamide gel electrophoresis and an X-ray-film was exposed to the gel.

The sources of the different sera used for precipitation are given at the bottom of the respective regions of the autoradiography. The control, designated "pool", contains all of the immunoprecipitatable EBV-specific proteins.

It can be taken from the autoradiography that at least antibodies to p138, p105 and p80 are present in each of the NPC sera and only in some of the other EBV-infection specific sere. In analogy, antibodies to p54 are significant for fresh EBV infection (infectious mononucleosis) as compared to convalescent state. Antibodies to p150, p143, p.110, p90 are also present in convalescent sera of healthy individuals and can serve as markers for immunity or, in connection with IgM specific tests, for fresh EBV infection or, in connection with IgA, for a specific test for EBV-related neoplasia (NPC and BL).

Figure 2:
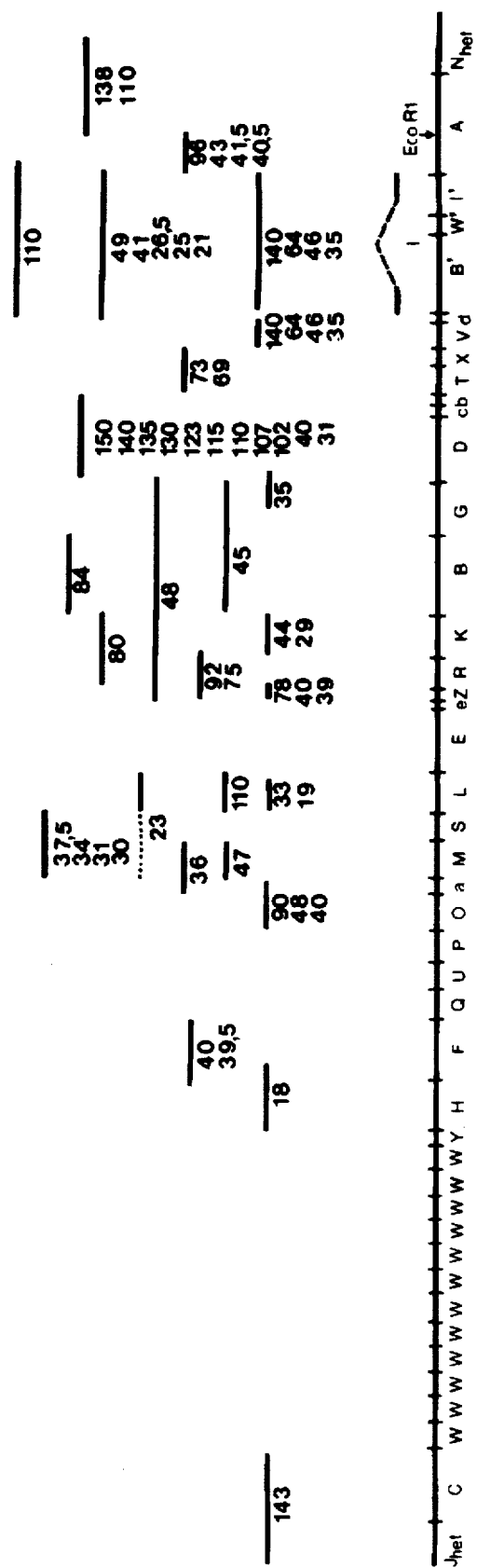

FIG. 2: Mapping of mRNA's relative to the EBV B95-8 genome.

The BamHI restriction sites of the EBV B95-8 genome are given at the bottom of the figure and the respective restriction fragments are designated by upper and lower case letters. The mRNA's of the proteins localized by hybrid-selection to individual BamHI restriction fragments are indicated by numbers and lines.

It can be taken from the figure, that the gene of p138 was correlated to the BamA-fragment.

FIGS. 3A–3I: DNA sequence of the leftward reading frame of BamA encoding p138.

The sequence shown is the respective negative strand. The p138 encoding region starts at nucleotide position 1 and ends at nucleotide position 3384. Restriction sites used for cloning of fragments of this coding region are indicated.

Figure 4A:
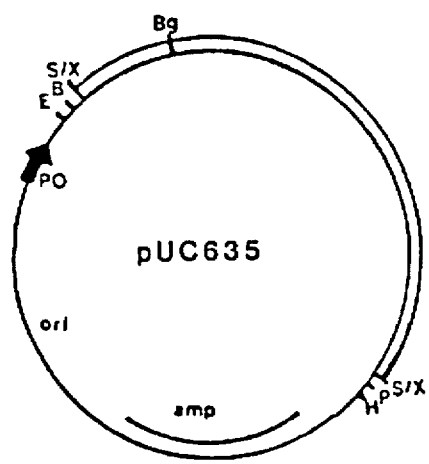
Figure 4B:
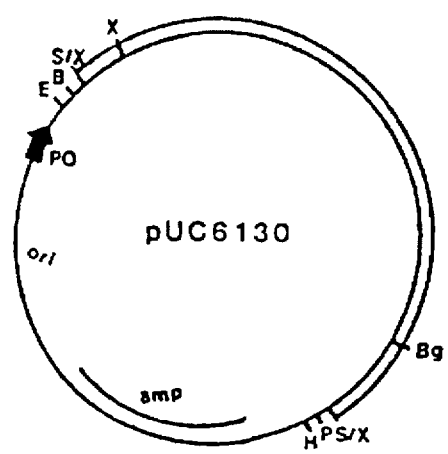

FIGS. 4A–4B: Restriction map of the plasmids pUC635 and pUC6130.

The size of the vector pUC8 is 2.7 kb. The cloning site 3' of the lacUV5 β-galactosidase promoter and operator (PO) contains EcoRI(E), BamHI(B), SalI(S), PstI(P), and HindIII (H) site. The β-lactamase gene is indicated by AMP. The 3.0 kb and 3.3 kb XhoI-fragments of the p138 coding region are inserted into the SalI site of pUC8. The insertion is indicated by an open bar. pUC635 contains the 3.0 kb XhoI-fragment in a correct reading frame relative to the β-galactosidase gene, whereas pUC613o contains the 3.3 kb Xhoi-fragment in the opposite orientation.

Figure 5:
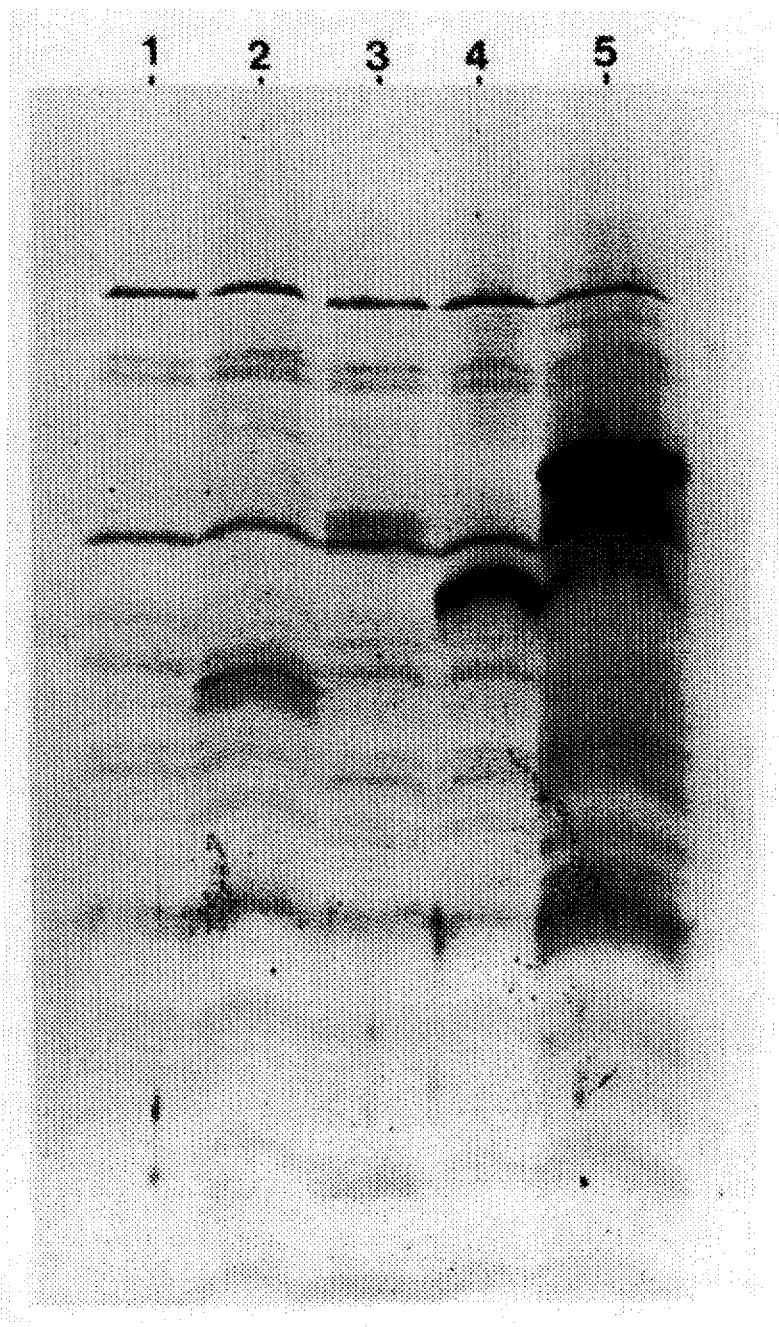

FIG. 5: Expression of the proteins encoded by plasmids pUC635, pUC924, pMF924, and pKK378.

Lane 1: of the immunostained Western-blot shows the proteins isolated from bacteria transformed with pUC8 and induced with IPTG.

Lane 2: proteins of pUC924 transformed bacteria

Lane 3: proteins of pKK378 transformed bacteria

Lane 4: proteins of pMF924 transformed bacteria

Lane 5: proteins of pUC635 transformed bacteria

The size of the fusion protein was estimated to be 75 kD (lane 2), 110 kD (lane 3), 90 kD (lane 4) and 135 kD (lane 5).

Figure 6:
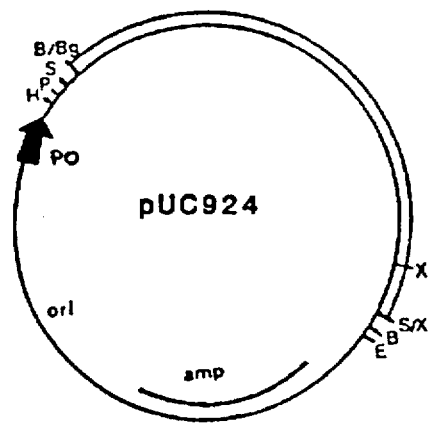

FIG. 6: Restriction map of the plasmid pUC924.

The size of the vector pUC9 is 2.7 kb. The cloning site 3' of the lacUV5 β-galactosidase promoter and operator (PO) contains an EcoRI(E), BamHI(B), SalI(S), PstI(P), and HindIII(H) site. The β-lactamase gene is indicated by AMP. The 2.6 kb BglII/EcoRI-fragment of pUC635 is inserted between the BamHI and EcoRI sites. The abbreviation of BglII is "Bg".

Figure 7:
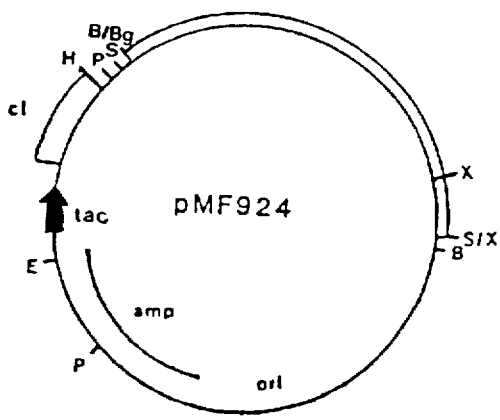

FIG. 7: Restriction map of the plasmid DMF924.

The 2.6 kb BamHI/HindIII-fragment of pUC924 was inserted into the BamHI and HindIII restriction sites of pEA305 which are located 3' of the hybrid trp-lac promoter (tac) and the aminoterminal coding region of $c_1$ (λ-repressor).

Figure 8:
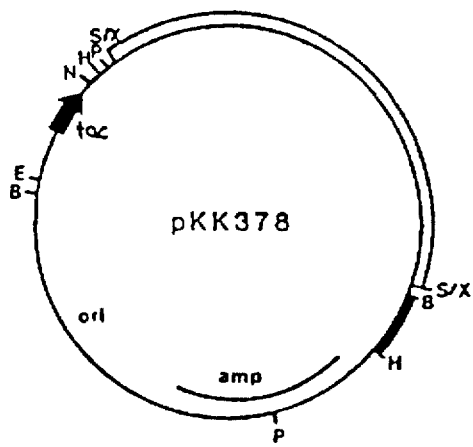

FIG. 8: Restriction map of the plasmid pKK378.

The 3.3 kb BamHI/HindIII-fragment of pUC6130 was inserted into the HindIII-site of the vector pKK240-11 using a 345 bp BamHI/HindIII-fragment of pBR322 as a linker (which is indicated by a heavy black line). Thus the p138 encoding fragment is located 3' of the hybrid trp-lac promoter (tac) and an ATG start codon.

Figure 9A:
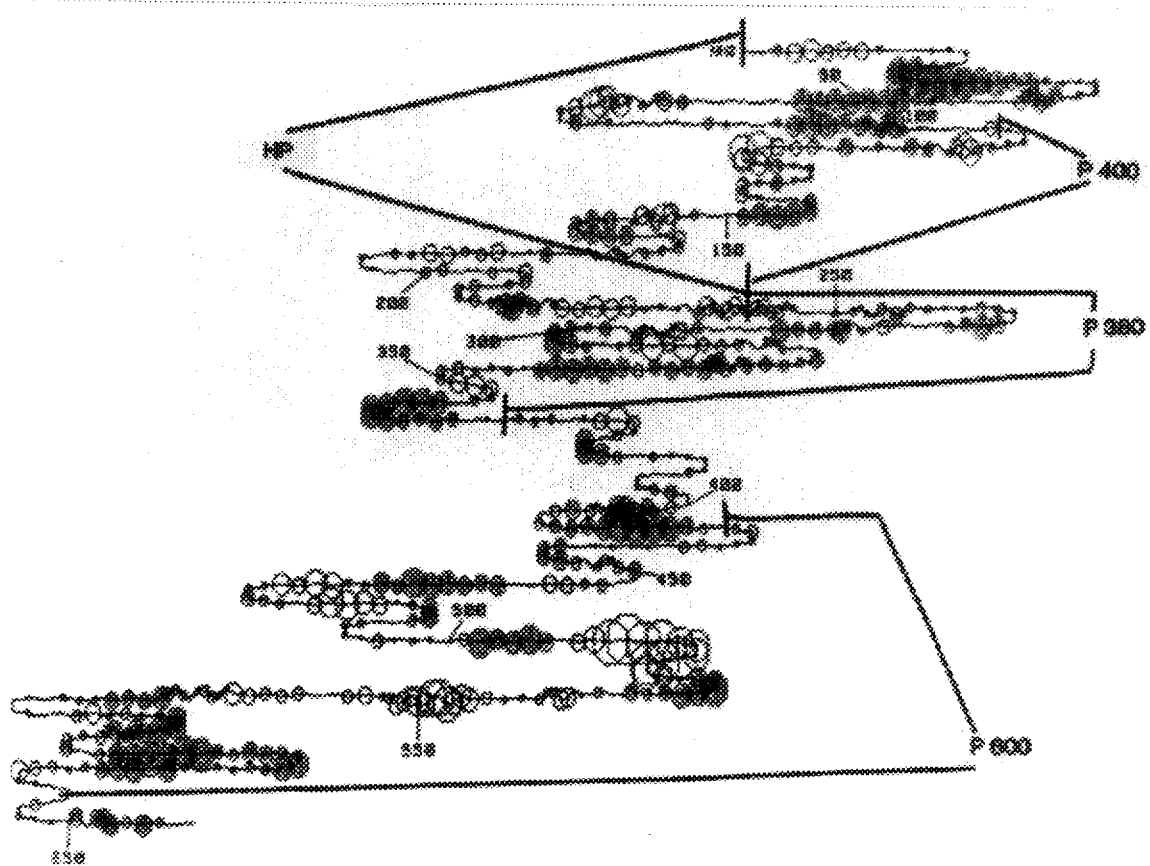
Figure 9B:
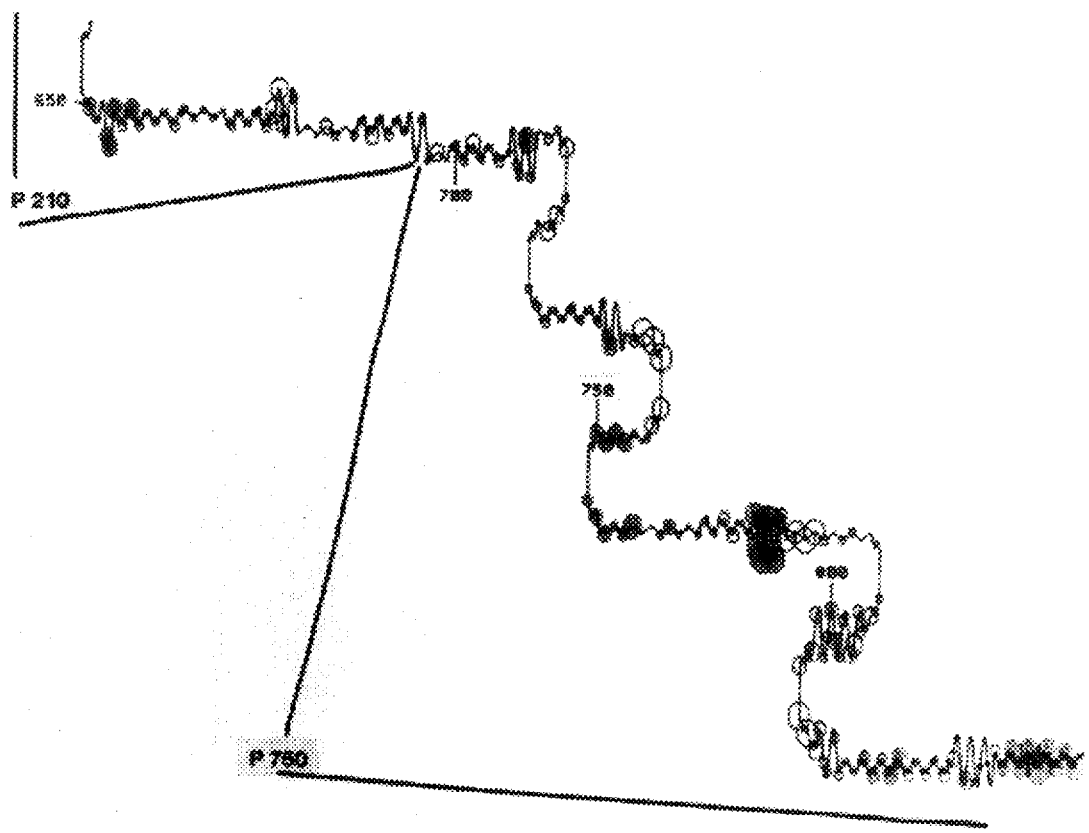

FIGS. 9A, B and C: Secondary structures of p138.

Computer plot of Chou-Fasman calculation of the p138 secondary structure. Additionally, the hydrophobic (closed circles) and hydrophilic (open circles) regions are indicated.

Antigenic sites can be expected in hydrophilic regions with a β-turn. This situation is given in the p600 region and at the carboxy-terminus of the protein.

The regions subcloned into the vectors pUC8 and pUR288 are indicated.

Figure 10A:
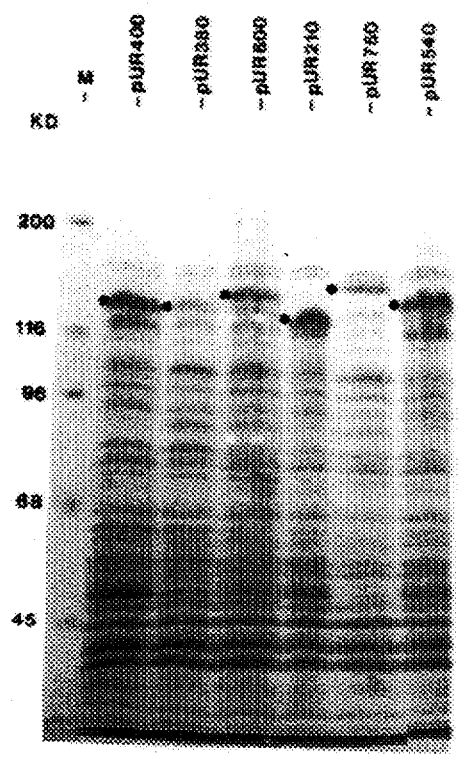
Figure 10B:
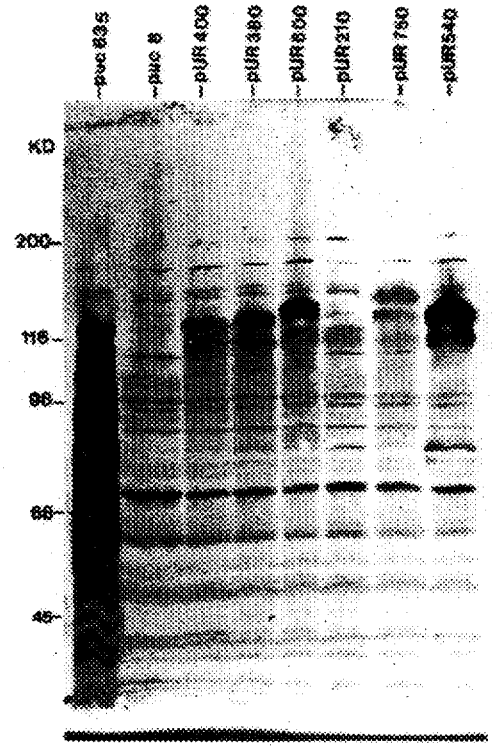

FIGS. 10A and 10B: Expression products of bacteria transformed with the plasmid pUR carrying PstI fragments of p138.

FIG. 10A. A coomassie brilliant blue stained SDS polyacrylamide slab gel analysis of lysates of IPTG induced bacteria carrying the various plasmids is shown. Fusion proteins with molecular weights between 120 and 150 kd are indicated with a closed circle. Track M molecular weight markers tracks pUR400–pUR540 lysates of bacteria carrying plasmids containing the regions of p138 as shown in FIGS. 3A–3I.

FIG. 10B. An enzyme-linked immunoassay of proteins transfered from a gel (similar to that shown in panel A) onto nitrocellulose paper (Western blot) is shown. In this assay a pool of high tirered antiserum was used and after washing, the bound immunoglobulins were visualized by sequential reaction with peroxidase coupled to antibodies against human IgG and diaminobenzidine. Only fusion proteins from bacteria containing pUR600 and pUR540 show specific reactions. Plasmid pUC635 (as a positive control) contains almost the whole of p138 coding region, however the protein is unstable and is rapidly degraded. pUC8 is the negative control containing the vector plasmid free from EBV derived sequences.

Figure 11:
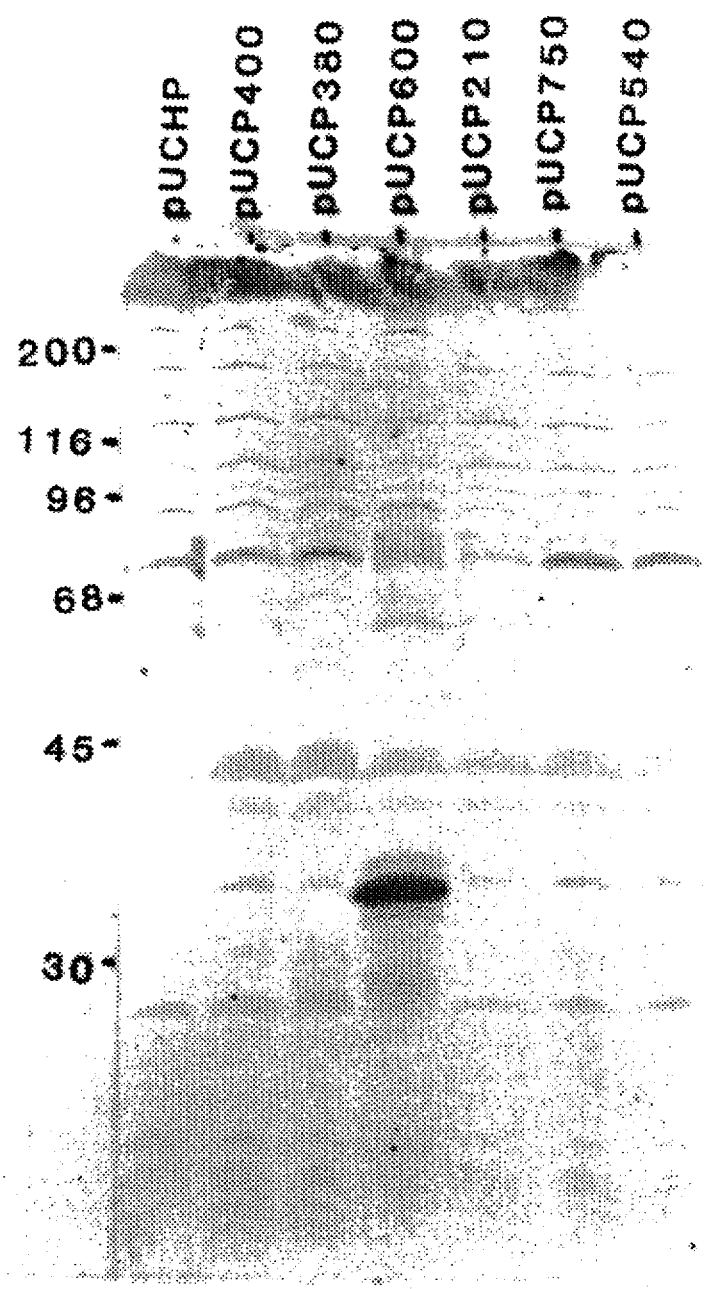

FIG. 11: Expression product of bacteria transformed with the pUC subclones carrying PstI-fragments of p138.

An enzyme-linked immunoassay of proteins electrophoretically transfered from a gel onto nitrocellulose paper (Western blot) was carried out. In this assay a pool of high titered antiserum was used and after washing, the bound immunoglobulins were visualized by sequential reaction with peroxidase coupled to antibodies against human IgG and diaminobenzidine. The fusion protein from bacteria containing pUCP600 was stably produced and shows a specific antigenic reaction.

Figures 12A, 12B:
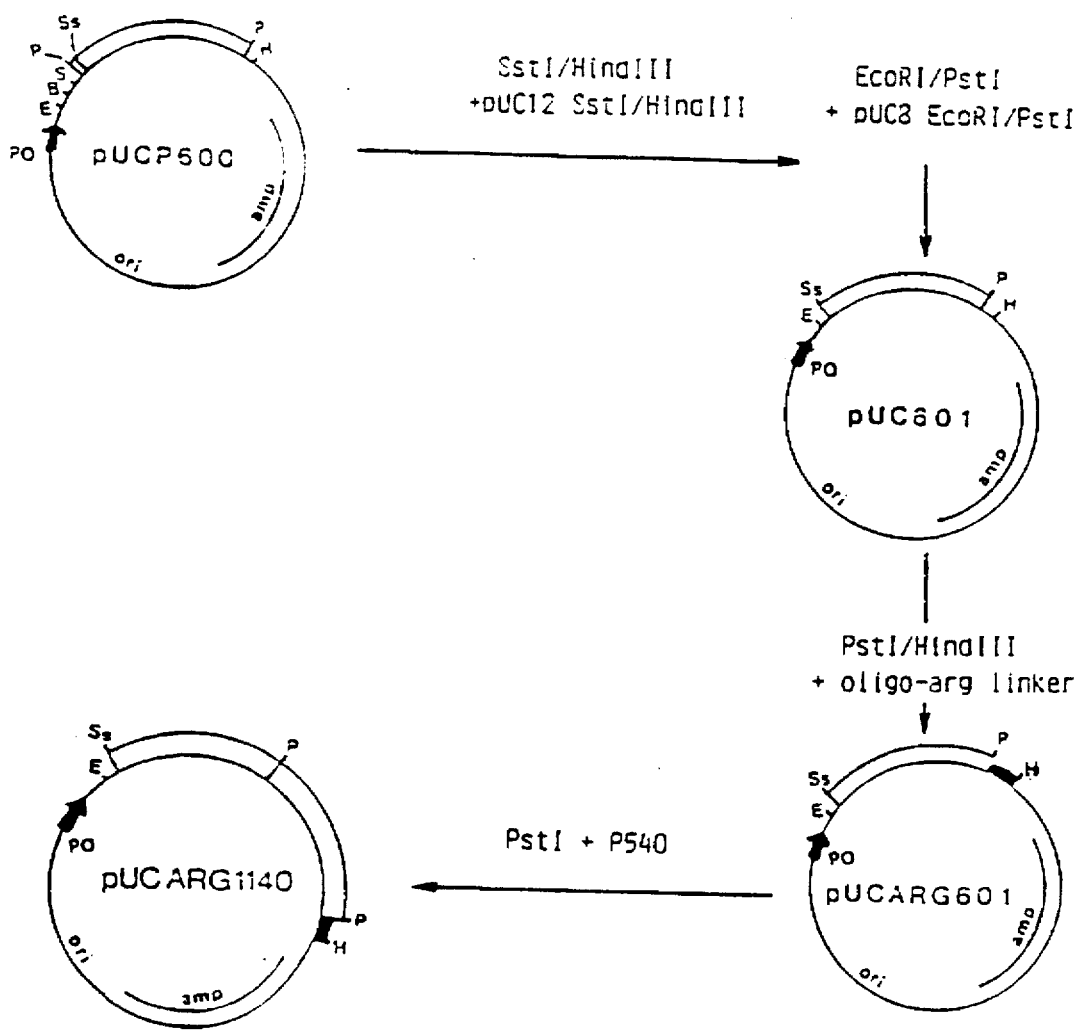

FIGS. 12A and 12B: Construction scheme for plasmid pUCARG1140 encoding both antigenic sites found by expression as β-gal fusion proteins FIG. 12A The 5'-PstI site in pUC600 was removed by digesting with SstI (20 bp upstream) and HindIII followed by the ligation with pUC12-SstI/HindIII. From this plasmid the insert was removed with EcoRI and PstI and ligated into pUC8-EcoRI. An oligonucleotide coding for five arginines and two stop codons was inserted into the resulting plasmid pUC601 as single-stranded DNA between the 3'-PstI site and HindIII (pUCARG601). In a last step the 540 bp PstI fragment encoding the second antigenic determinant from the C-terminus of p138 was inserted by digestion with PstI and ligation. The resulting plasmid contained both antigenic sites in frame followed by five arginine-residues. It was designated as pUCARG1140.

FIG. 12B Nucleotide sequence of the oligoarginine linker. The lower strand was synthesized and inserted as a single-strand DNA via bridge formation between the sticky ends of PstI and HindIII.

Figure 13A:
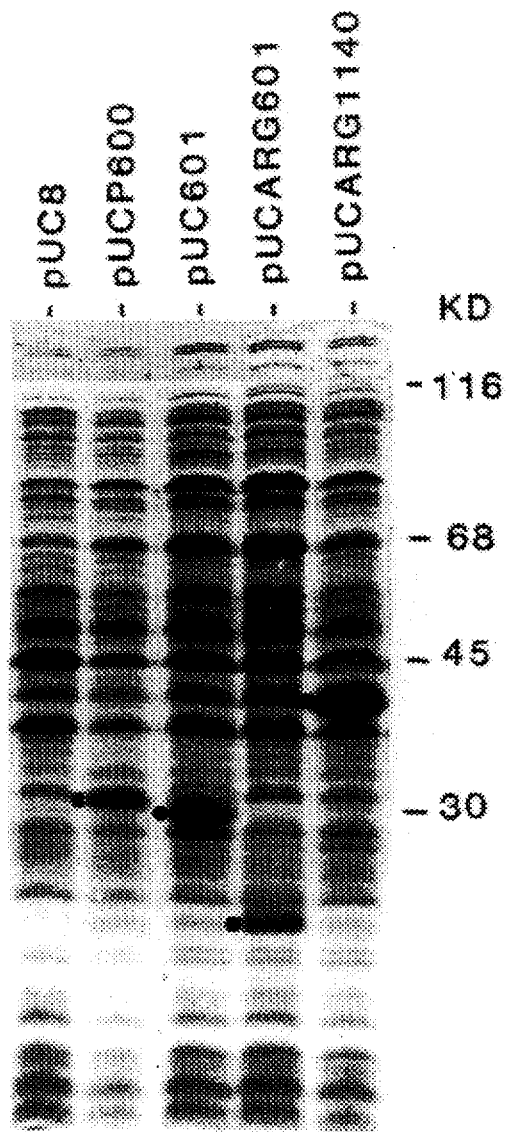
Figure 13B:
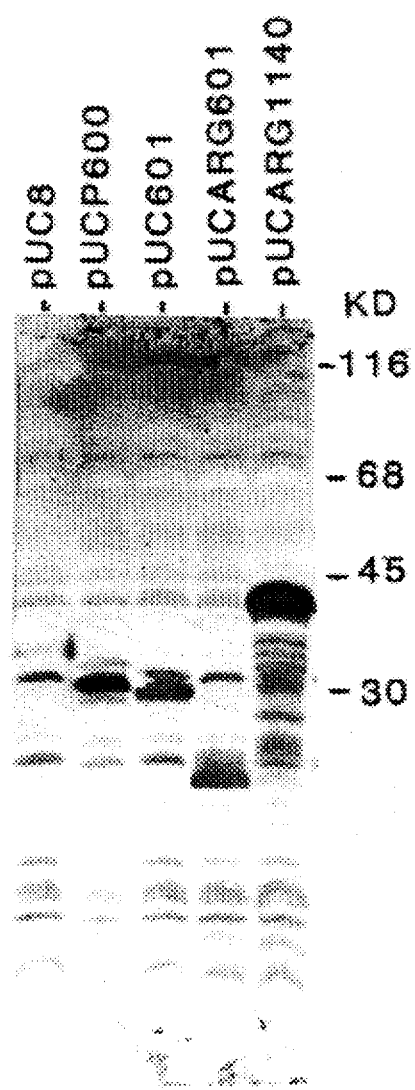

FIGS. 13A and 13B: IPTG-induced expression of the plasmids pUC600, pUC601, pUCARG601 and pUCARG1140 with pUC8 as a control FIG. 13A shows a Coomassie-stained SDS-PAGE. The newly detected proteins are marked by a black dot.

FIG. 13B shows the corresponding western blot obtained after immunostaining with serum from NPC patients. In comparison to pUCP600 the EBV-related protein encoded by pUC601 is about 1.5 kD smaller due to the lack of 14 aminoacids (6 amino-acids encoded by the pUC-polylinker and 8 from the PstI-SstI fragment). The size of the protein encoded by pUCARG601 is further reduced for about 11 kD since the read through into the lacZ region of pUC is inhibited by stop codons present in the inserted oligonucleotide. In pUCARG1140 the size increases to about 42 kD due to the insertion of the 540 bp fragment. The protein is stable in bacterial cells.

Figures 14A, 14B:
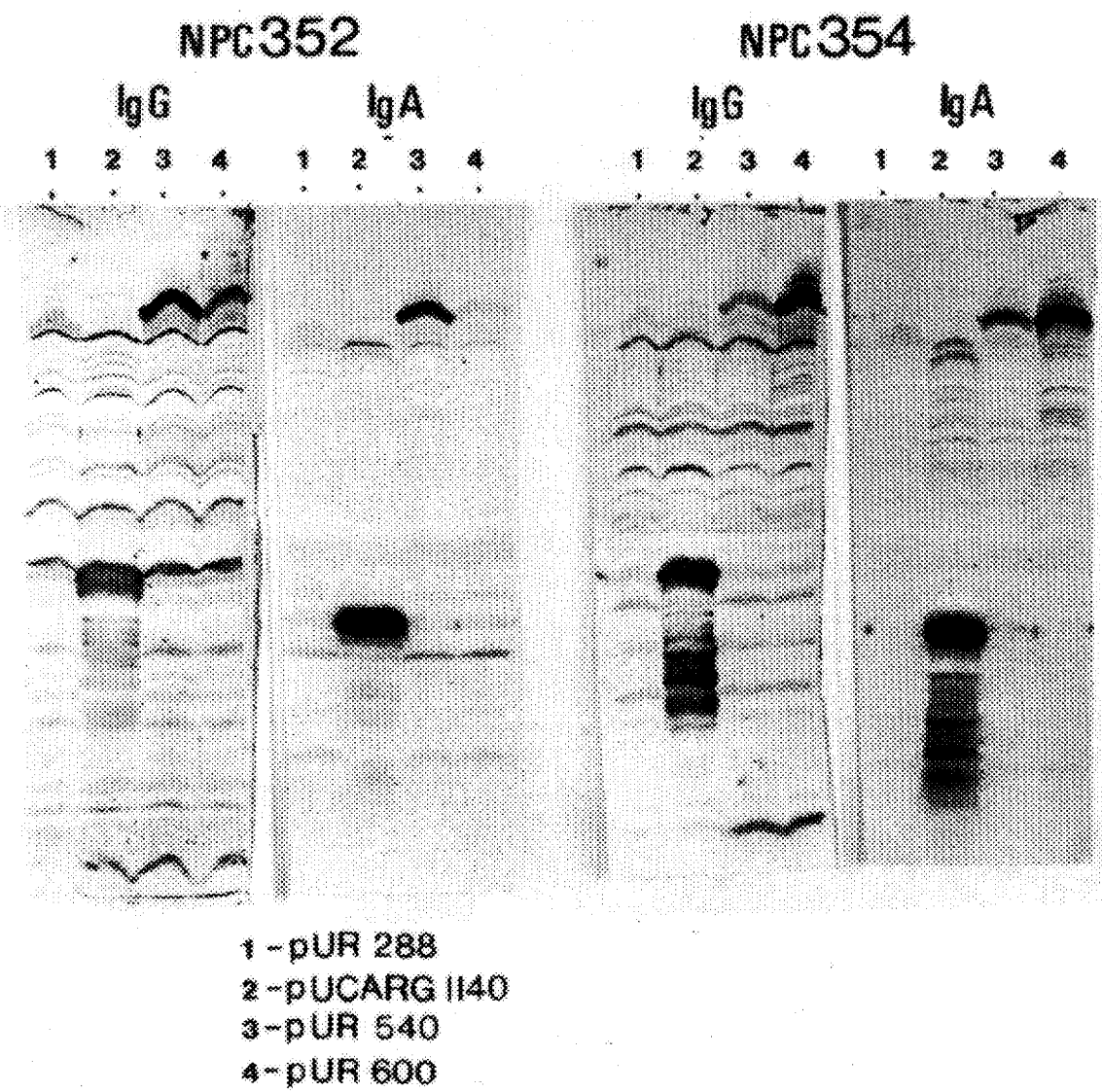

FIGS. 14A and 14B: Distribution and reactivity of the IgG and IgA antibodies of individual NPC-sera against the two epitopes detected in p138. Lysates of IPTG-induced *E.coli* cells carrying the indicated plasmids were independently separated on a 12% SDS-PAGE four-times and the proteins were transferred to Nitrocellulose by Western-blotting. Lanes 1:pUR288 as negative control; lanes 2:pUCARG1140 as a positive control; lanes 3: pUR540; lanes 4: pUR600. Two individual NPC-sera, no. 352 (FIG. 14A) and 354 (FIG. 14B), were incubated with the filters and the bound IgG and IgA antibodies were visualized using peroxidase conjugated anti-human IgG and anti-human IgA rabbit antibodies. The different locations of the proteins in the Western blots, especially of pUCARG1140, result from different electrophoresis times of the SDS-PAGEs.

Whereas in NPC-serum no.352 (FIG. 14A) the main reaction of the IgG and IgA antibodies is directed against the P540 epitope from the C-terminus of p138 (see FIGS. 9A, B and C) in serum no.354 (FIG. 4B) the main part of the anti-p138 antibodies recognizes the P600 epitope (see FIGS. 9A, B and C). This indicates that both antigenic sites are necessary for detecting anti-p138 antibodies in sera.

Figure 15:
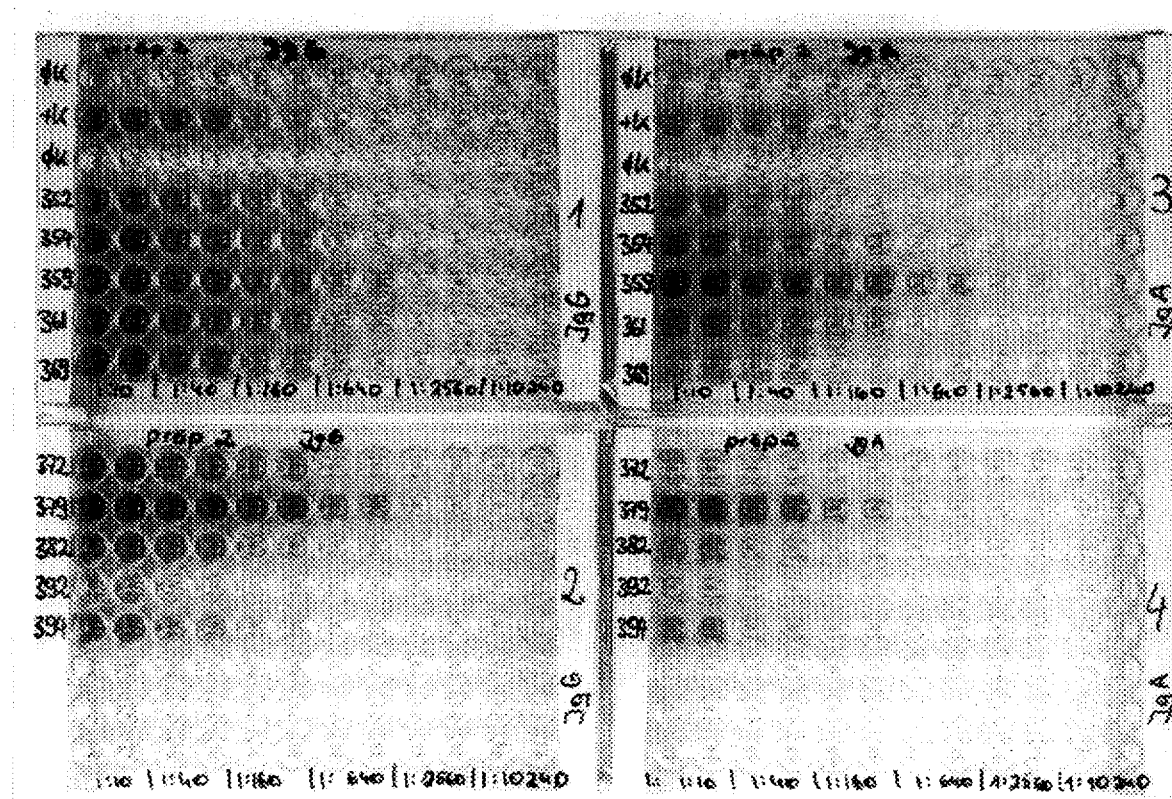

FIG. 15: ELISA test using the protein encoded by plasmid pUCARG1140 as antigen.

Rows 1 and 3: EBV-negative sera, row 2: NPC pool serum, row 4–13: individual NPC sera. The dilutions tested are indicated at the bottom; left lane: IgG right lane:IgA.

FIGS. 16A and 16B: Purification of proteins-carrying oligo-arginine groups at their carboxy-terminus.

FIG. 16A. Sequence of the oligonucleotide encoding five arginine residues and two stop codons. A HindIII-site at the 5'-end and a PstI-site at the 3'-end were generated for the insertion of the oligonucleotide into pUC8.

FIG. 16B. Purification scheme of insoluble expressed eukaryotic proteins carrying said Arg-linker at their carboxy-terminus.

FIGS. 17A–17B: DNA sequence of the leftward reading frank of the Bam L-fragment encoding gp 250/350.

The coding region for the glycoprotein starts at genomic position 92153 and ends at position 89433. The sequence shown is the respective negative strand, beginning with the BamHI site at position 92703. According to the sequence numbering in this figure the gp 350 encoding region is located between position 556 and 3276. A TATAA-box in the region of basepair 520 is marked with . . . , the probable poly-adenylation site at position 3290 with +++. The splice donor and splice acceptor sites are indicated by) (—— for donor and ——) (for the acceptor site. A hydrophobic region near the carboxy-terminus of the coding region is marked with * * * . Probably this aminoacid sequence serves as an anchor sequence for fixing the protein to the membrane.

Figure 18A:
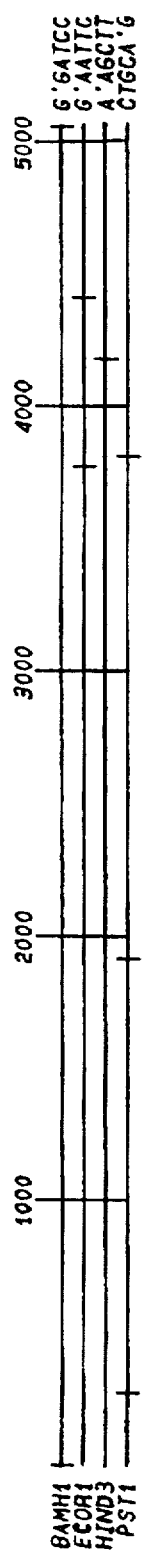
Figure 18B:
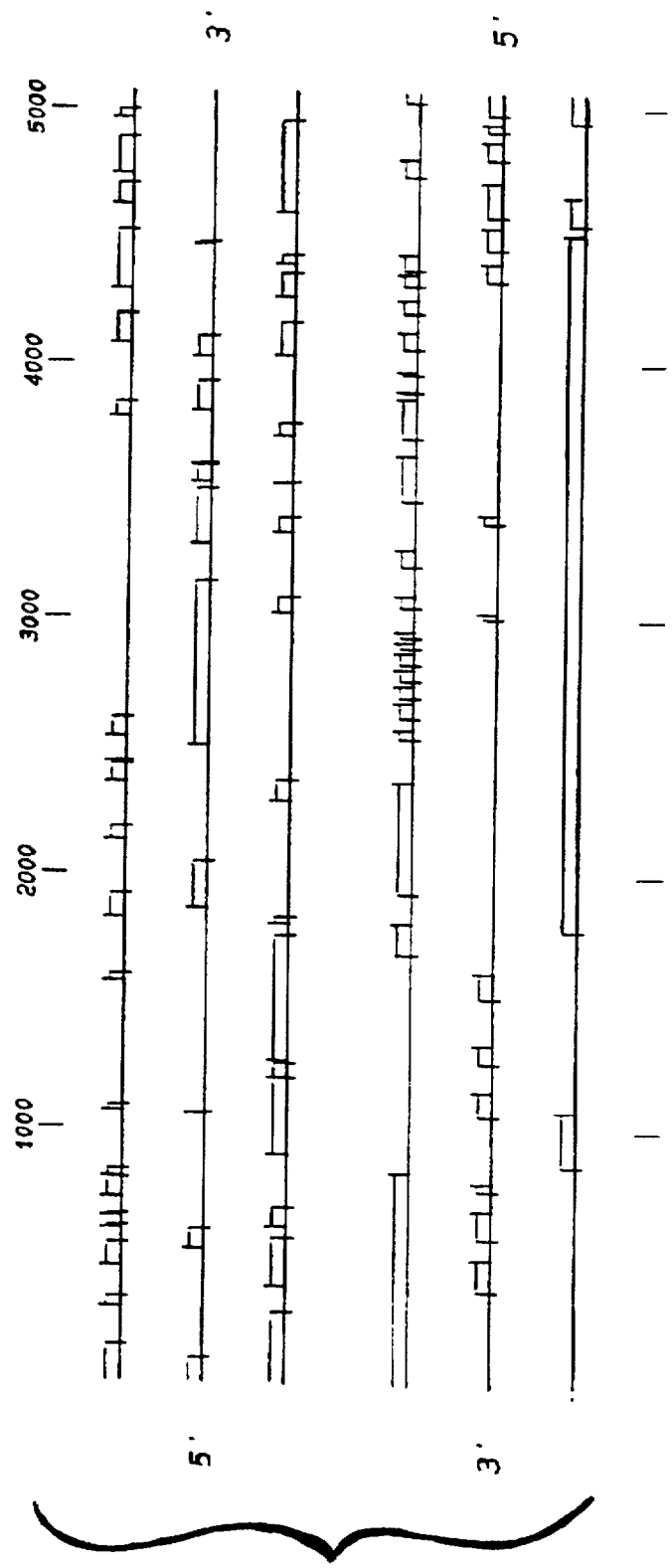

FIGS. 18A and 18B: Restriction map and open reading frames of the Bam L-fragment FIG. 18A. Restriction map: The positions of the restriction enzymes Bam HI, EcoRI, HindIII and PstI are indicated relative to the nucleotide positions of the Bam L-fragment.

FIG. 18B. Open reading frames: The open reading frames of the Bam L-fragment are indicated as boxes and given for both polarities of the respective DNA sequence.

Figure 19:
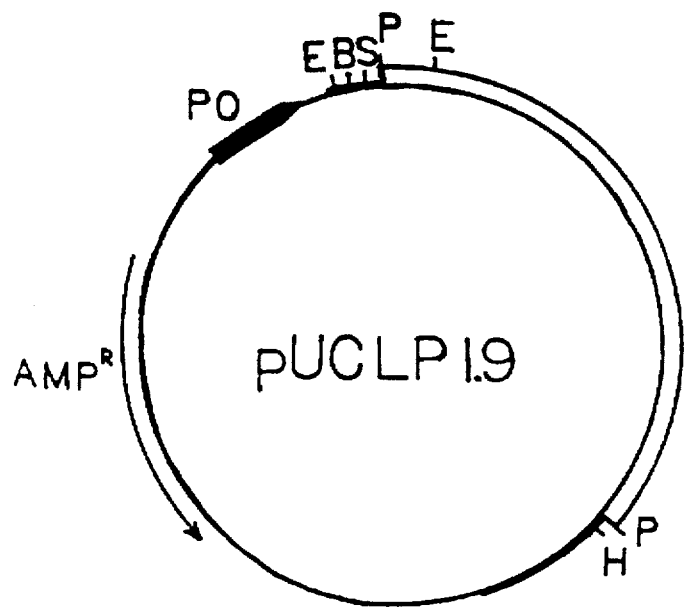

FIG. 19: Restriction map of the plasmid pUCLP1.9

The size of pUC8 is 2.7 kb. The cloning region 3' of the LacUV5 β-galactosidase promoter and operator (PO) contains an EcoRI (E), BamHI (B), SalI (S), PstI (P), and HindIII (H) site. The 1.9 kb subfragment of the Bam L-fragment, indicated by an open bar, was inserted into the PstI site. The reading frame has the same orientation as the lacZ-coding part of pUC8 (indicated by a heavy black line).

Figure 20:
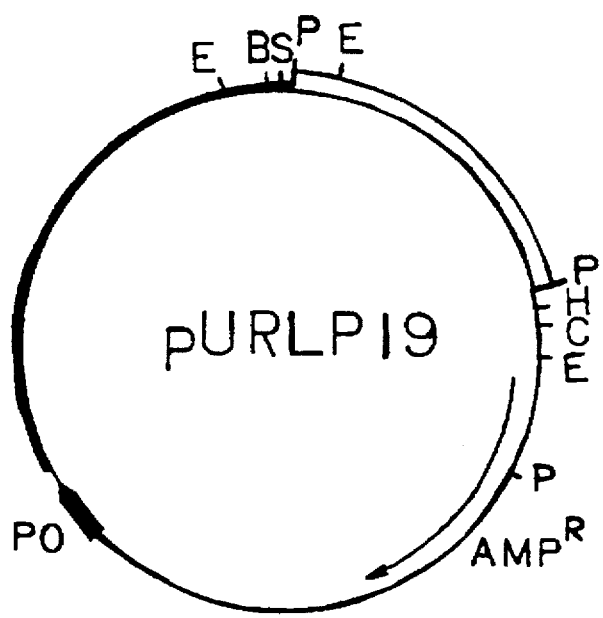

FIG. 20: Restriction map of plasmid pURLP1.9

The vector pUR290 has a length of 5.2 kb and consists of the β-lactamase gene (AMP$^R$) and the origin of replication of pBR322. The β-galactosidase gene is indicated by a heavy black line, the respective promoter-operator region by PO. The restriction enzymes are abbreviated as follows: BamHI(B), ClaI(C), EcoRI(E), HindIII(H), PstI(P), and SalI(S).

The 1.9 kb insert of pUCLP1.9 was introduced between the BamHI and the HindIII site.

FIGS. 21A–21F: DNA- and amino acid sequence of the fusion protein encoded by plasmid pURLP1.9 bp 4–3069: β-galactosidase bp 3070–3072: pUR290 linker (given in low letters)

bp 3073–3088: pUC8 multiple cloning site (BamHI to PstI; given in low letters)

bp 3089–4985: PstI fragment of gp 350 bp 4986–4994: pUC8 multiple cloning site (PstI to HindIII; given in low letters)

bp 4995–END: pBR322 sequence.

Figure 22:
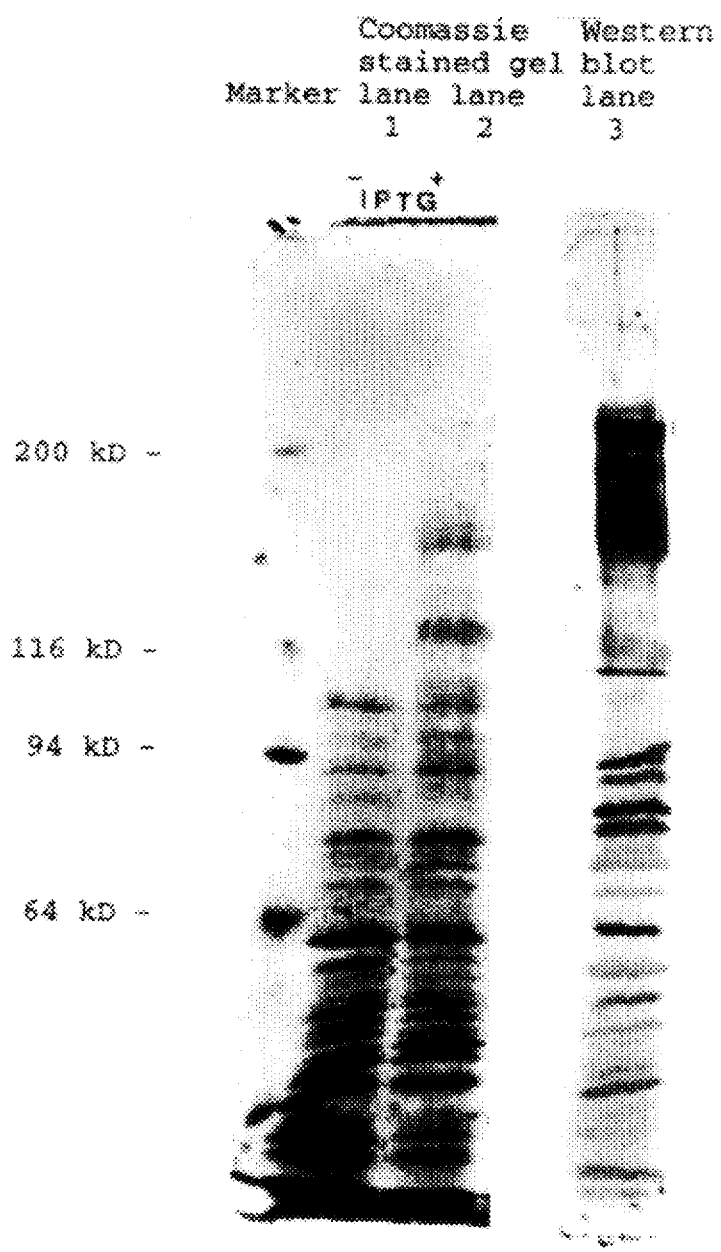

FIG. 22: Expression of the B-gal:gp 350 protein encoded by plasmid pURLP1.9

Lanes 1 and 2 show a coomassie blue stained PAGE of an uninduced (lane 1) and an IPTG induced (lane 2) pURLP1.9 containing clone.

Since there are a lot of bands with different molecular weights, it seems that the main part of the protein is incompletely synthesized.

Lane 3 shows a peroxidase-DAB stained Western blot with NPC sera. It is demonstrated that all newly expressed proteins are antigenic, except that band according to the size of 116 kD which corresponds to the β-galactosidase.

The bacterial background bands are due to the high content of antibacterial-antibodies in the serum used.

Figure 23A:
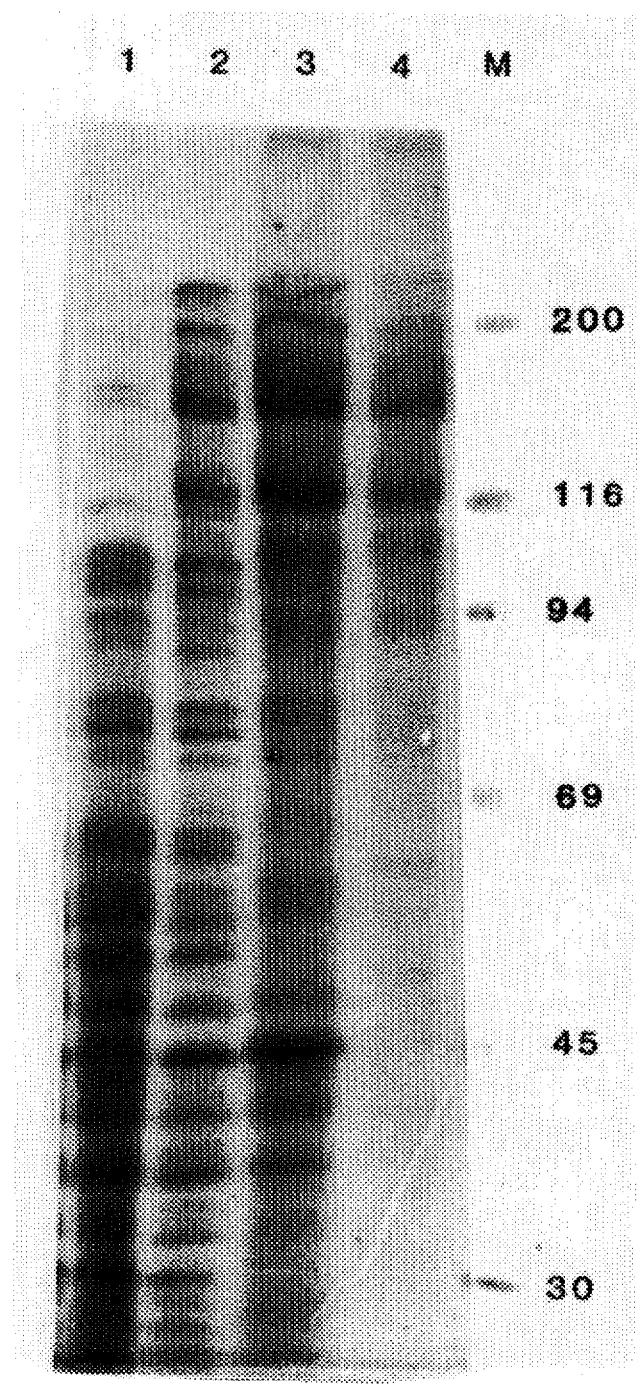
Figure 23B:
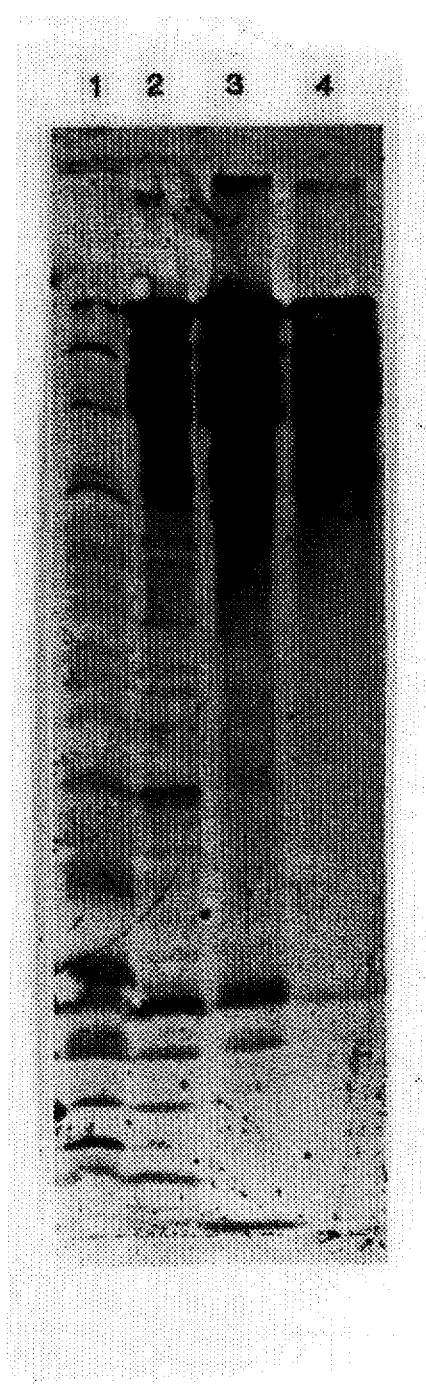

FIGS. 23A and 23B: Purification of the β-gal:gp 350 fusion protein encoded by plasmid pURLP1.9

FIG. 23A. Coomassie stained gel; FIG. 23B. Western blot, treated with NPC serum

Lane 1: Uninduced culture

Lane 2: IPTG induced culture

Lane 3: Insoluble proteins of the lysed bacteria, disolved in 8M urea

Lane 4: β-gal:gp 350 protein containing fractions, pooled after SEPHAROSE 2B-C1 chromatography.

Figure 24:
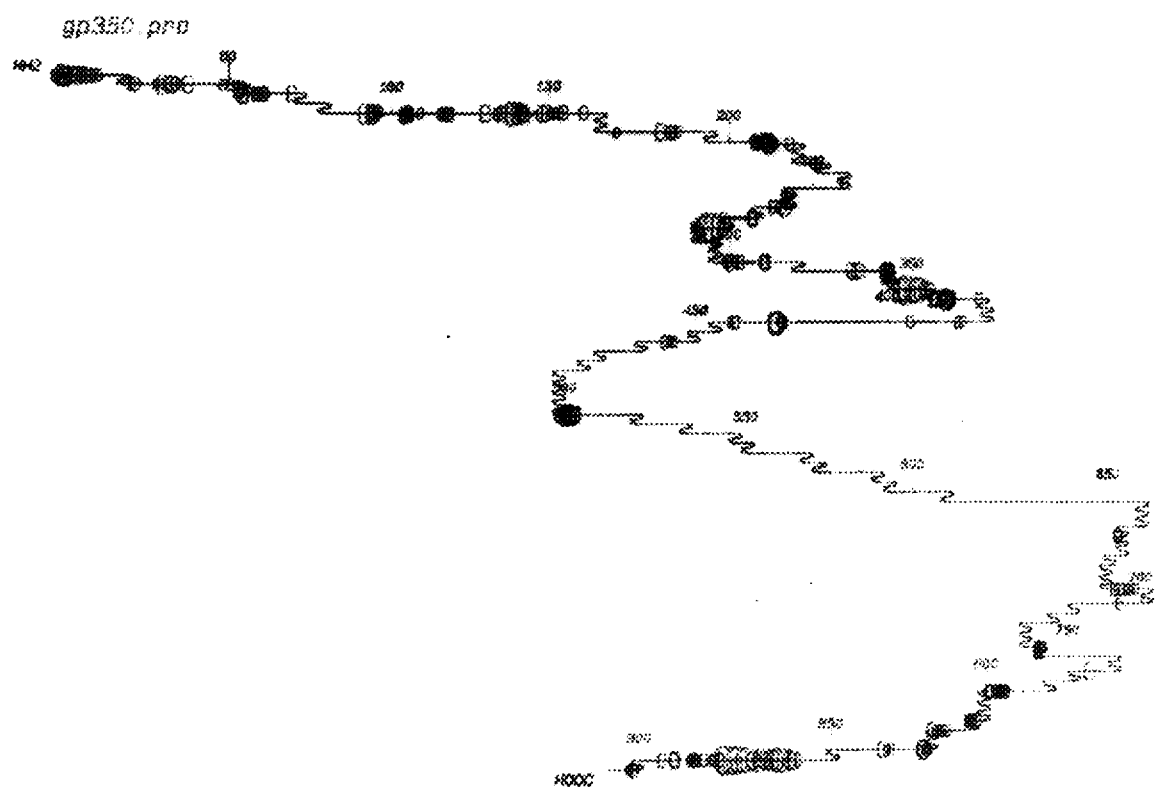

FIG. 24: Computer-predicted secondary structure of gp350 comprising the relative values of hydrophilicity (dark circles) and hydrophobicity (grey circles). In the scale given only the loop structures can be seen clearly as line turns of 180°.

Figure 25A:
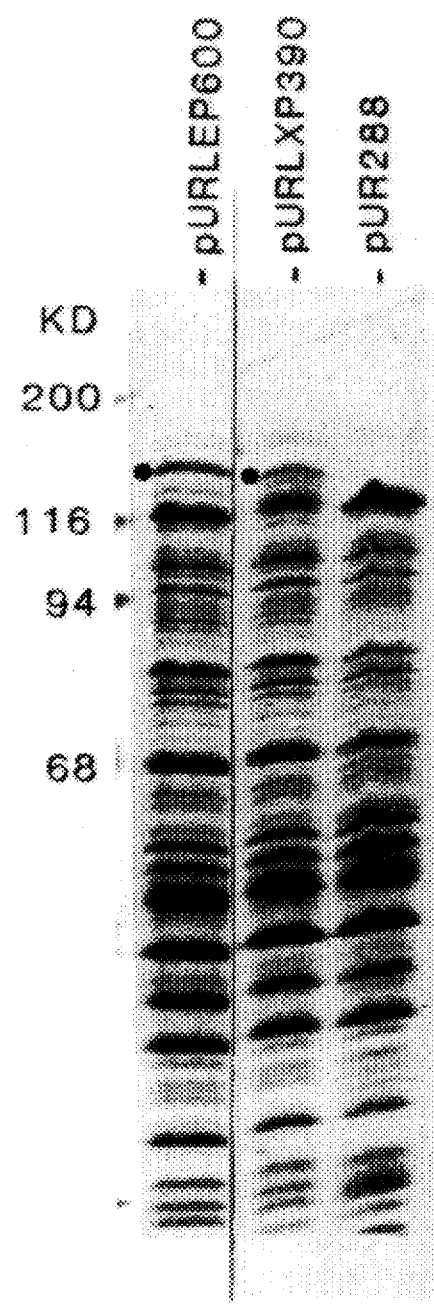
Figure 25B:
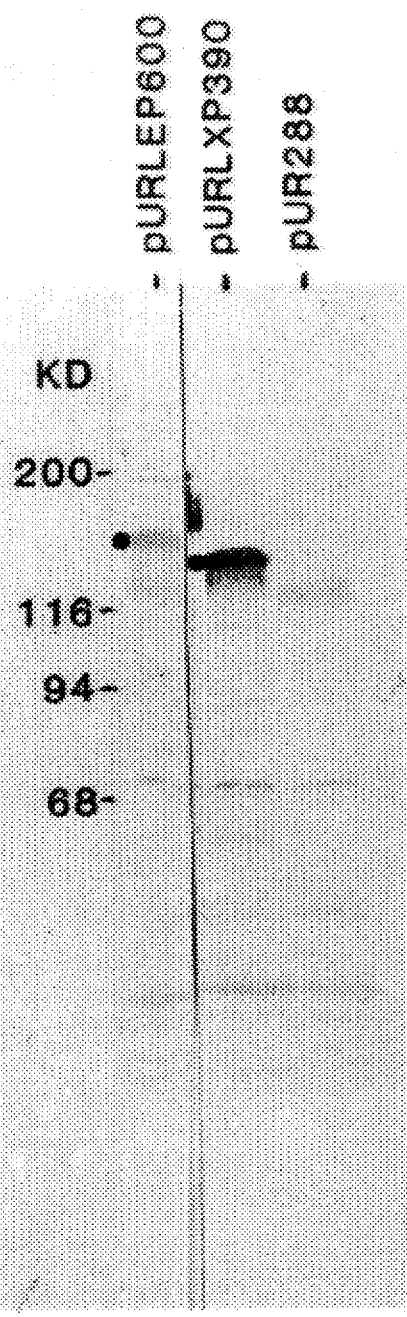

FIGS. 25A and 25B: Expression of gp350-fragments as β-gal fusion proteins.

The coomassie blue stained expression products encoded by plasmids pURLEP600 and pURLXP390 are shown in FIG. 25A (pUR288 as control). In FIG. 25B the same probes are shown after immunostaining for demonstrating their reactivity with EBV-positive sera.

Figure 26:
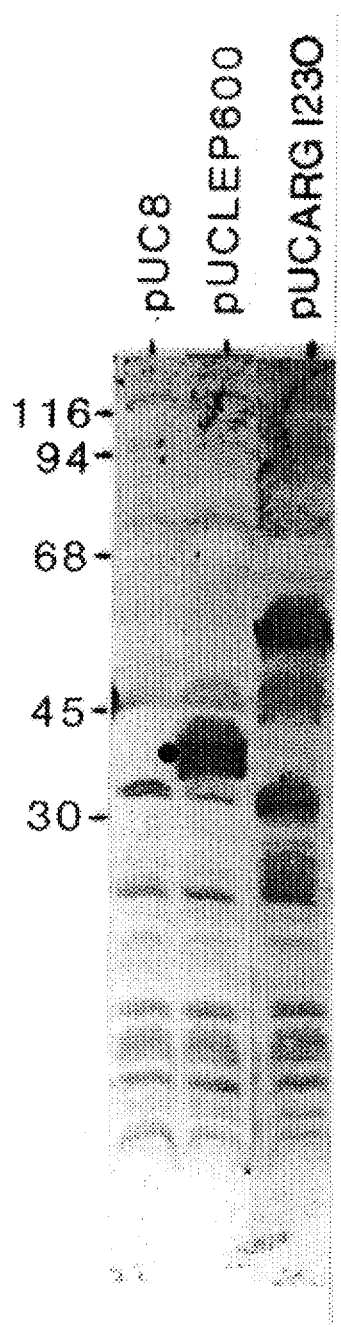

FIG. 26: Expression of the proteins encoded by pUCLEP600 and pUCARG1230 and their reactivity against EBV-positive sera with pUC8 as control; upper part: comassie-stained SDS-PAGE, lower part immunostained westernblot.

Figure 27:
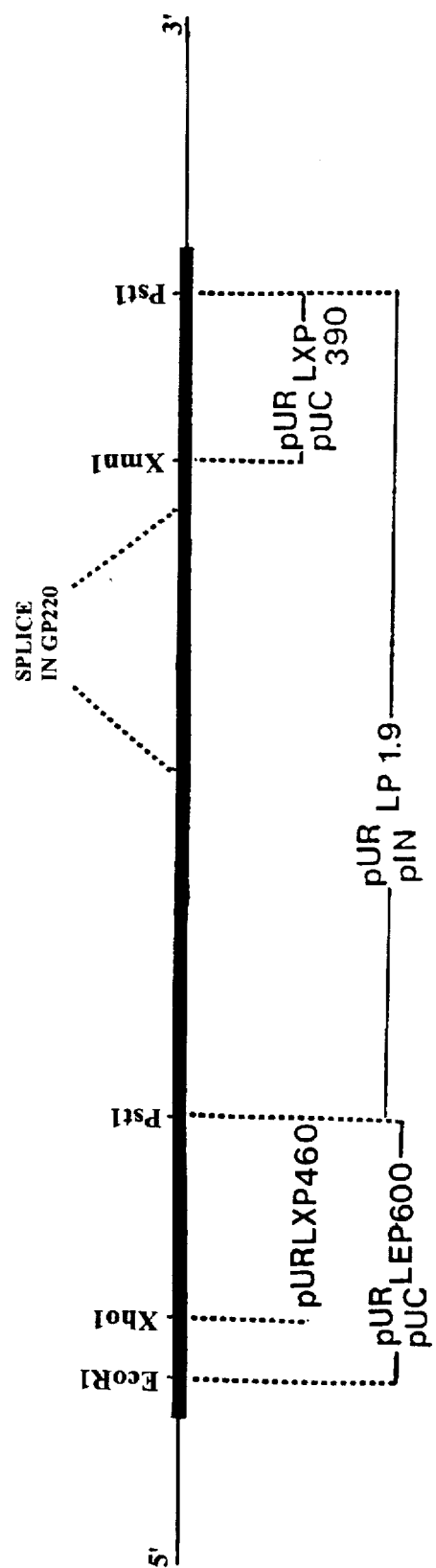

FIG. 27: Restriction map of the region coding for gp 250/350

The dark bar indicates the region coding for gp 250/350. Furthermore the restriction enzymes used for subcloning, the splice sites, and the inserts of the recombinant expression plasmids constructed according to examples 13 and 15–17 are shown.

FIGS. 28A–28D. DNA sequence and corresponding aminoacid sequence of EBV-related proteins.

FIG. 28A to FIG. 28A-3. Protein p54 Nucleotide sequence and derived aminoacid sequence of protein p54 which is identified in in vitro translation as p47 but correlated with immuno-precipitation with monoclonal antibodies FIG. 28B-1 to FIG. 28B-6. Protein p90

Figure 1:
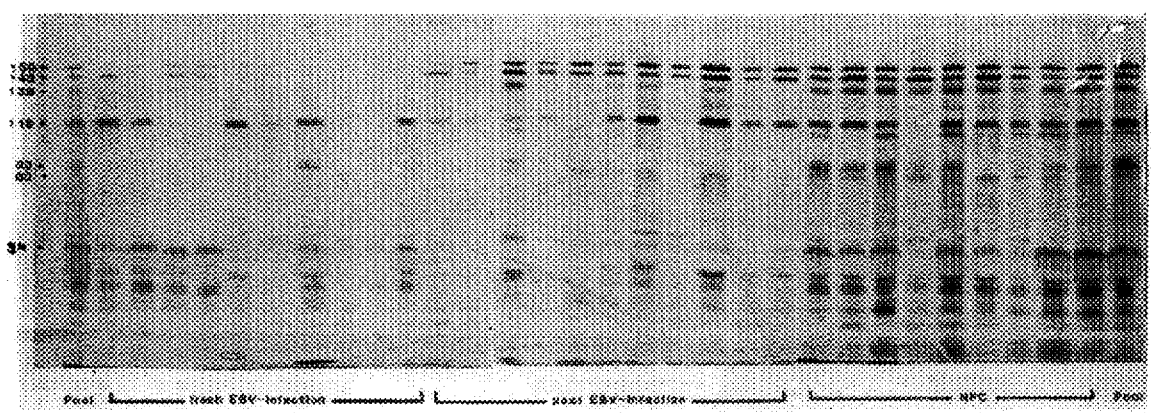
FIG. 1: Autoradiography of an immunoprecipitation of EBV-specific sera derived from patients suffering from mononucleosis and NPC.

FIG. 28C-1 to FIG. 28C-10. Protein p143

FIG. 28D-1 to FIG. 28D-10. Protein D150

Figure 29:
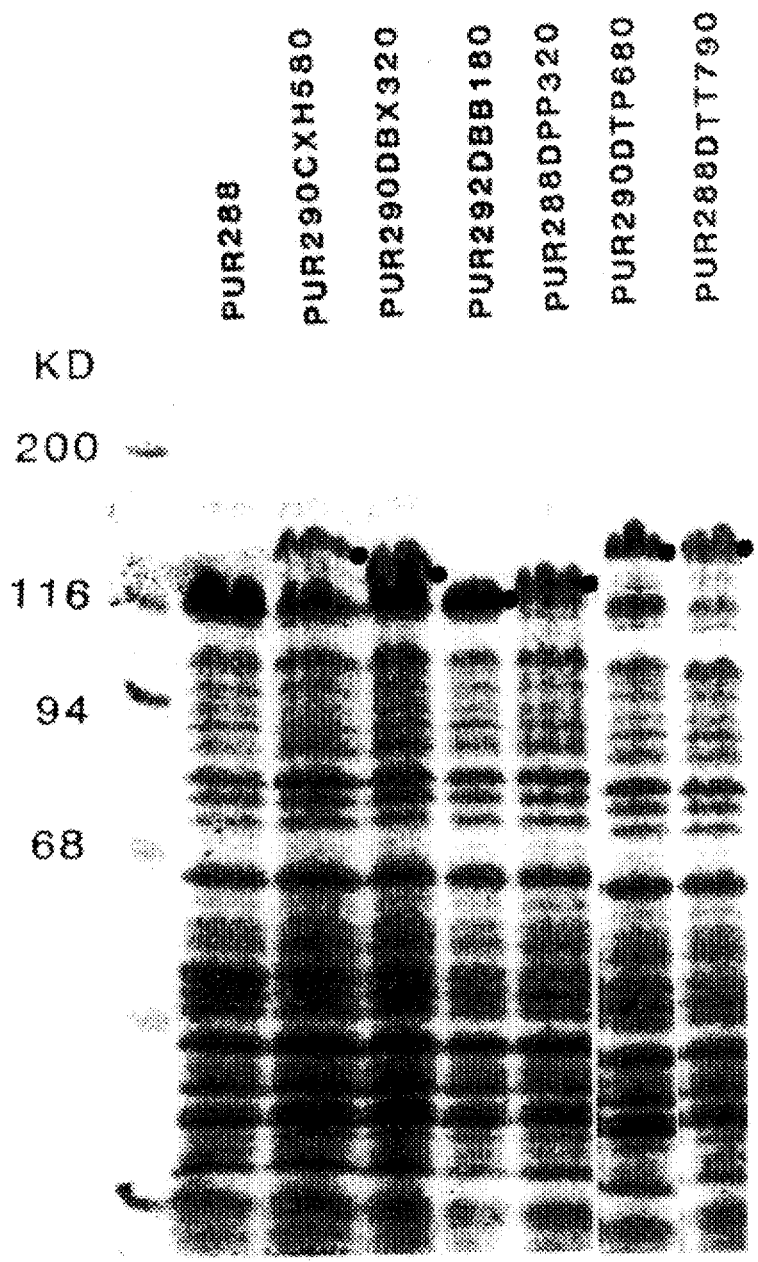

FIG. 29: Expression of the β-gal::p150 fusion proteins

IPTG-induced clones indicated on top were separated after lysis in an 10% SDS-PAGE and the proteins were stained with Coomassie-blue. As a control pUR288 was applied to show the size of the β-galactosidase. All clones produce new proteins larger than the control clone and corresponding to the insert size.

Figure 30:
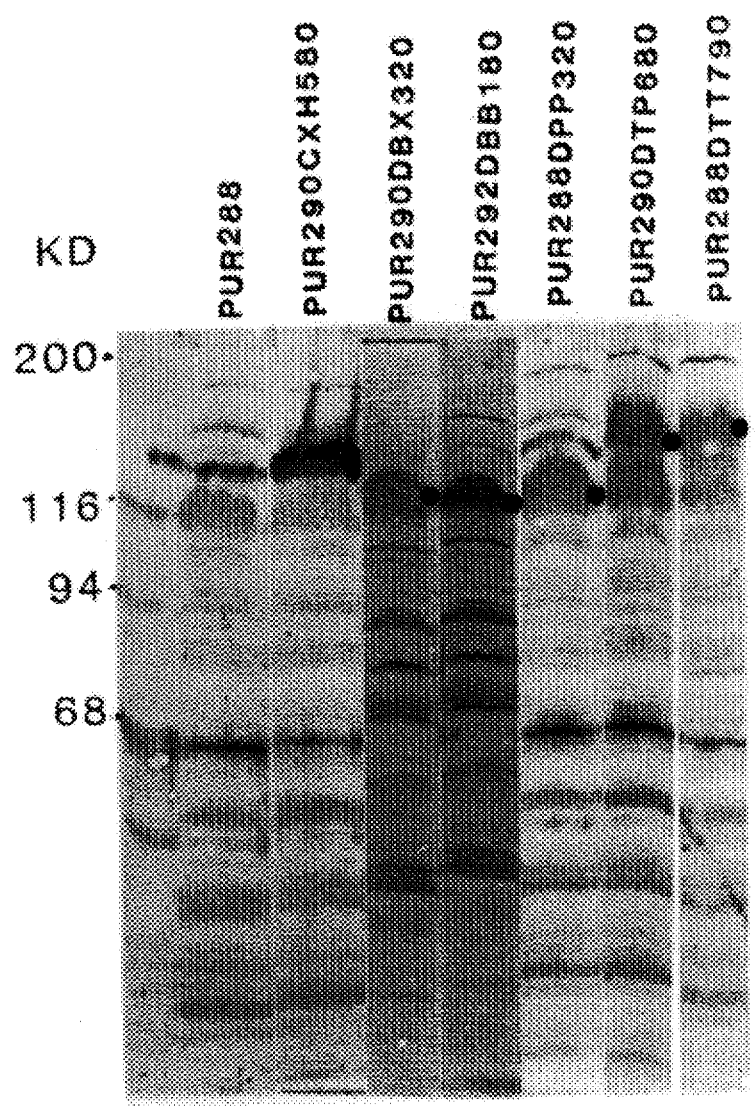

FIG. 30: Antigenicity of the β-gal::p150 fusion proteins

The same lysates from clones shown in FIG. 29 were transferred to nitrocellulose and EBV-related antigens were visualized by immuno staining (see supra). The clone encoding the N-terminal part reacts strongly.

Figure 31:
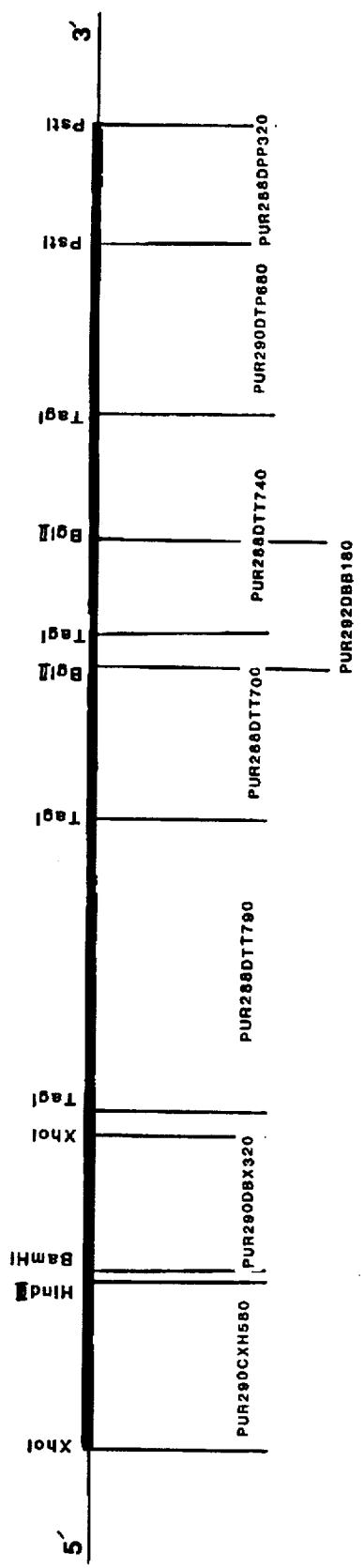

FIG. 31: Map of the p150 encoding region

The p150 encoding region is shown as dark bar. The restriction sites used for subcloning and the resulting pUR-clones are also indicated.

BEST MODE OF CARRYING OUT THE INVENTION

EXAMPLE 1

Identification of an Antigen Suitable for Diagnosis of NPC

In order to obtain the desired DNA sequences coding for EBV-related antigens of diagnostic significance the following strategy was developed: Immunoprecipitation of Epstein-Barr viral proteins with various sera from normal adults, patients with fresh infectious mononucleosis or nasopharyngeal carcinoma was used to identify antigens, which are of relevance for the diagnosis of immune status and characteristic for a particular disease (FIG. 1). These antigens have been localized on the Epstein-Barr virus genome by hybrid-selected translation. With the use of sequence data, these genes were subcloned from EBV-DNA and expressed in eucaryotic and procaryotic cells.

It was shown by immunoprecipitation that EA and VCA are not single antigens but families of antigens that consist of several polypeptides (G. J. Bayliss, H. Wolf, "The regulated expression of Epstein-Barr virus. III. Proteins specified by EBV during the lytic cycle", J. Gen. Virol 56, p. 105 (1981)) .

For the immunoprecipitation the EBV-producing, MA-positive cell line P3HR1, the EBV-positive, non-producing Raji cell line and the EBV-negative cell line BJAB were used. When the cells reached a density of about $10^6$/ml, they were diluted with an equal volume of fresh medium. For induction of EBV antigens, P3HR1 cultures were treated 4o ng/ml phorbol-12-mystrate-13-acetate (modified from zur Heusen et al. (H. zur Heusen, F. J. O'Neill, U. K. Freese, E. Hecker, "Persisting oncogenic heroes virus induced by the tumor promoter TPA", Nature 171, p. 373 (1978)) and 3 mM butyric acid immediately after subculture. For the labelling of the proteins, the cells were collected by low-speed centrifugation and resuspended at a density of $2 \times 10^6$ cells/ml in methionine-free MEM culture medium containing between 5o and 100 μCi/ml $^{35}$S-methionine. The cells were incubated at 37° C./5% $CO_2$ for 4 h and subsequently washed with cold Hanks' phosphate buffered saline (PBS) and resuspended in cold IP buffer (1% Triton-X-100, 0.1% SDS; 0.137M NaCl; 1 mM $CaCl_2$; 1 mM $MgCl_2$; 10% glycerol; 20 mM Tris-HCl pH 9.0; 0,01% $NAN_3$; 1 μg/ml phenylmethylsulphonyl fluoride) at a concentration of $5 \times 10^6$ cell/ml. Then the cells were disrupted by sonication and incubated on ice for 60 min. The extracts clarified by centrifugation at 100,000× g for 30 min at 4° C.

$^{35}$S-methionine labelled extracts were immuno-precipitated exactly as described (G. J. Bayliss, et al., supra). The results are shown in FIG. 1.

Antibodies to p138, p105, p90 and p80 are present in each of the NPC sera and only in some of the other EBV-infection specific sera. In analogy antibodies to p54 (identical to p58 in G. J. Bayliss et al., supra) are significant for fresh EBV-infection (infectious mononucleosis) as compared to convalescent state. Antibodies to p150, p143, p110 are also present in convalescent sera of healthy individuals and can serve as markers for immunity or, in connection with IgM specific tests for fresh EBV-infection or, in connection with IgA specific tests, for EBV-related neoplasia (NPC and BL).

The next step was to localize the antigens on the EBV genome. Therefore RNA was prepared by lysing the EBV-producing cells described above with 4M guanidine isothiocyanate and 0.5M 2-mercaptoethanol two days after induction (J. M. Chirgwin, A. E. Przybyla, R. J. MacDonald, W. J. Rutter, "Isolation of biologically active ribonucleic acid from sources enriched in ribonuclease", Biochemistry 18, p. 5294, (1979)). The lysate was centrifuged for one hour at 20,000 rpm (SW 41, Beckmann) and the supernatant layered on top of 2 ml CsCl density 1.8 g/cm$^3$. After centrifugation for 17 hours at 150,000 g, the RNA pellet was extracted with chloroform and precipitated with ethanol. 100 μg total cellular RNA was hybridized for 2.5 hours at 52° C. in 65% formamide and 0.4M NaCl to 16 μg cloned EBV-DNA, which was sonicated, denatured and spotted on small nitrocellulose filters. Bound mRNA was eluted by boiling the filters 90 sec in water. The RNA was translated in vitro with a mRNA dependent rabbit reticulocyte lysate. The translation products were immunoprecipitated using 5 μl of a pool of human NPC sera for one assay after preincubation with a protein extract from unlabelled EBV-negative BJA-B cells as previously described (G. J. Bayliss, G. Deby, H. Wolf, "An immunoprecipitation blocking assay for the analysis of EBV induced antigens", J. Virol. Methods 7, p. 229 (1983)). The immune complexes were bound on protein A-SEPHAROSE, washed, eluted by boiling the beads in electrophoresis sample buffer and loaded onto SDS-polyarcrylamid gets. This procedure allowed mapping of a number of viral proteins (FIG. 2) relative to the EBV B95-8 genome. The localization of p138, is given in FIG. 2. Using sequence data (R. Baer, A. T. Bankier, M. D. Biggin, P. L. Deininger, P. J. Fawell, T. J. Gibson, G. Hatfull, G. S. Hudson, S. C. Satchwell, C. Seguin, P. S. Tuffuel, B. Barrel, "DNA-sequence and expression of the B95-8 Epstein-Barr virus genome", Nature 31o, p. 2o7 (1984)), appropriate open reading frames for p138 and p54 were identified (FIG. 2). These open reading frames are completely contained in the right part of the BamA-fragment at the right end of the viral genome.

EXAMPLE 2

Cloning of the p138 Encoding Region

According to the sequence data of R. Baer et al., (supra), there is a large open reading frame contained in the BamA-fragment of EBV 595-8 which is suitable for encoding p138. The nucleotide sequence, the corresponding aminoacid sequence and the respective regulatory elements of the gene of p138 are given in FIGS. 3A-3I.

50 µg DNA of the plasmid pBR322-BamA (J. Skare et al., supra) were digested with 50 U XhoI (Boehringer) for 2 h at 37° C. in a total volume of 150 µl containing 150 mM NaCl, 1o mM MgCl$_2$, 6 mM mercaptoethanol, 6 mM Tris-HCl, pH 7.9. 30 µl stop buffer (10 mM Tris-HCl, 50 mM EDTA, 60% sucrose, 1% bromphenol-blue, pH 7.5) were added, the mixture was put onto a preparative 1% agarose gel in acetate-buffer (0.04M Tris-acetate, 2 mM EDTA, pH 7.6), and electrophoresed for 16 h with 4o V at 4° C. As a size marker HindIII digested λ-phage DNA (Boehringer) was used. After staining the gel in Tris-acetate buffer with ethidium bromide (0.5 µg/ml) for 1 h at room temperature (RT), the DNA was visualized by UV-illumination and the bands corresponding to 3.0 and 3.3 kb were excised (the 3.0 kb XhoI-generated fragment is the desired fragment, the 3.3 kb XhoI-generated fragment is a partial digest product (one XhoI restriction site was not cut)).

The DNA of the bands was eluted by putting the agarose pieces into dialysis bags, adding 3 volumes of Tris-acetate buffer and electrophoresed for 4 h (100 V, 4° C.). Further purification was carried out by a chromatography with Elutip D columns (Schleicher & Schuell) according to the procedure recommended by the manufacturer, extraction of the contained ethidium bromide with isoamylalcohol and precipitation of the DNA by adding 2.5 volumes ethanol and incubating overnight at −20° C. The DNA was collected by centrifugation in a Sorvall SS 34 rotor (17,000 rpm, 20 min) and washed with 70% ethanol. After lyophilization the DNA was dissolved in 15 µl TE buffer (10 mM Tris-HCl, 1 mM EDTA, pH 7.5).

The DNA concentration of the two isolated fragments was estimated by electrophoresing 1 µl each in parallel with 100 ng and 1 µg of pUC8 DNA.

SalI digested DNA of the vector pUC8 (deposited with the Deutsche Sammlung für Mikroorganismen (DSM), G öttingen, West Germany, under the accession number DSM 3420) (J. Messing, J. Vieira, of double-digest restriction fragments", Gene 19, p. 269 (1982)) was prepared as described before, except that for inhibition of religation of the vector during the following ligase reaction the DNA was treated with alkaline phosphatase (0.5 units (Boehringer), 30 min at 37° C.).

In the following, the two purified fragments were each inserted into the cleaved vector (SalI and XhoI produce the same cohesive ends, i.e. —TGCA—). For this purpose for each of the fragments a ligation reaction was carried out with 300 ng fragment DNA and 100 ng pUC8 DNA in a total volume of 20 µl ligase buffer (10 mM Tris, 10 mM MgCl$_2$, 6 mM mercaptoethanol, 0.6 mM ATP, pH 7.5) containing 1U T4-DNA ligase (Boehringer). After 20 h at 14° C., 80 µl TE buffer and 200 µl competent E.coli JM83 cells (ATCC35607) (J. Vieira, J. Messing, "The pUC plasmids, an M13mp7-derived system for insertion mutagenesis and sequencing with synthetic universal primers", Gene 19, p. 259 (1982)) were added. The transformation was done according to the calcium chloride procedure (M. Mandel, A. Higa, "Calcium dependent bacteriophage DNA infection", J. Mol. Biol. 53, p. 154 (1970)). Then the cells were mixed with 1.5 ml L-broth (5 g yeast extract, 1o g tryprone, 5 g NaCl) incubated 1.5 h at 37° C., and finally plated on L-broth agar-plates (1.5%) supplemented with 50 µg/ml Ampicillin (Sigma) and 40 µg/ml X-gel (Boehringer). During this incubation bacteria carrying religated pUC8 molecules yield blue colonies and those which carry recombinant plasmids yield white colonies.

For identification of clones that carry the desired recombinant plasmid, twelve white colonies were picked and grown overnight at 37° C. in L-broth. Aliquots of DNA-preparations according to H. C. Birnboim and J. Doly ("A rapid alkaline extraction procedure for screening recombinant plasmid DNA", Nucl. Acids Res. 7, p. 1513 (1979)) were digested by BamHI and HindIII and electrophoresed on an agarose gel as described before. Furthermore, for demonstrating the orientation of the integrated fragment, a digest was carried out with BamHI and BglII. Finally the 3.3 kb was checked by a XhoI digest.

Plasmid pUC635 carries the 3.0 kb XhoI-subfragment of the BamA-fragment (pBR322 BamA) in the proper orientation and the proper reading frame relative to the lac UV5 promoter and is used for the expression of nearly the whole p 138 (FIGS. 4A and 4B). The fusion protein encoded by pUC635 is composed of 11 amino acids of the β-galactosidase amino terminus, 1018 amino acids of p138, 60 amino acids of the carboxy terminal part of the β-galactosidase and another 25 amino acids of a pBR322 encoded region. Plasmid pUC6130 carries the 3.3 kb fragment in the opposite orientation (FIG. 4) Since the strain E.coli K12 JM83 is not a β-galactosidase repressor overproducer, the fusion protein is constitutively expressed. Therefore the plasmid pUC635 was introduced into the β-glactosidase repressor overproducer strain E.coli K12 BMH71-18 (DSM 3413) (U. Rüther, B. Müller-Hill, "Easy identification of cDNA clones", EMBO Journal 10, p. 1791 (1983)). Instead of strain E. coli K12 MBH71-18 strain E.coli K12 JM109 (DSM 3423) can also be used (without essential alteration of the experimental procedure).

Besides pUC635 three other plasmids were constructed:pUC924, pMF924 and pKK378 (FIGS. 6 to 8).

The insert of pKK378 starts at the same Xhoi-site and continues up to the third XhoI-site located 250 bp 3' of the stop codon. This fragment of 3.3 kb was generated by an incomplete digest and inserted behind the tac-promotor and the start codon of pKK240-11 (F. Amann et al., supra). The expression product contains only two bacterial amino acids and its size is smaller then the size of the expression product of pUC635 because the bacterial lacZ part is missing.

pUC924 contains the fragment from the Bgl II-site to the third Xho I site. pUC9 (DSM 3421) was used as vector. Since the size of the insert is smaller than in pUC635 and since the stop codon from p138 is used, the molecular weight of the expression product is expected to be smaller than in pUC635 and pKK378.

The plasmid pMF924 was constructed from pEA305 (E. Amann et al., supra) and the same BglII-XhoI fragment as in pUC924. pEA30 5has a tac-promotor followed by the N-terminal part of the C1 repressor, the resulting fusion protein is expected to be 17 kd larger than in pUC924.

These constructs were tested for the production of EBV-related antigens by inducing the tac- and lac-promotors with IPTG and separating the proteins on an SDS-PAGE. None or only weak new bands could be detected on Coomassie-blue stained gels in the regions with the expected sizes. But after a transfer of the proteins onto nitrocellulose and immunostaining with a high titered NPC-pool serum and a peroxidase conjugated second anti-IgG antibody new EBV-specific bands were clearly detectable in all constructs. (FIGS. 4A and 4B)

All expressed proteins display almost the expected size, but the yield varied over a wide range. The proteins encoded by pUC635 and pMF924, seem to be more stably expressable than the non-fusion proteins from pUC924 and pKK378. However, the amount of even the highest expressed protein from pUC635 is too low for a large-scale production since in the Coomassie-stained gel only a very weak band was visible which may be due to the large size of the eukaryotic protein.

EXAMPLE 3

Immunological Assay of the Proteins Encoded by pUC635 pUC924, pMF924 and pKK378

The host cells transformed with plasmids pUC635, pUC924, pMF924 and pUK378 were cultivated in L-broth supplemented with 50 µg/ml Ampicillin to a cell density of $D_{600}=0.8$.

Then, for the induction of the β-galactosidase the lactose analogon isopropyl-β-D-thiogalactopyranoside (IPTG; Sigma) was added (final concentration: 1 mM). After a further incubation of 1.5 h at 37° C., 1.5 ml of the culture were centrifuged. The bacteria were resuspended in 200 µl boiling mix (2% SDS, 5% mercaptoethanol, 3% sucrose, 50 mM Tris-HCl, pH 7.0) and heated for 10 min at 1oo° C. 20 µl of the resulting protein extract were separated on a 12.5% polyacrylamide gel and finally the proteins were visualized by coomassie-blue staining, but since the yield of the expression product is very low, an immunostaining was necessary. Therefore the electrophoretically separated proteins were transferred to a nitrocellulose filter, i.e. a "Western-blot" was prepared (J. Renart, J. Reiser, G. R. Shark "Transfer of proteins from gels to diazobenzyl-methyl-paper and detection with antisera", Proc. Natl. Acad. Sci. USA 76, p. 3116 (1979), S. Modrow, H. Wolf, "Characterization of herpesvirus saimiri and herpes virus ateless induced proteins", in: Latent Herpes Infections in Veterinary Medicine, Martinus Nijnoff Publ., p 100 (1984)).

The Western-blot was prepared with a current intensity of 0.8 A for 3 h in Western-blot buffer (72 g glycine, 15 g Tris, 1 l methanol, $H_2O$ dest. ad 5 l). Then the nitrocellulose was saturated with Cohen buffer for 3 h (o.1% Ficoll 400, 1% polyvinylpyrroiidone, 1.6% BSA, 0.1% NP4o, 0.05% gelatine, 0.17M $H_3BO_3$, 28 mM NaOH, 150 mM NaCl, 6 mM $NaN_3$, pH 8.2) and incubated overnight with 1:50 diluted high titered EBV specific serum from NPC-patients. The serum had been preabsorbed to a bacterial-protein extract (1 ml/$10^9$ E. coli cells) to reduce the bacterial protein generated background. Afterwards unbound IgG was removed by washing the nitrocellulose filter for 5 h in gelatine buffer (5o mM Tris-HCl, 5 mM EDTA, 15o mM NaCl, 0.25% gelatine, 0.5% Triton, 0.2% SDS, pH 7.5). For visualizing the blotted EBV-specific proteins rabbit anti-human-IgG-antibodies coupled to peroxidase and diluted 1:200 in TN buffer (154 mM NaCl, 10 mM Tris, pH 7.4) was added. After 2 h at RT, unbound rabbit antibodies were removed by washing with gelatine buffer as described above. Finally the peroxidase reaction was carried out in 100 ml 50 mM Tris-HCl, pH 7.5, by adding 50 mg diaminobenzidine (Sigma) and 40 µl $H_2O_2$ and incubating 10 min. at RT. The results of this experiment are shown in FIG. 5.

EXAMPLE 4

Purification of the β-gal:p138 Fusion Protein Encoded by the Plasmid pUC635

The clone E.coli K12 JM109 pUC 635 was grown at 37° C. in 500 ml L-broth supplemented with Ampicillin as described above until the $OD_{560}$ was 0.8 The fusion protein synthesis was induced by IPTG (1 mM) and the incubation was continued for another 2 h. Then the cells were collected by centrifugation for 1o min in a GSA rotor (Sorvall) at 5,000 rpm and they were resuspended in 50 ml 2o mM Tris-HCl, pH 7.5. For lysating the cells, EDTA (50 mM final concentration) and lysozyme (2 mg/ml final concentration) were added and this mixture was incubated for 30 min an 37° C. In the following, the cells were sonicated (Labsonic 1510, Braun) twice for 8 min, Triton X-100 was added to a final concentration of 3% and, after further incubation at 37° C. for 30 min, insoluble particles of the suspension were pelleted by centrifugation (SS 34 rotor (Sorvall), 20 min, 10,000 rpm). The resulting pellet was dissolved in 2o ml of an 8M urea, 1o mM Tris-HCl, 0.5% β-mercaptoethanol, pH 7.5, solution and recentrifuged as before.

Finally 80 mg of the proteins were subjected to a column chromatography (SEPHAROSE 2B-C1 (Pharmacia), length 80 cm, diameter 3 cm) with 8M urea, 10 mM Tris, 0.1% β-mercaptoethanol, pH 7.5, buffer. 30 µl of each of the collected 4 ml samples were analyzed in a 15% PAGE and the fusion protein-containing fractions were pooled.

EXAMPLE 5

Cloning of p138 Subregions Coding for Antigenic Determinants Identified by Computer Analysis In principle in diagnostic tests only the antigenic determinant subregions of the antigenic protein are needed. Therefore the p138 amino acid sequence was analyzed by a computer programm and the identified subregions of this gene were introduced in suitable vectors. The production of such small proteins has the advantage that these are less vulnerable to rapid changes of antigenicity with decreasing length of the product. Furthermore especially in conjunction with assays for class specific antibodies they will be of diagnostic value.

According to the method of P. Chou and G. Fasman ("Conformational parameters for aminoacids in α-helical β-sheet and random coil regions calculated from proteins", Biochemistry 13, p. 211 (1974)) the calculation of the appropriate secondary structure of a protein caused by its aminoacid sequence (primary structure) is possible. Superimposed on the suggested structure, the program determines the relative hydrophilicity and hydrophobicity. Both data sets are combined and a computer graphic is drawn that shows α-helical, β-sheet, β-turning and randomly coiled regions of the secondary structure. Thereby the hydrophilic and hydrophobic regions are shown as open and closed circles, respectively.

An example of such computer graphic is shown for the p138 amino acid sequence in FIGS. 9A, B and C.

Based on the assumption that antigenic sites are mainly located in hydrophilic β-turns which are located on the surface of the protein, the region between about amino acid 520 and the carboxy-terminus of p138 should be antigenic. The corresponding DNA sequence is represented by a PstI-fragment of pUC635.

Thus pUC635 was cleaved with PstI and all PstI-fragments were isolated and introduced into PstI-cleaved pUC8, the remaining vector fragment with additional 400 bp (up to the first PstI-site of the p138 coding sequence) was religated (all methods as described in example 2).

The resulting recombinant plasmids were designated pUC P400, pUC P380, pUC P600, pUC P210, pUC P750, and pUC P540, respectively.

The aminoterminal region of the p138 encoding sequence was cloned by digesting the plasmid pBR322-BamA with PstI and HgiAI and inserting said fragment into PstI cleaved pUC9. (J. Messing et al., supra) (methods as described in example 2). The resulting recombinant plasmid is designated pUC HP.

With the exception of pUC HP in which translation stops at the 3' end of the insertion, in all subclones orientation and reading frames relative to pUC8 are correct.

Finally the recombinant plasmids were introduced into *E. coli* K12 JM 109 cells.

EXAMPLE 6

Expression of Antigenic Determinants Identified by Computer Analysis Using pUR288 D138 Subclones Since pUC subclones (example 5) sometimes are not stably expressible in bacteria, because they cannot build up a suitable tertiary structure due to their shortness and therefore can be degraded by proteases to a larger extent than complete proteins we constructed recombinant plasmids encoding large fusion proteins using at least a part of the β-galactosidase encoded by pUR288 (DSM 3415) (U. R üther et al., supra) by cleaving said PstI-fragment subclones with BamHI and HindIII, isolating the respective fragments and ligating them into BamHI and HindIII cleaved pUR288 (all methods as described in example 2).

The expression was carried out in *E.coli* K12 JM109. The products were analyzed as described in example 3. After coomassie-blue staining of the gel several large fusion proteins of different size were detected, however, after preparation of a Western-blot, only the products expressed by pUR600 and pUR540 showed specific reaction with the IgG antibodies mentioned (FIGS. 10A and 10B).

These results are in good agreement with the computer analysis.

Additionally the expression of the clones obtained according to example 5 was carried out according to example 3. The products, too, were analyzed as described in example 3. From the coomassie-blue stained gel it can betaken that only plasmids pUCP600and pUCP380 code for a stable fusion protein. The Western-blot shows that only pUCP600 derived fusion protein is antigenic (FIG. 11). This fusion protein contains 11 amino acids encoded by the aminoterminal cloning site, a region encoded by about 600 bp of p138 and carboxyterminal amino acids of the lacZ gene. Thus, the recombinant expression plasmids pUR600 and pUR540 as well as pUCP600 can be used for the production of large and small fusion proteins, respectively, containing anantigenic determinant of EBV-protein p138.

EXAMPLE 7

Figure 9C:
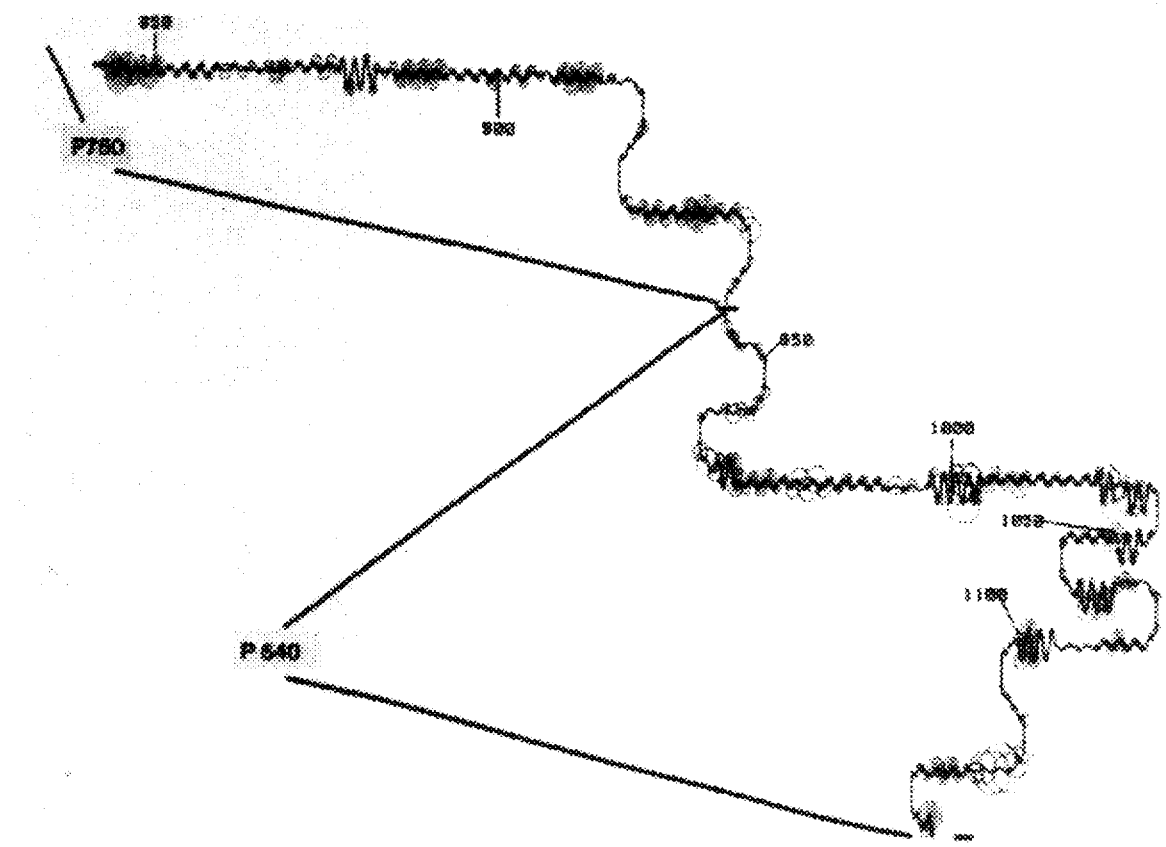

Application of the Protein Encoded by Plasmid pUCP600 for the Stabilization of per se Unstable Parts of Eukaryotic Proteins By means of the experiments of example 6 it was shown that the p138-derived protein parts (regions) are unstable with the exception of the protein encoded by plasmid pUCP600. The second antigenic region from the C-terminus of p138 (P540, see FIG. 9C) is not stably expressible using the recombinant pUC-vector pUCP540. The ability of the P600-region of p138 to stabilize such a per se unstable expression product is shown in this example.

For this purpose it was necessary to remove the 5'-PstI-site of pUCP600 by digesting the plasmid with SstI and HindIII (the SstI site is located about 20 bp 3' from the first PstI site). The p138-related SstI-HindIII fragment was inserted into SstI/HindIII cleaved pUC12 (DSM3422) J. Messing. "New M13 vectors for cloning", in Methods of Enzymology Vol. 101, Part C., R. Wu, L. Grossmann and K. Moldoave (eds.), Acad. Press, New York, 1983, 20–78).

Then the resulting recombinant plasmid was digested with EcoRI and PstI. The obtained 600 bp fragment was inserted into plasmid pUC8. The 5'-PstI site was now replaced by an SstI site and thus the reading frame is reconstituted at the 3'- and the 5'-end of the insert (FIGS. 12A). The resulting recombinant plasmid pUC601 still expresses a stable product (FIGS. 13A and 13B).

Between the PstI and HindIII site at the 3'-terminus of the EBV-encoded sequence a synthetic oligonucleotide obtained according to known methods coding in frame for 5 arginine and 2 stop codons was inserted as shown in FIG. 12B). The resulting plasmid pUCARG601 encodes the P600 region of p138 fused at its C-terminus to 5 arginine residues.

In a last step the PstI fragment encoding the P540 region of p138 was ligated to the PstI fragment encoding the P600 region of p138 after digestion with PstI. The resulting recombinant plasmid pUCARG1140 encodes a stable protein of about 43 kd which contains two antigenic sites of p138 fused in frame. In this fusion protein the protein region p600 stabilizes the protein region p540 (FIGS. 13A and 13B). The arginine residues at the carboxyterminus of the expression product may be used for the purification of the resulting fusion protein as described by Sassenfeld and Brewer (supra) (FIGS. 16A –B).

EXAMPLE 8

Construction of the Recombinant Plasmid pUCARG680

From the plasmid pUCARG1140 a modified version was constructed which lacks 435 bp of the p138 encoding region, the C-terminal part of the p600 fragment and the N-terminal part of the p540 fragment. The main antigenic sites predicted by the computer program are still present. The plasmid was designated as pUCARG680 and its construction was achieved by digesting pUCARG1140 with NcoI (cleavage site coresponds to bp1841 and bp3243 in FIGS. 3A–3I). Since the reading frames in the p600 NcoI site and the p540 NcoI site do not fit, the sticky ends were removed with S1-Nuclease.

30 μg of pUCARG1140 were digested with NcoI, the 3.3 kb vector-p138 fragment was separated by gelelecrophoresis and purified. 5 μg of this DNA fragment were digested with 100 units S1-Nuclease for 15 min at roomtemperature in 100 μl containing 33 mM Na-acetate, 50 mM NaCl, 0.03 mM ZnSO$_4$, pH 4.5. The digest was stopped by phenol extraction. After precipitation with ethanol the DNA was religated with T4-DNA ligase and used to transform competent *E.coli* K12 JM109 cells. The resulting clones were screended for the appearance of a new protein with 30 kb in size (pUCARG680). The shortened p600/p540 fusion protein encoded by pUCARG680 still reacts as an antigen.

The newly constructed recombinant plasmid pUCARG680 was deposited with the DSM under the deposition number DSM3408.

EXAMPLE 9

Assay of the Antigenicity of the Fusion Protein Encoded by Plasmid pUCARG1140

Immunoblots with the fusion proteins encoded by the recombinant plasmids pUCARG1140, pUR540, and pUR600 (examples 6 and 7) using individual NPC-sera reveal that the immunological reactions differ in various patients (FIGS. 14A and 14B). In this context it has to be understood that said plasmids encode fusion proteins containing the p138 regions p540+p600, p540, and p600, respectively (see FIGS. 9A, B and C).

Whereas in NPC serum no.352 the main fraction of the IgG and IgA antibodies is directed to the p540 region, the main fraction in NPC serum no.354 is directed to the p600 region of p138. A representative pool prepared from many sera from NPC patients did not detect additional antigenic sites. The conclusion from this finding is that the antigenic determinants p540 and p600 as encoded by the recombinant plasmids of the present invention are necessary and sufficient to achieve the desired specificity for ELISA tests useful for diagnostic purposes.

EXAMPLE 10

Application of Plasmid pUCARG1140 Encoded Fusion Protein for the Detection of NPC in ELISA Tests The purified fusion protein encoded by pUCARG1140 was coated on micro-titer plates. Ten individual NPC-sera were tested for their IgG and especially for their IgA reactivity. The IgA-anti-EA titer of these sera was previously determined in conventional immunofluorescence tests. The highest titer found was 1:80. In the ELISA test shown in FIG. 15, two EBV-negative, one NPC-serum pool and ten individual NPC-sera were tested up to a dilution 1:10640. The test was performed according to the usual ELISA protocol. Bound antibodies were detected with peroxidase conjugated mouse anti human IgG, i.e. IgA and peroxidase reaction. All NPC sera show a reaction with the coated antigen (up to 1:2560 in IgA) and no background reaction could be observed in the negative controls. This result indicates that the pUCARG1140 encoded expression product is suitable for the diagnosis and early detection of NPC.

EXAMPLE 11

Cloning of a Subregion of the Gene Coding for gp 350 in the Vector pUC8

The coding region of gp 250 and gp 350 was mapped to the Bam L-fragment (J. Skare et al., supra) of the EBV B95-8 genome. As both polypeptides share identical regions it was supposed that book proteins are encoded by overlapping reading frames (M. Hummel, D. Thorley-Lawson, E. Kieff, "Epstein-Barr virus DNA fragment encodes messages for the two major envelope glycoproteins (gp 350/300 and gp 220/200)", J. of Virol. 49, p. 413 (1984)). The sequence data of Baer et al. (supra) revealed a large open reading frame including a donor splice site and an acceptor splice site in said Bam L-fragment of the virus genome (FIGS. 17A–D and 18A–B).

It is assumed that gp 350 is the translation product of the unspliced mRNA transcribed from this region and gp 250 is a product of the corresponding spliced mRNA (FIGS. 17A–D). Since both products are found in the viral capsids it is assumed that a differential splicing of said mRNA in a manner comparable with the immunoglobulin heat chain genes (T. Honjo, "Immunoglobulin genes", Ann. Rev. of Immunol., 1, p. 499 (1983)) takes place. During this splicing 630 bp of the mRNA coding for gp 350 are removed to yield the gp 250 coding mRNA (FIGS. 17A–D and 27 (dotted lines ) (R. Baer et al., supra).

Therefore the whole or a part of the reading frame of gp 350 was cloned for finally isolating and producing a gp 350 related product. It should be kept in mind, that not only gp 250 but also gp 350 are highly glycosylated proteins. In contrast, the proteins produced by expression of the recombinant DNA molecules according to the present invention differ from the respective viral proteins normally occuring in nature. If expression is carried out in prokaryotes unmodified proteins are obtained whereas expression in eukaryotes gives proteins with different patterns of glycosylation or else modifications as compared to the natural product.

The Bam L-fragment was introduced in pBR322, and *E. coli* K 12 HB 101 was transformed with the recombinant plasmid obtained. (J. Skare, et al., supra)

Instead of the host *E.coli* K12 HB101 the host bacteria used in the present invention can also be used.

The contents of the publications of M. Hummel et al. (supra), J. R. North et al. (J. R. North, A. J. Morgan, J. L. Thompson, M. A. Epstein, "Purified Epstein-Barr virus M$_r$ 340.000 glycoprotein induces potent virus-neutralizing antibodies when incorporated in liposomes", Proc. Natl. Acad. Sci. USA 79, p. 7504 (1982)) and D. A. Thorley-Lawson and C. A. Poodry ("Identification and Isolation of the Main Component (gp350–gp220) of Epstein-Barr Virus Responsible for Generating Neutralizing Antibodies in Vivo", J. Virol. 43, p. 730 (1984) do not permit predictions that subregions of the gp 250/350 encoding sequence are coding for sufficiently antigenic and/or immunogenic proteins and that these products after selective introduction of these subregions can be stably expressed in prokaryotic and eukaryotic cells. It is therefore surprising that completely unmodified or in a different way modified gp 250/350 related proteins of the present invention are sufficiently active antigens and/or immunogens. In particular in previous publications it was not excluded that minor carbohydrate residues of the protein contribute significantly to the antigenic or immunogenic potential of this protein.

As shown in FIG. 17, a 1.9 kb PstI-PstI-fragment of the Bam L-fragment (Hummel et al., supra) contains the part of the gp 350 coding region beginning at aminoacid position 232 and ending at aminoacid position 825.

A large scale preparation of the pBR 322-BamL plasmid DNA was done according to the method published by H. C. Birnboim and J. Doly ("A rapid alkaline extraction procedure for screening recombinant plasmid DNA", Nucl. Acids Res. 7, p. 1513 (1979)). 50 µg of this DNA were digested for 2 hours at 37° C. with 100 units PstI (Boehringer) in 50 mM NaCl, 10 mM MgCl$_2$, 1 mM DTT, 10 mM Tris-HCl pH 7.5. The digestion was stopped by addition of ⅕ vol. 50 mM EDTA, 60% sucrose, 2% bromphenolblue. The resulting solution was electrophoretically separated on a 1% agarose gel (Seakem, FMC) in Tris-acetate buffer (0.04M Tris-acetate, 2 mM EDTA, pH 7.6). As a size marker HindIII digested λ-phage DNA (Boehringer) was used. After the electrophoresis at 40 V for 14 hours at room temperature (RT), the gel was stained in Tris-acetate buffer containing 0.5 µg/ml ethidium bromide.

The DNA bands in the gel were visualized by UV-illumination and the 1.9 kb PstI-PstI fragment was isolated as described in example 2.

PstI digested DNA of the vector pUC8 was prepared as described before, except that for inhibition of religation of the vector during the following ligase reaction, the DNA was treated with alkaline phosphatase (0.5 units (Boehringer), 30 min at 37° C.).

The concentration of the purified fragments was estimated by electrophoresing 1 µl each in parallel with 100 ng and 500 ng of pUC8-DNA (under conditions described above).

400 ng of the 1.9 kb PstI-PstI-fragment and 100 ng of the PstI digested vector DNA were ligated. *E.coli* K12 JM109 was transformed with the ligated plasmid DNA and positive clones were identified as described in example 2.

The obtained clone was designated *E. coli* K12 JM109 pUCLP1.9 and the resulting recombinant plasmid pUCLP1.9, respectively.

EXAMPLE 12

Cloning of a Subregion of the Gene Coding for gp 350 in the Vector pUR290

For the expression of a stable product of the gp 350 subregion said 1.9 kb PstI-PstI-fragment was reclon in the vector pUR290 (DSM 3417) (FIG. 20) (U. Rüther et al., infra). The resulting recombinant plasmid is coding for a fusion protein of an aminoterminal region of the β-galactosidase, followed by the aminoacids 232 to 825 of gp 350 and aminoacids coded by the cloning-site of pUR290 and pBR322 nucleotide residues. The respective aminoacid sequence is given in FIGS. 21A–F.

50 µg DNA of the plasmid pUCLP 1.9 were digested with 100 units BamHI and HindIII and separated on a 1% agarose gel as described above. The resulting 1.9 kb BamHI/HindIII fragment that contains only a few more nucleotides than the PstI-PstI-fragment originally introduced into pUC8 was separated from the other resulting fragments on a 1% agarose gel (as described above). Finally it was isolated from the gel as described above and ligated into BamHI/HindIII digested DNA of the vector pUR290 (U. Rüther, B. Müller-Hill "Easy identification of cDNA clones", EMBO Journal 10, p. 1791 (1983)) according to the methods described above.

The next step was the transformation of the β-galactosidase repressor-protein overproducer strain *E. coli* K12 JM109 with these recombinant DNA molecules. The transformants were plated and analysed as described above, except that the aliquots of the DNA preparations were digested with BamHI/HindIII and EcoRI. The resulting clone, *E. coli* K12 JM109 pURLP1.9 carries the plasmid pURLP1.9, that is a recombinant of said BamHI-HindIII 1.9 kb fragment of the plasmid pUCLP1.9 and the vector pUR290 (see FIG. 20).

EXAMPLE 13 gp 350 Related Polypeptides Synthesized by *E. coli* K12 JM109 pURLP1.9

In an overnight culture *E. coli* K12 JM109 pURLP1.9 was grown at 37° C. in 5 ml L-broth supplemented with 50 µg/ml Ampicillin. The culture was then diluted to an optical density at 560 nm ($OD_{560}$) of 0.4, and 4 ml of this bacteria suspension were incubated at 37° C. until an $OD_{560}$ of 0.8.

The expression of the genetic information carried by plasmid pURLP1.9 was then induced as described in example 3 and finally the proteins were visualized by coomassie-blue staining as described in example 3.

In comparison with the control experiment, several new proteins, encoded by the plasmid pURLP1.9 and ranging in size from 116 kD to 200 kD, were detected (FIG. 22). The different size of the expression products may be due to incomplete mRNA synthesis or translation. To prove that the new proteins are EBV-related products, all the electrophoretically separated proteins were transferred to a nitrocellulose filter, i.e. a ."Western-blot" was prepared according to the method described in example 3. The results of this experiment are shown in FIG. 22.

EXAMPLE 14

Purification of the β-gal:gp 350 Fusion Protein Encoded by the Plasmid pURLp1.9

The replacement of the natural carboxyterminal amino acid sequence of the β-galactosidase by a gp 350 related amino acid sequence prevents the formation of β-galactosidase tetramers. Furthermore the newly expressed fusion protein is present in a high concentration in the bacterial cell. Therefore the fusion protein precipitates in the cytoplasm of the host cell.

According to the method described in example 4 the clone *E. coli* K12 JM109 pURLP1.9 was used for the production of the corresponding fusion protein.

The results of the several stages of this purification procedure are shown in FIGS. 23A–B.

EXAMPLE 15

Expression of Selected Antigenic Epitopes of gp250/350 as β-galactosidase Fusionproteins FIG. 24 shows the computer-predicted secondary structure of gp350 together with the relative values of hydrophilic (dark circles) and hydrophobic (grey circles) areas. β-turns or loop structures are indicated as line turns of 180° (α-helices, β-sheet and coil structures are barely discernable in the scale used). Based on the assumption that antigenic sites are mainly located in β-turns in an hydrophilic environment, which may be exposes to the surface of the protein, the regions at about aminoacid 50 and aminoacid 740 and 800–830, respectively, are expected to represent antigenic epitopes.

Subcloning and Expression of the N-terminus of gp250/350

The EBV BamHI-L fragment which was cloned in pBR322 (see J. Skare et al., supra) was digested with EcoRI (restriction sites at positions 650 and 1284 in the sequence given in FIGS. 17A–D), the resulting 634 bp fragment was eluted from an agarose gel after electrophoresis and ligated to EcoRI linearised pUC19 (DSM3425) (Yanisch-Perron et al. Gene 33, 103–119 (1985)). Then, *E.coli* K12 JM109 was transformed with the ligation products (all steps were carried out as described in Example 2). According to example 2 the recombinant plasmids obtained were tested for the orientation of their insert-using suitable restriction enzymes. A recombinant plasmid carrying the insert in the opposite orientation of the reading frame relative to the reading frame of the lacZ gene of the pUC19 plasmid was designated as pUC19LEP600 and used for further cloning.

pUC19LEP600 was digested with BamHI and PstI (the BamHI site is derived from pUC19, the PstI site corresponds to position 1248 in FIGS. 17A–D), the resulting 600 bp fragment was inserted into pUR291 (DSM3418) (Rüther, supra), previously digested with BamHI and PstI. The resulting recombinant plasmid pURLEP600 displayed the following sequence in its linker region at the C-terminus of the β-galactosidase:

```
   pUR291    /    pUC19              /         gp250/350
β-galTGT CGG GGA TCC CCG GTA CCG GAG CTC GAA TTC CCA TTT - - - ACC
/ pUR291
TGC AGC CAA GCT TAT CGA TGA
```

The expression of the fusion protein from this recombinant plasmid after IPTG-induction was carried out as described in example 3. The result of this experiment is shown in FIGS. 25A–B. From FIG. 25B it can be taken that the expression product obtained is recognized as a moderately antigenic protein by a pool of NPC-sera.

Subcloning and Expression of the C-terminus of gp250/350

The region covering the antigenic epitopes near the C-terminus which, according to the computer-directed analysis, also is expected to be antigenic, was isolated by digesting the plasmid pUCLP1.9 (see example 11) with XmnI (restriction site at position 2760 in FIGS. 17A–D) and HindIII (restriction site in the region derived from the pUC-plasmid). The purified 386 bp fragment was inserted into pUC19 previously digested with HindII and HindIII. The resulting plasmid which was introduced into *E.coli* K12 JM109 is pUC19LXP390.

The insert of pUC19LXP390 was cut out with BamHI and HindIII and ligated into pUR288 digested with the same enzymes. The resulting recombinant plasmid was introduced into *E.coli* K12 JM109 and was designated as pURLXP390. The sequence in its linker region is as follows:

```
   pUR288    /    pUC19    /      gp350          /    pUC8    /
β-gal-TGT CGG GGA TCC TCT AGA GTC AGT TCC CAC - - - GTA CTG CAG CCA AGC
pUR288
TTA TCG
```

After IPTG-induction a β-galactosidase fusion protein was synthesized by said transformed host. In a Western blot the expression product shows a high reactivity with the NPC sera pool (see FIG. 25B, lower part).

EXAMPLE 16

Use of the β-gal::gp250/350 Fusion Proteins Encoded by the Newly Constructed Recombinant Plasmids in Diagnostic Tests Jilg et al. (W. Jilg and H. Wolf, "Diagnostic Significance of Antibodies to the Epstein-Barr Virus-Specific Membrane Antigen gp250", The Journal of Infectious Diseases, 152, 222–225(1985)) have shown the validity of gp250 and gp350 as antigens for the determination of the immune status to EBV and especially for the diagnosis of chronic EBV-infections. Persons showing a normal immune response after an EBV-infection possess antibodies against gp250 and gp350, whereas patients suffering from chronic EBV-infection show an immune response only to gp350 which still contains the additional intron sequence (see FIG. 27). The serological status of these persons can be checked in ELISA tests using the three fusion proteins, purified according to the method given in example 4. An antibody reaction to all three fusion proteins indicates a normal immune status. If there-is nor or weaker reaction with the proteins encoded by pURLEP600 and pURLXP390, but reactivity against pURLP1.9 (which contains the intron sequences, see FIG. 27) a chronic EBV-infection is very likely.

IgA antibodies to the membrane protein gp250/350 and to subfragments thereof are absent in the normal population, but present in 58% of Nasopharyngeal Carcinoma patients when measured in a relatively insensitive immunofluorescence assay. These results are similar to the detection rate of IgA antibodies to EBV specific early antigens in comparable testsystems. In analogy the more sensitive ELISA test brings the detection rate close to 100% with only minimal increase of false positive results. Therefore the antigens encoded by the newly constructed recombinant plasmids pURLEP600, pURLXP390, and pURLP1.9, respectively, are valuable substances for the initial diagnosis and the control of a therapy of Nasopharyngeal Carcinoma.

EXAMPLE 17

Expression of the N-terminal gp250/350 Fragment in the Plasmid pUC8

The recombinant plasmid covering the N-terminal region of gp250/350, pUC19LEP600 (see example 15), was digested with BamHI and PstI. The EBV derived fragment was isolated and ligated into pUC8, previously digested with the same enzymes. The sequence in the linker region of the resulting clone, pUCLEP600, is the following:

```
/      pUC8      /    pUC19               /     gp350
ATT ACG AAT TCC CGG GGA TCC CCG GGT AAC GAG CTC GAA TTC CCA
                                    pUC8
TTT - - - ACC TGC AGC CAA GCT TAT
```

After induction with IPTG/the fusion protein encoded by pUCLEP600 is quite stable in the bacterial cells and is recognized as an antigen by the NPC sera pool (see FIG. 26). The bacterial fusion part consists of 14 aminoacids at the N-terminus and 9 at the C-terminus. The value of this protein is its applicability in a vaccine, especially when it is fused with the per se instable second antigenic region from the C-terminus as it was determined with the β-gal fusion proteins (see example 15).

The inserts of the recombinant expression plasmids and cloning plasmids constructed according to examples 11 and 15 to 17 are summarized in FIG. 27.

EXAMPLE 18

Expression of the N-terminal Part of gp250/350 as a p138::gp250/350 Fusion Protein The plasmid pUC19LEP600 (see example 15) was digested with PstI and the resulting 600bp fragment was ligated to the PstI linearised plasmid pUCARG601 (see example 7). The gp350-insert was checked to be in the same orientation as the pUCARG601-reading frame and the resulting recombinant plasmid was designated as pUCARG1230. The sequence in the linker region and at the junction sites of the obtained plasmids is the following:

```
      pUC8      /  pUC12/       p138    /      pUC19
ATG ACC ATG ATT ACG AAT TCG AGC TCT CTG ACC- - - ATC CTG CAG GTC GAC
TCT AGA

/     gp350      / pUCARG601
GAA TCC CCG GGT ACC GAG CTC GAA TTC CCA TTT - - - ACC TGC AGC GTC GTC
GTC GTC GTT GAT AAC GTT
```

After induction with IPTG, *E.coli* K12 JM109 carrying pUCARG1230 expresses a stable and antigenic protein which consists of antigenic regions from two different proteins, namely p138 and gp250/350 (see FIG. 26).

Furthermore it can be used as antigen in ELISA tests and also for vaccination.

EXAMPLE 19

Neutralisation Test with Sera Derived from Rabbits Immunized with gp250/350 Antigens Supernatants from B95-8 cells were used to immortalize human umbilical cord blood cells (Lymphocyte fraction from Ficol/Hypaque gradient). $0.5 \times 10^6$ lymphocytes were seeded per 0.5 ml microtiter plate well and 50 µl of a cell-free supernatant of B95-8 cells were added and allowed to adsorb for 2 hours at 37° C. After incubation the virus-containing medium was removed, cells were washed with RPMI1640 medium containing 10% fetal calf serum and incubated in 200 µl of the same medium at 37° C. in a 5% $CO_2$ atmosphere. Developing colonies of lymphoblastoid cells were evaluated not sooner than three weeks after the start of the experiment and counted as positive transformation.

The neutralizing properties of serawere tested by preincubating for 1 hour under slight agitation aliquotes of the Epstein-Barr Virus containing B95-8 cell supernatant with 20 µl of test serum including the respective preimmunization serum as control in a replicate test before the supernatant was allowed to adsorb to the umbilical cord blood lymphocytes. After removing the inoculum from the cells after 2 hours the maintenance medium (RPMI1640 supplemented with 10% FCS) was supplemented with 5% of the respective sera under test for neutralizing activity. The following results were obtained:

| PBS (control) (no virus) | Virus + EBV negative human serum | Virus + EBV positive human serum pool | Virus + rabbit pre-serum | Virus + rabbit immune serum 1 | Virus + rabbit immune serum 2 |
|---|---|---|---|---|---|
| no colonies | colonies | no colonies | colonies | no colonies | no colonies |

EXAMPLE 20

Cloning and Expression of Antigenic Fragments of the Virus-capsid Protein p150

The coding sequence of the diagnostically relevant protein p 150 (Virus capsid antigen VCA (see Example 1, FIGS. 28D-1 to 28D-10) was examined for antigenic sites and subcloned for the expression as β-galactosidase fusion proteins. The N-terminal region which is expected to encode an antigenic site was obtained by digestion of the Charon 4A phage EB 69–79 (G. N. Buell, D. Reisman, C. Kintner, G. Crouse, and B. Sugden, "Cloning overlapping DNA fragments from the B95-8 strain of Epstein-Barr virus (ATCC CRL 1612) reveals a site of homology to the internal repetition", Journal of Virology 40, 977–982 (1981)) with BamHI and a resulting 1176 bp fragment was cloned into the BamHI site of pUC12. From a resulting plasmid with the insertion in the proper orientation a 580 bp fragment was excised with XhoI/SalI. The SalI site derives from the pUC12 linker, the XhoI site is located 33bp upstream from the start of p150. This fragment was inserted into pUC8 digested with SalI (SalI and XhoI share the same sticky end sequence). The resulting clones were screened to have the p150 start codon next to the BamHI site. From a proper clone the p150 encoding region was cut out with BamHI and HindIII and cloned into pUR290 digested with BamHI and HindIII (pUR290CXH580). The expression of the β-Gal::p150 fusion protein from this clone is shown in FIG. 29. Its ability to react very well with a NPC serum pool can be taken from FIG. 30.

Further, p150::β-gal fusion constructs were obtained accordingly. For example the subclones pUR290DBX320, pUR292DBB180, pUR288DTT700, pUR288DTT740, pUR290DTP680, pUR288DPP320 which are indicated in FIG. 31. From the designation of the subclones, the vector used can be taken, e.g. for the construction of subclone pUR290DBX320 the vector pUR290 was used.

From FIG. 30 the restriction enzyme sites used for subcloning can also be taken. All clones with the exception of pURDBB180 were constructed by subcloning the desired fragments into pUC8 or pUC12 (see supra) to obtain BamHI and HindIII sites suitable for the cloning to pUR vectors (see supra). pUR292DBB180 was derived by insertion of the 180 bp BglII-BglII fragment (see FIG. 31) into pUR292 linearized with BamHI. FIGS. 29 and 30 show their expression and antigenicity.

The β-gal::p150 fusion protein encoded by pUR290CXH580 and purified according to example 4 reacts in the ELISA test as an EBV specific antigen indicating its applicability in diagnosis. Stable expression was also obtained with the N-terminal fragment of p150 by inserting the 580 bp fragment (used for the construction of pUR290CSH580) into pUC18 (DSM 3424) using the BamHI and HindIII site. The resulting clone pUC18CXH580 expresses a stable and antigenic protein of about 25 kD in size.

The following deposited plasmids, host bacteria and cell lines were used for the purpose of the present invention. The deposition was affected according to the Budapest treaty

| m.o. | depository | deposition number |
| --- | --- | --- |
| B 95.8 | ATCC | CRL 1612 |
| E. coli K12 JM83 | ATCC | 35607 |
| E. coli K12 BMH71-18 | DSM | 3413 |
| E. coli K12 JM109 | DSM | 3423 |
| pUC8 | DSM | 3420 |
| pUC9 | DSM | 3421 |
| pUC12 | DSM | 3422 |
| pUC19 | DSM | 3425 |
| pUR288 | DSM | 3415 |
| pUR290 | DSM | 3417 |
| pUR291 | DSM | 3418 |
| pUCARG680 | DSM | 3408 |
| pUC18 | DSM | 3424 |

While we have hereinbefore presented a number of embodiments of this invention, it is apparent that our constructions can be altered to provide other embodiments which utilize DNA sequences of the EBV genome coding for EBV-related antigens and for producing recombinant DNA molecules. It is obvious to those skilled in the art than other DNA sequences may also be used, which are related to said DNA sequences and which may be derived from other EBV serotypes. The EBV is easily obtainable from known natural sources, e. g. from the saliva of infected patients.

It is obvious that for obtaining biologically comparable results other suitable vector/host systems can be used. The invention is not limited to host/vector systems presently available.

I claim:

1. An isolated EBV-related protein which is encoded by a nucleotide sequence selected from the group consisting of:
   (a) the region of the EBV genome encoding the EBV protein p150, said region consisting of the coding DNA sequence as shown in FIG. 28D beginning with nucleotide 1 and ending at nucleotide 4143;
   (b) the region of the EBV genome encoding the EBV protein p143, said region consisting of the coding DNA sequence as shown in FIG. 28C beginning with nucleotide 1 and ending at nucleotide 3954;
   (c) the region of the EBV genome encoding the EBV protein p138, said region consisting of the coding DNA sequence as shown in FIG. 3 beginning with nucleotide 1 and ending at nucleotide 3384;
   (d) the region of the EBV genome encoding the EBV protein p90, said region consisting of the coding DNA sequence as shown in FIG. 28B beginning with nucleotide 1 and ending at nucleotide 2478; and
   (e) the region of the EBV genome encoding the EBV protein p54, said region consisting of the coding DNA sequence as shown in FIG. 28A beginning with nucleotide 1 and ending at nucleotide 1212.

2. An isolated protein consisting of an amino acid sequence selected from the group consisting of:
   (a) AspProThrPheThrGluArgGlyPheSerLysThrValLysSer AspLeuIleAlaMet-PheLysArgHisLeuLeuGluHisSer-PhePheLeuAspArgAla GluAsnMetGlySerGlyPheSerGln-TyrValArgSerArgLeuSerGluMetValAla AlaValSerGly-GluSerValLeuLysGlyValSerThr-TyrThrThrAlaLysGlyGly GluProValGlyGlyValPheIle-eValThrAspAsnValLeuArgGlnLeuLeuThrPhe LeuGlyGluGluAlaAspAsnGlnIleMetGlyProSer;
   (b) IlePheTyrTyrValPheLeuProThr-CysThrAsnAlaHisMetCys GlyLeuGlyValAspPheGln-HisValAlaGlnThrLeuAlaTyrAsnGlyProAlaPhe SerHisHisPheThrArgAspGluAspIleLeuAspAsnLeu-GluAsnGlyThrLeuArg AspLeuLeuGluIle;
   (c) ValGluAlaMetIleHisGlyPheGluG-luLysPheValMetAsn ValProLeuValSer-LeuCysIleAsnThrTyrTrpGluArgSerGlyArgLeuAlaPhe ValAsnSerPheSerMetIleLysPheI-leCysArgHisLeuGlyAsnAsnAlaIleSer LysGlu-AlaTyrSerMetTyrArgLysIleTyrG-lyGluLeuIleAlaLeuGluGlnAla LeuMetArgLeuAlaGlySerAspVal-ValGlyAspGluSerValGlyGlnTyrValCys Ala-LeuLeuAspProAsnLeuLeuPro-ProValAlaTyrThrAspIlePheThrHisLeu LeuThrValSerAspArgAlaPro-GlnIleIleIleGlyAsnGluValTyrAlaAspThr LeuAlaAla-ProGlnPheIleGluArgValGlyAsn-MetAspGluMetAlaAlaGlnPhe ValAlaLeuTyrGlyTyrArgValAsnG-lyAspHisAspHisAspPheArgLeuHisLeu GlyProTyrV-alAspGluGlyHisAlaAspValLeuG-luLysIlePheTyrTyrValPhe LeuProThrCysThrAsnAlaHisMet-CysGlyLeuGlyValAspPheGlnHisValAla GlnThr-LeuAlaTyrAsnGlyProAlaPheSerH-isHisPheThrArgAspGluAspIle LeuAsp;
   (d) AspAsnLeuGluAsnGlyThrLeuArgAspLeuLeuGluIle SerAspLeuArgProThrValGly-MetIleArgAspLeuSerAlaSerPheMetThrCys ProThr-PheThrArgAlaValArgValSerVal-AspAsnAspValThrGlnGlnLeuAla ProAsnProAlaAspLysArgThr-GluGlnThrValLeuValAsnGlyLeuValAlaPhe AlaPhe-SerGluArgThrArgAlaValThrGln-CysLeuPheHisAlaIleProPheHis MetPheTyrGlyAspProArgValA-laAlaThrMetHisGlnAspValAlaThrPheVal MetArgAs-nProGlnGlnArgAlaValGluAl-aPheAsnArgProGluGlnLeuPheAla GluTyrArgGluTrpHisArgSerProM-etGlyLysTyrAlaAlaGluCysLeuProSer Leu-ValSerIleSerGlyMetThrAlaMe-tHisIleLysMetSerProMetAlaTyrIle AlaGlnAlaLysLeuLysIleHisPro-GlyValAlaMetThrValValArgThrAspGlu IleLeuSer-GluAsnIleLeuPheSerSerArgAla-SerThrSerMetPheIleGlyThr ProAsnValSerArgArgGluA-laArgValAspAlaValThrPheGluValHisHisGlu MetAla-SerIleAsp;
   (e) SerThrMetThrProAlaArgValAlaAlaIle ThrThrAsp-MetGlyIleHisThrGlnAspPhePhe-SerValPheProAlaGluAlaPhe GlyAsnGlnGlnValAs-nAspTyrIleLysAlaLysValGlyAlaGlnArgAsnGlyThr LeuLeuArgAspProArgThrTyr-LeuAlaGlyMetThrAsnValAsnGlyAlaProGly LeuCysHisGlyGlnGlnAlaThrCysGlu-
IleIleValThrProValThrAlaAspVal
AlaTyrPheGlnLysSerAsnSer-
ProArgGlyArgAlaAlaCysValValSerCysGlu Asn-
TyrAsnGlnGluValAlaGluGlyLeuI-
leTyrAspHisSerArgproAspAlaAla
TyrGluTyrArgSerThrValAsnPro-
TrpAlaSerGlnLeuGlySerLeuGlyAspIle Met-
TyrAsnSerSerTyrArgGlnThrAla-
ValProGlyLeuTyrSerProCysArgAla
PhePheAsnLysGluGluLeuLeuArg-
AsnAsnArgGlyLeuTyrAsnMetValAsnGlu TyrSerGlnAr-
gLeuGlyGlyHisProAlaTh-
rSerAsnThrGluValGlnpheValVal
IleAlaGlyThrAspValPheLeuGluGlnProCys;

(f) LeuGlnGluAlaPheProAlaLeuSerAlaSerSerArg Ala-
LeuIleAspGluPheMetSerValLys-
GlnThrHisAlaProIleHisTyrGlyHis TyrIleIleGluGluV-
alAlaProValArgArgIleLeuLysPheGlyAsnLysValVal
Phe; and (g) Met AlaSerAsnGluGlyValGluAsnArg-
ProPheProTyrLeuThrValAspAlaAspLeu LeuSerAsn-
LeuArgGlnSerAlaAlaGluGlyLe-
uPheHisSerPheAspLeuLeuVal
GlyLysAspAlaArgGluAlaGly-
IleLysPheGluValLeuLeuGlyValTyrThrAsn AlaIleGln-TyrValArgPheLeuGluThrAlaLeuA-laValSerCysValAsnThrGlu PheLysAspLeuSerArgMetThrAspG-lyLysIleGlnPheArgIleSerValProThr IleAlaHisGl-yAspGlyArgArgProSerLys-GlnArgThrPheIleValValLysAsn CysHisLysHisIleSerThrGlu-MetGluLeuSerMetLeuAspLeuGluIleLeu HisSer-IleProGluThrProValGluTyrAla-GluTyrValGlyAlaValLysThrVal AlaSerAlaLeuGlnPheGlyV-alAspAlaLeuGluArgGlyLeuIleAsnThrValLeu SerVal-LysLeu.

3. An isolated protein consisting of an amino acid sequence selected from the group consisting of:

(a) GluAlaLeuCysGlyGluThrArgGlu ValPheGly-TyrAspAlaTyrSerAlaLeuProArg-GluSerSerLysProGlyAspPhe PheProGluGlyLeuAsp-ProSerAlaTyrLeuGlyAlaValAlaIleThrGluAlaPhe LysGluArgLeuTyrSerGlyAsnLeu-ValAlaIleProSerLeuLysGlnGluValAla ValGlyGlnSer-AlaSerValArgValProLeuTyrAs-pLysGluValPheProGluGly ValProGlnLeuArgGlnPheT-yrAsnSerAspLeuSerArgCysMetHisGluAlaLeu TyrThrGlyLeuAlaGlnAla-LeuArgValArgArgValGlyLysLeuValGluLeuLeu Glu-LysGlnSerLeuGlnAspGlnAlaLys-ValAlaLysValAlaProLeuLysGluPhe ProAlaSerThrIleSerHisProAspS-erGlyAlaLeuMetIleValAspSerAlaAla CysGluLeuAla-ValSerTyrAlaProAlaMetLeuGlu-AlaSerHisGluThrProAla SerLeuAsnTyrAspSerTrpProLe-uPheAlaAspCysGluGlyProGluAlaArgVal AlaAlaLeu-HisArgTyrAsnAlaSerLeuAlaPro-HisValSerThrGlnIlePheAla ThrAsnSerValLeuTyrValSerGly-ValSerLysSerThrGlyGlnGlyLysGluSer LeuPheAsnSerPheTyrMetThrHisG-lyLeuGlyThrLeuGlnGluGlyThrTrpAsp ProCysAr-gArgProCysPheSerGlyTrpGlyG-lyProAspValThrGlyThrAsnGly ProGlyAsnTyrAlaValGluHisLeu-ValTyrAlaAlaSerPheSerProAsnLeuLeu AlaArg-TyrAlaTyrTyrLeuGlnPheCysGlnG-lyGlnLysSerSerLeuThrProVal ProGluThrGlySerTyrValAlaGlyA-laAlaAlaSerProMetCysSerLeuCysGlu GlyArgAla-ProAlaValCysLeuAsnThrLeuPheP-heArgLeuArgAspArgPhePro ProValMetSerThrGlnArgArgAsp-ProTyrValIleSerGlyAlaSerGlySerTyr AsnGluThrAsp-PheLeuGlyAsnPheLeuAsn-PheIleAspLysGluAspAspGlyGln ArgProAspAspGluProArgTyrThr-TyrTrpGlnLeuAsnGlnAsnLeuLeuGluArg LeuSerAr-gLeuGlyIleAspAlaGluGlyLysLeu-GluLysGluProHisGlyProArg AspPheValLysMetPheLysAspV-alAspAlaAlaValAspAlaGluValValGlnPhe MetAsnSer-MetAlaLysAsnAsnIleThr-TyrLysAspneuValLysSerCysTyrHis ValMetGlnTyrSerCysAsnProPh-eAlaGlnProAlaCysProIlePheThrGlnLeu PheTyrArg-SerLeuLeuThrIleLeuGlnAspIle-SerLeuProIleCysMetCysTyr GluAsnAspAsnProGlyLeuG-lyGlnSerProProGluTrpLeuLysGlyHisTyrGln Thr-LeuCysThrAsnPheArgSer-LeuAlaIleAspLysGlyValLeuThrAlaLysGlu AlaLysValValHisGlyGluProThr-CysAspLeuProAspLeuAspAlaAlaLeuGln GlyArgVal-TyrGlyArgArgLeuProValArgMet-SerLysValLeuMetLeuCysPro ArgAsnIleLysIleLysAsnArgVal-ValPheThrGlyGluAsnAlaAlaLeuGlnAsn Ser-PheIleLysSerThrThrArgGlu-AsnTyrIleIleAsnGlyProTyrMetLys PheLeuAsnThrTyrHisLysThrLe-uPheProAspThrLysLeuSerSerLeuTyrLeu TrpHisAsn-PheSerArgArgArgSerValProVal-ProSerGlyAlaSerAlaGluGlu TyrSerAspLeuAlaLeuPheValAspG-lyGlySerArgAlaHisGluGluSerAsnVal IleAspValVal-ProGlyAsnLeuValThrTyrAlaLys-GlnArgLeuAsnAsnAlaIle LeuLysAlaCysGlyGlnThrGlnPheT-yrIleSerLeuIleGlnGlyLeuValProArg ThrGlnSerVal-ProAlaArgAspTyrProHisValneuG-lyThrArgAlaValGluSer AlaAlaAlaTyrAlaGluAlaThrSer-SerLeuThrAlaThrThrValValCysAlaAla ThrAsp-CysLeuSerGlnValCysLysAlaArg-ProValValThrLeuProValThrIle AsnLysTyrThrGlyValAsnGlyAs-nAsnGlnIlePheGtnAlaGlyAsnLeuGlyTyr PheMetGl-yArgGlyValAspArgAsn-LeuLeuGlnAlaProGlyAlaGlyLeuArgLys GlnAlaGlyGlySerSerMetAr-gLysLysPheValPheAlaThrProThrLeuGlyLeu ThrVal-LysArgArgThrGlnAlaAlaThrThr-TyrGluIleGluAsnIleArgAlaGly LeuGluAlaIleIleSerGlnLysGln-GluGluAspCysValPheAspValValCysAsn LeuV-alAspAlaMetGlyGluAlaCysAla-SerLeuThrArgAspAspAlaGluTyrLeu LeuGlyArgPheSerValLeuAlaAspSerValLeuGluThrLeuAlaThrIleAlaSer SerGlyIle-
GluTrpThrAlaGluAlaAlaArgAsp-
PheLeuGluGlyValTrpGlyGly
ProGlyAlaAlaGlnAspAsn-
PheIleSerValAlaGluProValSerThrAlaSerGln AlaSer-
AlaGlyLeuLeuLeuGlyGlyGlyG-
lyGlnGlySerGlyGlyArgArgLysArg
ArgLeuAlaThrValLeuProGlyLeu;

(b) GluAlaLeuCysGlyGluThrArgGlu ValPheGly-
TyrAspAlaTyrSerAlaLeuProArg-
GluSerSerLysProGlyAspPhe PheProGluGlyLeuAsp-
ProSerAlaTyrLeuGlyAlaValAlaIleThrGluAlaPhe
LysGluArgLeuTyrSerGlyAsnLeu-
ValAlaIleProSerLeuLysGlnGluValAla ValGlyGlnSer-
AlaSerValArgValProLeuTyrAs-
pLysGluValpheproGluGly
ValProGlnLeuArgGlnPheT-
yrAsnSerAspLeuSerArgCysMetHisGluAlaLeu
TyrThrGlyLeuAlaGlnAla-
LeuArgValArgArgValGlyLysLeuValGluLeuLeu Glu-
LysGlnSerLeuGln;

(c) LeuGlnAspGlnAlaLysValAla LysValAlaProLeuLys-
GluPheProAlaSerThrIleSerHisProAspSerGlyAla Leu-
MetIleValAspSerAlaAlaCysG-
luLeuAlaValSerTyrAlaProAlaMetLeu
GluAlaSerHisGluThrProAlaSer-
LeuAsnTyrAspSerTrpProLeuPheAlaAsp CysGluG-
lyProGluAlaArgValAlaAlaLeu-
HisArgTyrAsnAlaSerLeuAlaPro
HisValSerThrGlnIlePheAlaTh-
rAsnSerValLeuTyrValSerGlyValSerLys SerThrG-
lyGlnGlyLysGluSerLe-
uPheAsnSerPheTyrMetThrHisGlyLeuGly ThrLeuGln;

(d) LeuGlnPheCysGlnGlyGlnLys SerSerLeuThrProVal-
ProGluThrGlySerTyrValAlaGlyAlaAlaAlaSerPro
MetCysSerLeuCysGluGlyArgAla-
ProAlaValCysLeuAsnThrLeuPhePheArg LeuArgAs-
pArgPheProProValMetSerThr-
GlnArgArgAspProTyrValIleSer
GlyAlaSerGlySerTyrAsn-
GluThrAspPhaLeuGlyAsnPheLeuAsnPheIleAsp Lys-
GluAspAspGlyGlnArgProAspAspG-
luProArgTyrThrTyrTrpGlnLeuAsn
GlnAsnLeuLeuGluArgLeuSerAr-
gLeuGlyIleAspAlaGluGlyLysLeuGluLys GluProHis-GlyProArgAspPheValLysMet-PheLysAspValAspAlaAlaValAsp AlaGluValValGlnPheMetAsnSer-MetAlaLysAsnAsnIleThrTyrLysAspLeu ValLysSerCy-sTyrHisValMetGlnTyrSerCysAsn-ProPheAlaGlnProAlaCys ProIlePheThrGlnLeuPheTyrArg-SerLeuLeuThrIleLeuGln;

(e) LeuGlnAspIleSerLeuProIle CysMetCysTyrGluAs-nAspAsnProGlyLeuGlyGlnSerProProGluTrpLeuLys GlyHisTYrGlnThrLeuCysThrAsn-PheArgSerLeuAlaIleAspLysGlyValLeu ThrAlaLys-GluAlaLysValValHisGlyGluPro-ThrCysAspLeuProAspLeuAsp AlaAlaLeuGln;

(f) LeuGlnGlyArgValTyrGlyArg ArgLeuProValArgMet-SerLysValLeuMetLeuCysProArgAsnIleLysIleLys AsnArgValValPheThrGlyGluAsnA-laAlaLeuGlnAsnSerPheIleLysSerThr ThrArgArgGlu-AsnTyrIleIleAsnGlyPro-TyrMetLysPheLeuAsnThrTyrHis LysThrLeuPheProAspThrLysLeuS-erSerLeuTyrLeuTrpHisAsnPheSerArg ArgArgSerVal-ProValProSerGlyAlaSerAlaGlu-GluTyrSerAspLeuAlaLeu PheValAspGlyGlySerArgAlaHis-GluGluSerAsnValIleAspValValProGly AsnLeuValThr-TyrAlaLysGlnArgLeuAsnAs-nAlaIleLeuLysAlaCysGlyGln ThrGlnPheTyrIleSerLeuIleGlnG-lyLeuValProArgThrGlnSerValProAla ArgAspTyrPro-HisValLeuGlyThrArgAlaVal-GluSerAlaAlaAlaTyrAlaGlu AlaThrSerSerLeuThrAlaThrThr-ValValCysAlaAlaThrAspCysLeuSerGln ValCysLysA-laArgProValValThrLeuProValTh-rIleAsnLysTyrThrGlyVal AsnGlyAsnAsnGlnIlePheGlnAlaG-lyAsnLeuGlyTyrPheMetGlyArgGlyVal AspArgAsn-LeuLeuGln;

(g) LeuGlnAlaProGlyAlaGlyLeu ArgLYsGlnAlaGlyGly-SerSerMetArgLysLyspheValpheAlaThrProThrLeu GlyLeuThrValLysArgArgThrGlnA-laAlaThrThrTyrGluIleGluAsnIleArg AlaGlyLeuGlu-AlaIleIleSerGlnLysGlnGluGlu-AspCysValPheAspValVal CysAsnLeuValAspAlaMetGlyGluA-laCysAlaSerLeuThrArgAspAspAlaGlu TyrLeuLeuGl-yArgPheSerValLeuAlaAspSerVal-LeuGluThrLeuAlaThrIle AlaSerSerGlyIleGluTrpThrAla-GluAlaAlaArgAspPheLeuGluGlyValTrp GlyGlyPro-GlyAlaAlaGlnAspAsnPheIleSer-ValAlaGluProValSerThrAla SerGlnAlaSerAlaGlyLeuLeuLeuG-lyGlyGlyGlyGlnGlySerGlyGlyArgArg LysArgAr-gLeuAlaThrValLeuProGlyLeu;

(h) GlnThrSerGluAspAsnLeuGlySerGln SerGlnPro-GlyProCysGlyTyrIleTyrPheTyr-ProLeuAlaThrTyrProLeuArg GluValAlaThrLeuG-lyThrGlyThrAlaGlyHisArgCysLeuThrValProLeuLeu CysGlyIleThrValGluProGlyPhe-SerIleAsnValLysAlaLeuHisArgArgPro AspProAsn-CysGlyLeuLeuArgAlaThrSer-TyrHisArgAspIleTyrValPheHis AsnAlaHisMetValProProIlePhe-GluGlyProGlyLeuGluAlaLeuCysGlyGlu ThrArgGlu-ValPheGlyTyrAspAlaTyrSerAla-LeuProArgGluSerSerLysPro GlyAspPhePheProGluGlyLeuAsp-ProSerAlaTyrLeuGlyAlaValAlaIleThr GluAlaPheLys-GluArgLeuTyrSerGlyAsnLeuValA-laIleProSerLeuLysGln GluValAlaValGlyGlnSerAlaSer-ValArgValProLeuTyrAspLysGluValPhe ProGluGly-ValProGlnLeuArgGlnPheT-yrAsnSerAspLeuSerArgCysMetHis GluAlaLeuTyrThrGlyLeuAla-GlnAlaLeuArgValArgArgValGlyLysLeuVal GluLeuLeuGluLysGlnSerLeuGln;

(i) IlePheAlaThrAsnSerVal LeuTyrValSerGlyValSerLys-SerThrGlyGlnGlyLysGluSerLeuPheAsnSer PheT-yrMetThrHisGlyLeuGlyThr-LeuGlnGluGlyThrTrpAspProCysArgArg ProCysPheSerGlyTrpGlyG-lyProAspValThrGlyThrAsnGlyProGlyAsnTyr AlaVal-GluHisLeuValTyrAlaAlaSerPhe-SerProAsnLeuLeuAlaArgTyrAla TyrTyrLeuGlnPheCysGlnGlyGlnLysSerSerLeuThrProValProGluThrGly SerTyrVal AlaGlyAlaAlaAlaSerProMet-
CysSerLeuCysGluGlyArgAlaPro
AlaValCysLeuAsnThrLeuPhePhe-
ArgLeuArgAspArgPheProProValMetSer ThrGlnArgArgAspProTyrValIleSerGlyAla-
SerGlySerTyrAsnGluThrAsp
PheLeuGlyAsnPheLeuAsn-
PheIleAspLysGluAspAspGlyGlnArgProAspAsp Glu-
ProArgTyrThrTyrTrpGlnLeuAs-
nGlnAsnLeuLeuGluArgLeuSerArgLeu
GlyIleAspAlaGluGlyLysLeuGlu-
LysGluProHisGlyProArgAspPheValLys Met-
PheLysAspValAspAlaAlaVa-
lAspAlaGluValValGlnPheMetAsnSerMet
AlaLysAsnAsnIleThrTyrLysAs-
pLeuValLysSerCysTyrHisValMetGlnTyr SerCysAsn-
ProPheAlaGlnProAlaCysProIle-
PheThrGlnLeuPheTyrArgSer
LeuLeuThrIleLeuGlnAspIleSer-
LeuProIleCysMetCysTyrGluAsnAspAsn Pro-
GlyLeuGlyGlnSerProProGluTr-
pLeuLysGlyHisTyrGlnThrLeuCysThr
AsnPheArgSerLeuAlaIleAspLysG-
lyValLeuThrAlaLysGluAlaLysValVal HisGlyGluPro-

GluIleGluAsnIleArgAlaGlyLeu-
GluAlaIleIleSerGlnLysGlnGluGlu
AspCysValPheAspValValCysAsn-
LeuValAsPAlaMetGlyGluAlaCysAlaSer LeuThrAr-
gAspAspAlaGluTyrLeuLeuGlyArg-
PheSerValLeuAlaAspSerVal
LeuGluThrLeuAlaThrIleAlaSer-
SerGlyIleGluTrPThrAlaGluAlaAlaArg AspPheLeu-
GluGlyValTrpGlyGlyProGlyA-
laAlaGlnAspAsnPheIleSerVal
AlaGluProValSerThrAlaSer-
GlnAlaSerAlaGlyLeuLeuLeuGlyGlyGlyGly GlnGly-
SerGlyGlyArgArgLysArgAr-
gLeuAlaThrValLeuProGlyLeuGluVal;

(k) GluAlaLeuCysGlyGluThrArgGluValPheGlyTyr
AspAlaTyrSerAlaLeuProArgGluS-
erSErLysProGlyAspPhePheProGluGly LeuAspProS-
erAlaTyrLeuGlyAlaValAlaI-
leThrGluAlaPheLysgluArgLeu
TyrSerGlyAsnLeuValAlaIlePro-
SerLeuLysGlnGluValAlaValGlyGlnSer AlaSerVal-
ArgValProLeuTyrAspLysGluVAl-
PheProGluGlyValProGlnLeu
ArgGlnPheTyrAsnSerAspLeuSer-
ArgCysMetHisGluAlaLeuTyrThrGlyLeu AlaGlnAla-
LeuArgValArgArgValGlyLysLeu-
ValGluLeuLeuGluLysGlnSer
LeuGlnAspGlnAlaLysValAlaLys-
ValAlaProLeuLysGluPheProAlaSerThr IleSerHis-
ProAspSerGlyAlaLeuMetIl-
eValAspSerAlaAlaCysGluLeuAla
ValSerTyrAlaProAlaMetLeuGlu-
AlaSerHisGluThrProAlaSerLeuAsnTyr AspSerTrp-
ProLeuPheAlaAspCysGluGlyPro-
GluAlaArgValAlaAlaLeuHis
ArgTyrAsnAlaSerLeuAlaProHis-
ValSerThrGlnIlePheAlaThrAsnSerVal LeuTyrValSer-
GlyValSerLysSerThrGlyGlnG-
lyLysGluSerLeuPheAsnSer
P (m) LeuGlnAlaProGlyAlaGlyLeuArgLysGlnAlaGly Gly-SerSerMetArgLysLysPheVal-PheAlaThrProThrLeuGlyLeuThrValLys ArgArgThrGlnAlaAlaThrThrTyrGluIleGluAsnIleArg-AlaGlyLeuGluAla IleIleSerGlnLysGlnGluGluAsp-CysValPheAspValValCysAsnLeuValAsp AlaMetGly-GluAlaCysAlaSerLeuThrAr-gAspAspAlaGluTyrLeuLeuGlyArg PheSerValLeuAlaAspSerValLeu-GluThrLeuAlaThrIleAlaSerSerGlyIle GluTrpThrAla-GluAlaAlaArgAspPheLeuGluGly-ValTrpGlyGlyProGlyAla AlaGlnAspAsnPheIleSerValAlaG-luProValSerThrAlaSerGlnAlaSerAla GlyLeuLeuLeuGlyGlyGlyG-lyGlnGlySerGlyGlyArgArgLysArgArgLeuAlaThrVal-LeuProGlyLeu;

(n) SerSerLeuThrProValProGluThrGlySerTyrVal AlaG-lyAlaAlaAlaSerProMetCysSer-LeuCysGluGlyArgAlaProAlaValCys LeuAsnThrLeuPhePheArgLeuArgAspArgPheProPro-ValMetSerThrGlnArg ArgAspproTyrValIleSerGlyAla-SerGlySerTyrAsnGluThrAspPheLeuGly AsnPh-eLeuAsnPheIleAspLysGlu-AspAspGlyGlnArgProAspAspGluProArg TyrThrTyrTrpGlnLeuAsnGlnAsn-LeuLeuGluArgLeuSerArgLeuGlyIleAsp AlaGluG-lyLysLeuGluLysGluProGlyGluA-laCysAlaSerLeuThrArgAspAsp AlaGluTyrneuLeuGlyArgPheSer-ValLeuAlaAspSerValLeuGluThrLeuAla ThrIleAlaSer-SerGlyIleGluTrpThrAlaGluAlaA-laArgAspPheLeuGluGly ValTrpGlyGlyProGlyAlaAlaGl-nAspAsnPheIleSerValAlaGluProValSer ThrAlaSer-GlnAlaSerAlaGlyLeuLeuLeuGlyG-lyGlyGlyGlnGlySerGlyGly ArgArgLysArgArgLeuAlaThrValLeuProGlyLeu; and (o) SerSerLeuThrProValProGluThrGlySerTyrVal AlaG-lyAlaAlaAlaSerProMetCysSer-LeuCysGluGlyArgAlaProAlaValCys LeuAsnThrLeuphepheArgLeuArgAspArgPheProPro-ValMetSerThrGlnArg ArgAspProTyrValIleSerGlyAla-SerGlySerTyrAsnGluThrAspPheLeuGly AsnPh-eLeuAsnPheIleAspLysGlu-AspAspGlyGlnArgProAspAspGluProArg TyrThrTyrTrpGlnLeuAsnGlnAsn-LeuLeuGluArgLeuSerArgLeuGlyIleAsp AlaGluG-lyLysLeuGluLysGluProHisG-lyProArgAspPheValLysMetPheLys AspValAspAlaAlaValAspAlaGlu-ValValGlnPheMetAsnSerMetAlaLysAsn AsnIleThr-TyrLysAspLeuValLysSerCy-sTyrHisValMetGlnTyrSerCysAsn ProPheAlaGlnProAlaCysProIle-PheThrGlnLeuPheTyrArgSerLeuLeuThr IleLeuGlnAlaProGlyAlaG-lyLeuArgLysGlnAlaGlyGlySerSerMetArgLys LyspheValpheAlaThrProThrLeuG-lyLeuThrValLysArgArgThrGlnAlaAla ThrThrTyr-GluIleGluAsnIleArgAlaGlyLeu-GluAlaIleIleSerGlnLysGln GluGluAspCysValPheAspValVal-CysAsnLeuValAsPAlaMetGlyGluAlaCys AlaSer-LeuThrArgAspAspAlaGluTyr-LeuLeuGlyArgPheSerValLeuAlaAsp SerValLeuGluThrLeuAlaTh-rIleAlaSerSerGlyIleGluTrpThrAlaGluAla AlaArgAsp-PheLeuGluGlyValTrpGlyGlyPro-GlyAlaAlaGlnAspAsnPheIle SerValAlaGluProValSerThrAla-SerGlnAlaSerAlaGlyLeuLeuLeuGlyGly.

4. An isolated antigen consisting of at least one protein according to any one of claims 1, 2 or 3.

5. An antigenic composition comprising at least one antigen of claim 4 in an appropriate medium, wherein said antigen is capable of binding to anti-EBV antibodies.

6. A method of detecting anti-EBV antibodies in a sample comprising:

incubating said composition according to claim 5 with a sample suspected of containing anti-EBV antibodies under conditions sufficient to allow antibody-antigen binding; and detecting said antibody-antigen binding.

7. An isolated antigen consisting of at least two proteins according to any one of claims 1, 2 or 3 covalently linked together.

8. An antigenic composition comprising at least one antigen of claim 7 in an appropriate medium, wherein said antigen is capable of binding to anti-EBV antibodies.

9. A method of detecting anti-EBV antibodies in a sample comprising:

incubating said composition according to claim 8 with a sample suspected of containing anti-EBV antibodies under conditions sufficient to allow antibody-antigen binding; and detecting said antibody-antigen binding.

* * * * *